US008460887B2

(12) United States Patent
Goldberg et al.

(10) Patent No.: US 8,460,887 B2
(45) Date of Patent: *Jun. 11, 2013

(54) SENSITIVE AND RAPID DETERMINATION OF ANTIMICROBIAL SUSCEPTIBILITY

(75) Inventors: David A. Goldberg, Boulder, CO (US); David C. Howson, Denver, CO (US); Steven W. Metzger, Westminster, CO (US); Daniel A. Buttry, Laramie, WY (US); Steven Scott Saavedra, Tucson, AR (US)

(73) Assignee: Accelerate Diagnostics, Inc., Tucson, AZ (US)

( * ) Notice: Subject to any disclaimer, the term of this patent is extended or adjusted under 35 U.S.C. 154(b) by 128 days.

This patent is subject to a terminal disclaimer.

(21) Appl. No.: 12/702,210

(22) Filed: Feb. 8, 2010

(65) Prior Publication Data
US 2010/0136570 A1 Jun. 3, 2010

Related U.S. Application Data

(62) Division of application No. 10/888,828, filed on Jul. 8, 2004, now Pat. No. 7,687,239.

(60) Provisional application No. 60/486,605, filed on Jul. 12, 2003, provisional application No. 60/571,479, filed on May 13, 2004.

(51) Int. Cl.
*G01N 33/53* (2006.01)

(52) U.S. Cl.
USPC .......................................................... 435/7.2

(58) Field of Classification Search
None
See application file for complete search history.

(56) References Cited

U.S. PATENT DOCUMENTS

| | | | |
|---|---|---|---|
| 3,493,772 A | 2/1970 | Daughters, II et al. | |
| 3,811,036 A | 5/1974 | Perry | |
| 3,832,532 A | 8/1974 | Praglin et al. | |
| 3,935,073 A | 1/1976 | Waters | |
| 4,199,449 A | 4/1980 | Slejko | |
| 4,199,499 A | 4/1980 | Smithwick, Jr. et al. | |
| 4,200,493 A * | 4/1980 | Wilkins et al. | 204/403.01 |
| 4,246,343 A | 1/1981 | Wilkins et al. | |
| 4,259,442 A | 3/1981 | Gayral | |
| 4,288,543 A | 9/1981 | Sielaff et al. | |
| 4,313,734 A | 2/1982 | Leuvering | |
| 4,481,137 A | 11/1984 | Ohnishi et al. | |
| 4,487,839 A | 12/1984 | Kamentsky | |
| 4,508,832 A | 4/1985 | Carter et al. | |
| 4,521,522 A | 6/1985 | Lundström et al. | |
| 4,537,861 A | 8/1985 | Elings et al. | |
| 4,643,968 A * | 2/1987 | Weaver | 435/32 |
| 4,716,123 A | 12/1987 | Wood | |
| 4,752,567 A | 6/1988 | De Brabander et al. | |
| 4,778,758 A | 10/1988 | Ericsson et al. | |
| 4,805,623 A | 2/1989 | Jöbsis | |
| 4,876,208 A | 10/1989 | Gustafson et al. | |
| 4,885,077 A | 12/1989 | Karakelle et al. | |
| 5,017,009 A | 5/1991 | Schutt et al. | |
| 5,066,465 A | 11/1991 | Kano et al. | |
| 5,079,172 A | 1/1992 | Hari et al. | |
| 5,082,630 A | 1/1992 | Partin et al. | |
| 5,173,164 A | 12/1992 | Egen et al. | |
| 5,196,527 A | 3/1993 | Ookuma et al. | |
| 5,240,618 A | 8/1993 | Caldwell et al. | |
| 5,288,611 A | 2/1994 | Kohne | |
| 5,314,805 A | 5/1994 | Haugland et al. | |
| 5,329,461 A | 7/1994 | Allen et al. | |
| 5,350,697 A | 9/1994 | Swope et al. | |
| 5,405,783 A | 4/1995 | Pirrung et al. | |
| 5,466,416 A | 11/1995 | Ghaed et al. | |
| 5,488,567 A | 1/1996 | Allen et al. | |
| 5,496,701 A | 3/1996 | Pollard-Knight | |
| 5,556,764 A | 9/1996 | Sizto et al. | |
| 5,578,460 A * | 11/1996 | Ebersole et al. | 435/29 |
| 5,599,668 A | 2/1997 | Stimpson et al. | |
| 5,604,099 A | 2/1997 | Erlich et al. | |
| 5,622,868 A | 4/1997 | Clarke et al. | |
| 5,656,432 A | 8/1997 | Claverys et al. | |
| 5,792,622 A | 8/1998 | Botsford | |

(Continued)

FOREIGN PATENT DOCUMENTS

| | | |
|---|---|---|
| EP | 0498920 A2 | 8/1992 |
| EP | 1648286 | 4/2006 |

(Continued)

OTHER PUBLICATIONS

Ateya, et al., "VolumeCytometry: Microfluidic Sensor for High-Throughput Screening in Real Time", Anal. Chem., 77, 2004, 1290-1294.
Bae, et al., "Immunosensor for Detection of Yersinia Enterocolitica Based on Imaging Ellipsometry", Anal. Chem., 76, 2004, 1799-1803.
Balaban, et al., "Bacterial Persistence as a Phenotypic Switch", Science, 305, 2004, 1622-1625.
Barton, et al., "Measurement of Bacterial Growth Rates on Polymers", J. Biomed. Materials Res., 32, 1996, 271-278.
Beaglehole, "Performance of a Microscopic Imaging Ellipsometer", Rev. Sci. Instrum., 59 (12), 1988, 2557-2559.
Benecky, et al., "Simultaneous Detection of Multiple Analytes Using Copalis Technology: A Reduction to Practice", Clin. Chem., 44(9), 1998, 2052-2054.
Bridson, et al., "Quantal Microbiology", Lett. Appl. Microbiology, 30, 2000, 95-98.

(Continued)

Primary Examiner — Ann Lam
(74) Attorney, Agent, or Firm — Snell & Wilmer, L.L.P.

(57) ABSTRACT

The present invention relates to moving microorganisms to a surface, where they are grown in the presence and absence of antimicrobials, and by monitoring the growth of the microorganisms over time in the two conditions, their susceptibility to the antimicrobials can be determined. The microorganisms can be moved to the surface through electrophoresis, centrifugation or filtration. When the movement involves electrophoresis, the presence of oxidizing and reducing reagents lowers the voltage at which electrophoretic force can be generated and allows a broader range of means by which the target can be detected. Monitoring can comprise optical detection, and most conveniently includes the detection of individual microorganisms. The microorganisms can be stained in order to give information about their response to antimicrobials.

15 Claims, 43 Drawing Sheets

U.S. PATENT DOCUMENTS

| | | | |
|---|---|---|---|
| 5,828,716 | A | 10/1998 | Bisconte de Saint Julien |
| 5,843,651 | A | 12/1998 | Stimpson et al. |
| 5,849,486 | A | 12/1998 | Heller et al. |
| 5,866,345 | A | 2/1999 | Wilding et al. |
| 5,872,013 | A | 2/1999 | Leunissen et al. |
| 5,993,634 | A | 11/1999 | Simpson et al. |
| 6,017,696 | A | 1/2000 | Heller |
| 6,043,048 | A | 3/2000 | Johnston et al. |
| 6,051,380 | A | 4/2000 | Sosnowski et al. |
| 6,054,270 | A | 4/2000 | Southern |
| 6,099,803 | A | 8/2000 | Ackley et al. |
| 6,101,946 | A | 8/2000 | Martinsky |
| 6,107,054 | A * | 8/2000 | Gibbs ............................. 435/32 |
| 6,136,171 | A | 10/2000 | Frazier et al. |
| 6,143,247 | A | 11/2000 | Sheppard, Jr. et al. |
| 6,153,416 | A | 11/2000 | Yuan |
| 6,176,620 | B1 | 1/2001 | Obara |
| 6,214,560 | B1 | 4/2001 | Yguerabide et al. |
| 6,245,508 | B1 | 6/2001 | Heller et al. |
| 6,251,615 | B1 | 6/2001 | Oberhardt |
| 6,251,616 | B1 | 6/2001 | Barbera-Guillem et al. |
| 6,264,825 | B1 | 7/2001 | Blackburn et al. |
| 6,270,953 | B1 | 8/2001 | Malcus-Vocanson et al. |
| 6,290,839 | B1 | 9/2001 | Kayyem et al. |
| 6,379,897 | B1 | 4/2002 | Weidenhammer et al. |
| 6,391,546 | B1 | 5/2002 | Karube et al. |
| 6,391,577 | B1 | 5/2002 | Mikkelsen et al. |
| 6,403,367 | B1 | 6/2002 | Cheng et al. |
| 6,472,166 | B1 | 10/2002 | Wardlaw et al. |
| 6,472,228 | B2 | 10/2002 | Wang et al. |
| 6,548,263 | B1 | 4/2003 | Kapur et al. |
| 6,551,841 | B1 | 4/2003 | Wilding et al. |
| 6,605,453 | B2 | 8/2003 | Ozkan et al. |
| 6,611,765 | B2 | 8/2003 | Boeufgras et al. |
| 6,716,620 | B2 | 4/2004 | Bashir et al. |
| 6,809,862 | B2 | 10/2004 | Behnsen et al. |
| 6,841,379 | B2 | 1/2005 | Matson |
| 6,844,028 | B2 | 1/2005 | Mao et al. |
| 7,108,775 | B2 | 9/2006 | Bahatt et al. |
| 7,214,299 | B2 * | 5/2007 | Armstrong .................... 204/455 |
| 7,258,837 | B2 | 8/2007 | Yager et al. |
| 7,306,924 | B2 | 12/2007 | Gomez et al. |
| 7,341,841 | B2 | 3/2008 | Metzger et al. |
| 7,435,579 | B2 | 10/2008 | Bashir et al. |
| 7,510,637 | B2 | 3/2009 | Barlow et al. |
| 7,642,068 | B2 * | 1/2010 | Steiner et al. .................. 435/32 |
| 7,687,239 | B2 | 3/2010 | Goldberg et al. |
| 8,071,319 | B2 | 12/2011 | Metzger et al. |
| 2001/0009774 | A1 | 7/2001 | Shin et al. |
| 2001/0053535 | A1 | 12/2001 | Bashir et al. |
| 2002/0028519 | A1 | 3/2002 | Yguerabide et al. |
| 2002/0119455 | A1 | 8/2002 | Chan |
| 2002/0155490 | A1 | 10/2002 | Skinner et al. |
| 2003/0036054 | A1 | 2/2003 | Ladisch et al. |
| 2003/0119028 | A1 | 6/2003 | Graves et al. |
| 2003/0124623 | A1* | 7/2003 | Yager et al. .................... 435/7.5 |
| 2003/0147132 | A1 | 8/2003 | Behnsen et al. |
| 2003/0153023 | A1 | 8/2003 | Starzl et al. |
| 2003/0157587 | A1 | 8/2003 | Gomez et al. |
| 2003/0170613 | A1* | 9/2003 | Straus ............................... 435/5 |
| 2003/0186341 | A1 | 10/2003 | Kuhn et al. |
| 2004/0089546 | A1 | 5/2004 | Bahatt et al. |
| 2004/0189311 | A1 | 9/2004 | Glezer et al. |
| 2005/0048599 | A1 | 3/2005 | Goldberg et al. |
| 2005/0112544 | A1 | 5/2005 | Xu et al. |
| 2006/0166184 | A1 | 7/2006 | Yasuda et al. |
| 2007/0037225 | A1 | 2/2007 | Metzger et al. |
| 2007/0298513 | A1 | 12/2007 | Starzl et al. |
| 2008/0241858 | A1 | 10/2008 | Metzger et al. |
| 2010/0048428 | A1 | 2/2010 | Coyer et al. |

FOREIGN PATENT DOCUMENTS

| | | |
|---|---|---|
| GB | 1520733 | 8/1978 |
| JP | 2001-509008 | 7/2001 |
| JP | 2002-500892 | 1/2002 |
| JP | 2002-502597 | 1/2002 |
| JP | 2002-330799 | 11/2002 |
| JP | 2003-527601 | 9/2003 |
| JP | 2004-81019 | 3/2004 |
| WO | WO 90/11525 | 10/1990 |
| WO | WO 94/02831 | 2/1994 |
| WO | WO 95/28641 | 10/1995 |
| WO | 96/14431 A1 | 5/1996 |
| WO | 98/22618 A1 | 5/1998 |
| WO | WO 98/22808 | 5/1998 |
| WO | WO 99/20789 | 4/1999 |
| WO | 99/37799 A1 | 7/1999 |
| WO | 99/40174 A1 | 8/1999 |
| WO | WO 99/58948 | 11/1999 |
| WO | WO 00/24941 | 5/2000 |
| WO | 01/69230 A2 | 9/2001 |
| WO | 02/38724 A2 | 5/2002 |
| WO | 03/025208 A1 | 3/2003 |
| WO | WO 03/022999 | 3/2003 |
| WO | WO 03/065009 A2 | 8/2003 |
| WO | WO 03/073100 | 9/2003 |
| WO | WO 2005/027714 | 3/2005 |
| WO | WO 2006/066216 | 6/2006 |

OTHER PUBLICATIONS

Cabrera, et al., "Continuous Concentration of Bacteria in a Microfluidic Flow Cell Using Electrokinetic Techniques", Electrophoresis, 22, 2001, 355-362.

Dai, et al., "Electrokinetic Trapping and Concentration Enrichment of DNA in a Microfluidic Channel", J. Am. Chem. Sox., 125, 2003, 13026-13027.

De Brabander, et al., "Detection of Gold Probes With Video-Enhanced Contrast Microscopy: nanovid Microscopy", Amer. J. Anatomy, 185, 1989, 282-295.

Delehanty, et al., "A Microarray Immunoassay for Simultaneous Detection of Proteins and Bacteria", Anal. Chem., 74, 2002, 5681-5687.

Desai, et al., "Separation, Identification, and Characterization of Microorganisms by Capillary Electrophoresis", Microbiology and Molecular Biology Reviews, 2003, 38-51.

Elfwing, et al., "Observing Growth and Division of Large Numbers of Individual Bacteria by Image Analysis", Appl. Environ. Microbiol., 70, 2004, 675-678.

Elghanian, et al., "Selective Colorimetric Detection of Pooynucleotides Based on the Distance-Dependent Optical Properties of Gold Nanoparticles", Science, 277, 1997, 1078-1081.

Ertl, et al., "Electrochemical Biosensor Array for the Identification of Microorganisms Based on Lectin-Lipopllysaccharide Recognition", Anal. Chem., 73, 2001, 4241-4248.

Ertl, et al., "Rapid Identification of viable *Escherichia coli* Subspecies with Electrochemical Screen-Printed Biosensor Array", Biosens. Bioelectron, 18, 2003, 907-916.

Forero, et al., "Applications of Digital Image Processing XXVI", (Tescher A.G. Ed.), SPIE, vol. 5203, 71-81.

Friedman, et al., "Precise Temporal Modulation in the Response of the SOS DNA Repair Network in Individual Bacteria", PLoS Biol. 3, e238, 2005, 1261-1268.

Gao, et al., "Epipolarization Microscopic Immunogold Assay: A Combination of Immunogold Silver Staining, ELISA and Epipolarization Microscopy", Biotech. & Histochem., 70(4), 1995, 211-216.

Gast, R. K. et al., "Detection of *Salmonella entertidis* in Incubated Pools of Egg Contents by Fluorescence Polarization and Lateral Flow Immunodiffusion", Poultry Science, 82, 2003, 687-690.

Geerts, et al., "Nanovid Microscopy", Nature, vol. 351, 1991, 765-766.

Geesey, et al., "Determination of Bacterial Growth and Activity at Solid-Liquid Interfaces", Annu. Rev. Microbiol., 44, 1990, 579-602.

Huang, et al., "Lysozyme for Capture of Microorganisms on Protein Biochips", Enzy6me and Microbial Technol., 33, 2003, 958-966.

Huang, et al., "Electric Manipulation of Bioparticles and Macromolecules on Microfabricated Electrodes", Anal. Chem., 73, 2001, 1549-1559.

Ji, et al., "Real-Time Detection of Bacterial Contamination in Dynamic Aqueous Environments Using Optical Sensors", Anal. Chem., 76, 2004, 1411-1418.

Jin, et al., "A Biosensor Concept Based on Imaging Ellipsometry for Visualization of Biomolecular Interactions", Anal. Biochem., 232, 1995, 69-72.

Koh, et al., "Integrating Polymerase Chain Reaction, Valving, and Electrophoresis in a Plastic Device for Bacterial Detection", Anal. Chem., 75, 2003, 4591-4598.

Kubitschko, et al., "Refractometric Immunosens Only, Sensitivity Enhancement of Optical Immunosensors with Nanoparticles", Analytical Biochem., 253, 1997, 112-122.

Lagally, et al., "Integrated Portable Genetic Analysis Microsystem for Pathogen/Infectious Disease Detection", Anal. Chem., 76, 2004, 3162-3170.

Lawrence, et al., "Computer-Enhanced Darkfield Microscopy for the Quantitative Analysis of Bacterial Growth and Behavior on Surfaces", J. Microbial. Methods, 10, 1989, 123-138.

Lloyd, et al., "Vigour, Vitality and Viability of Microorganisms", FEMS Microbiology Letters, 133, 1995, 1-7.

Maeyama, et al., "Confocal Imaging of Biofilm Formation Process Using Fluoroprobed *Escherichia coli* and Fluro-stained Exopolysaccharide", J. Biomed. Materials Research, A 70, 2004, 274-282.

Markx, et al., "Dielectrophoretic Characterization and Separation of Micro-Organisms", Microbiology, 140, 1994, 585-591.

Markx, et al., "Dielectrophoretic Separation of Cells: Continuous Separation", Biotechnol. Bioeng., 45, 1885m, 1995, 337-343.

Meinders, et al., "In Situ Enumeration of Bacterial Adhesion in a Parallel Plate Flow Chamber—Elimination or in Focus Flowing Bacteria from the Analysis", J. Microbiol. Methods, 16, 1992, 119-124.

Miller, et al., "SOS Response Induction by Beta-Lactams and Bacterial Defense Against Antibiotic Lethality", Science, 305, 2004, 1629-1631.

Mueller, et al., "Issues in Pharmacokinetics and Pharmacodynamics of Anti-Infective Agents: Kill Curves Versus MIC", Antimicrob. Agents Chemother., 48, 2004, 369-377.

Okano, et al., "Using Microparticle Labeling and Counting for Attomole-Level Detection in Heterogeneous Immunoassay", Analytical Biochem., 202, 1991, 120-125.

Ozkan, et al., "Electro-Optical Platform for the Manipulation of Live Cells", Langmuir, 19, 2002, 1532-1538.

Plowman, "Planar integrated optical methods for examining thin films and their surface alayers (sp?)", Biomaterials, 19, 1996, 341-355.

Rabinovitch, et al., "Removal and Inactivation of *Staphylococcus epidermidis* Biofilms by Electrolysis", Applied and Environmental Microbiology, 72, 2006, 6364-6366.

Rosch, et al., "Chemotaxonomic Identification of Single Bacteria by Micro-Raman Spectroscopy: Application to Clean-Room-Relevant Biological Contaminations", Appl. Environ. Microbial., 71, 2005, 1626-1637.

Rowe, et al., "Array Biosensor for Simultaneous Identification of Bacterial, Viral, and Protein Analytes,", Anal. Chem., 71, 1999, 3846-3852.

Salmon, et al., "Video-Enhanced Differential Interference Contrast Light Microscopy", BioTechniques, 7(6), 1989, 624-633.

Sapsford, et al., "Detection of *Campylobacter* and *Sigella* Species in Food Samples Using an Array Biosensor", Anal. Chem., 76, 2004, 433-440.

Sippy, et al., "Rapid electrochemical detection and identification of catalase positive micro-organisms", Biosensors & Bioelectronics, 18, 2003, pp. 741-749, Available online @ www.sciencedirect.com.

Stewart, et al., "Aging and Death in an Organism that Reproduces by Morphologically Symmetric Division", PLoS Biol., 3, e45, 2005, 295-300.

Stimpson, et al., "Real-Time Detection of DNA Hybridization and Melting on Oligonucleotide Arrays by Using Optical Wave Guides", Genetics, Proc. Natl. Acad. Sci. USA, vol. 92, 1995, 6379-6383.

Taton, et al., "Two-Color Labeling of Oligonucleotide Arrays via Size-Selective Scattering of Nanoparticle Probes", J. Am. Chem. Soc., 123, 2001, 5164-5165.

Tison, "Culture Confirmation of *Escherichia coli* Serotype O157:H7 by Direct Immunofluorescence", J. Clin. Microbiol., 28, 1990, 612-613.

Van Der Borden, et al., "Electric Current-Induced Detachment of *Staphylococcus epidermidis* Biofilms from Surgical Stainless Steel", Applied and Environmental Microbiology, 70, 2004, 6871-6874.

Vener, et al., "A Novel Approach to Nonradioactive Hybridization Assay of Nucleic Acids Using Stained Latex Particles", Analytical Biochem., 198, 1991, 308-311.

Weeraratna, et al., "Gene Expression Profiling: From Microarrays to Medicine", Journal of Clinical Immunology, 24, 2004, 213-224.

Wit, et al., "Application of an Artificial Neural Network in the Enumeration of Yeasts and Bacteria Adhering to Solid Substrata", J. Microbiol. Methods, 32, 1998, 281-290.

European Search Report dated Oct. 15, 2007, EP 03716230.2, 4 pages.

International Search Report dated Jul. 30, 2001, PCT/US1999/010917, 6 pages.

International Search Report dated Jun. 27, 2003, PCT/US2003/006086, 5 pages.

\* cited by examiner

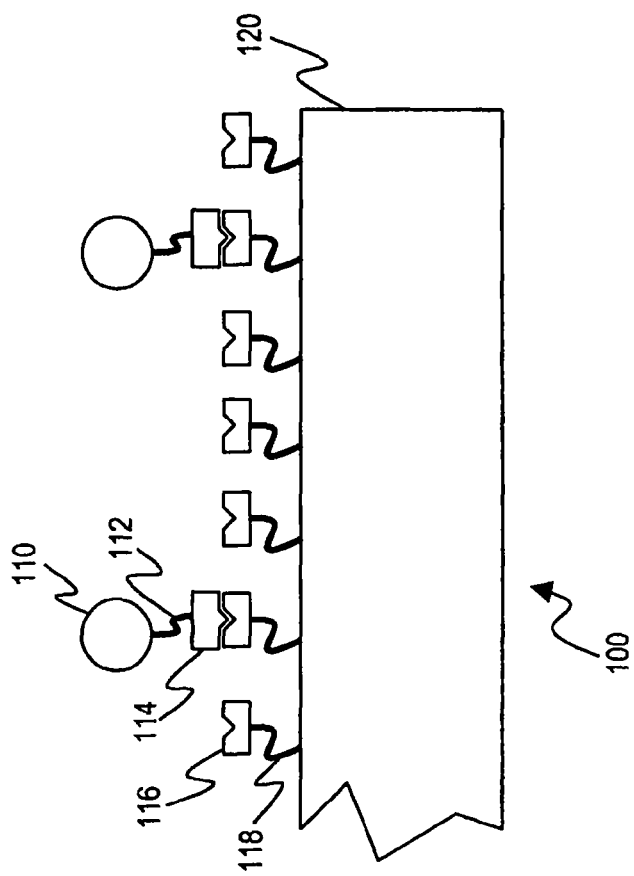
Fig. 1
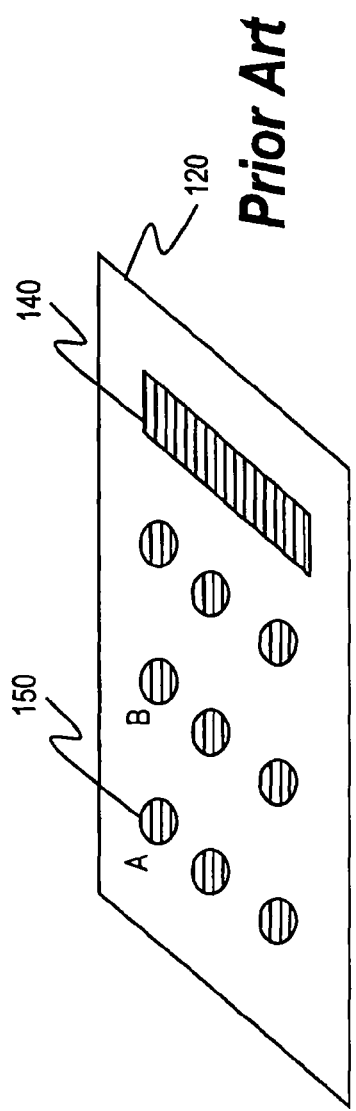
Fig. 3  *Prior Art*

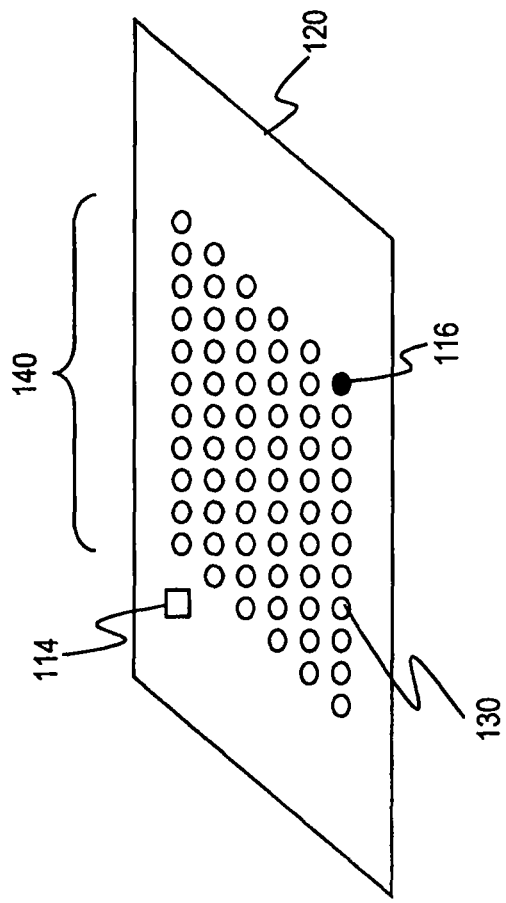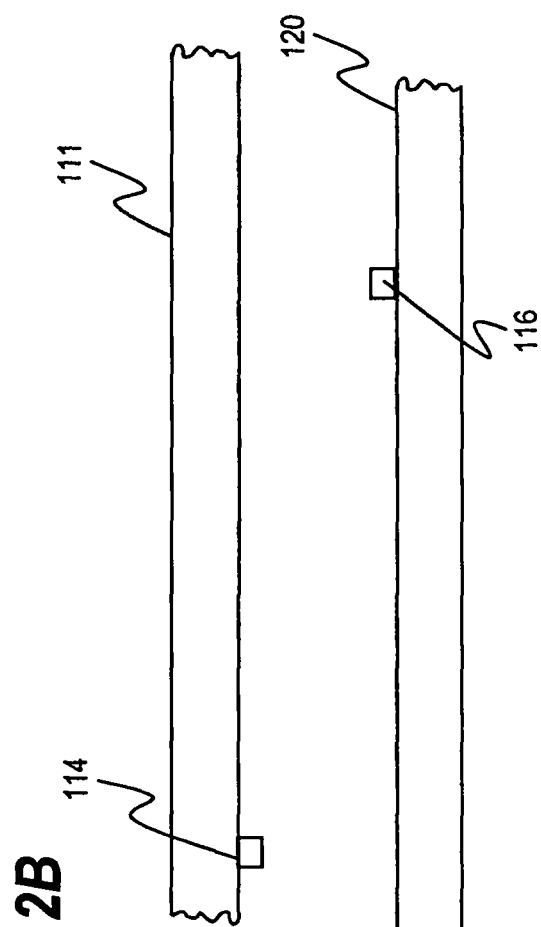

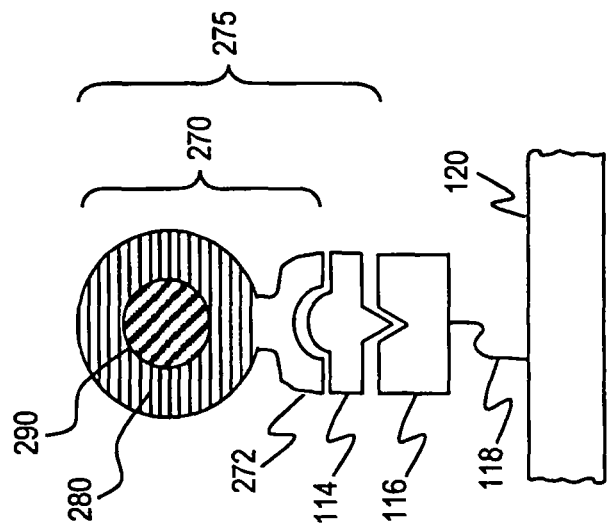
*Fig. 6*
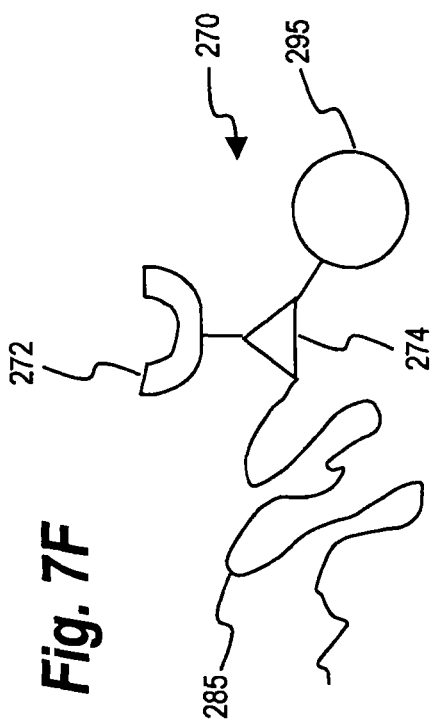
*Fig. 7E*
*Fig. 7F*

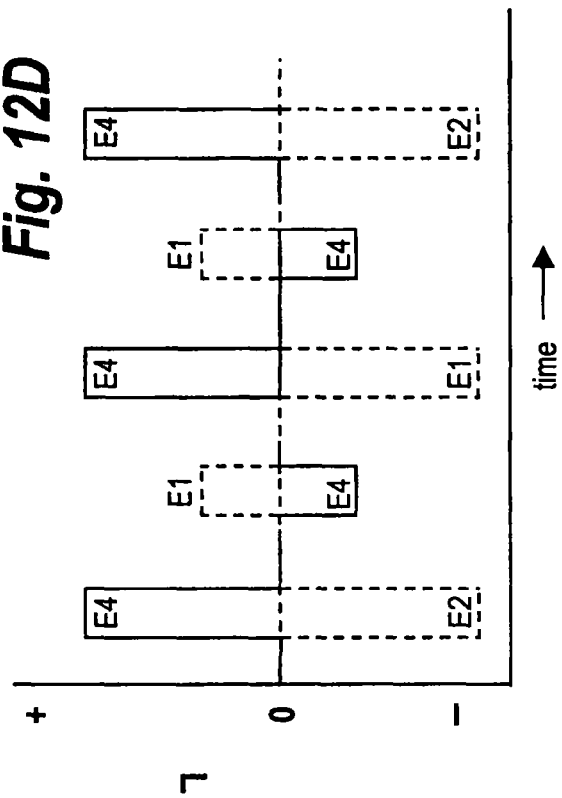
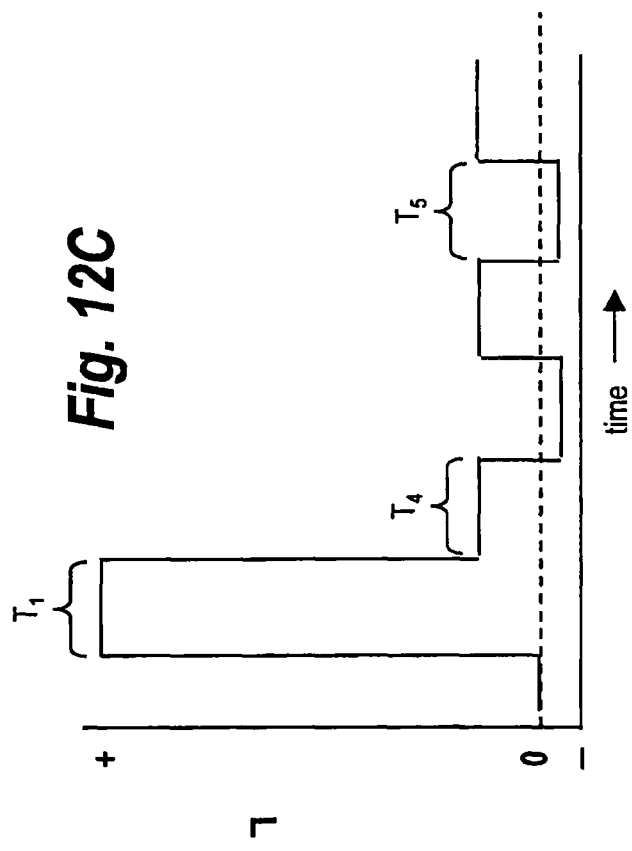

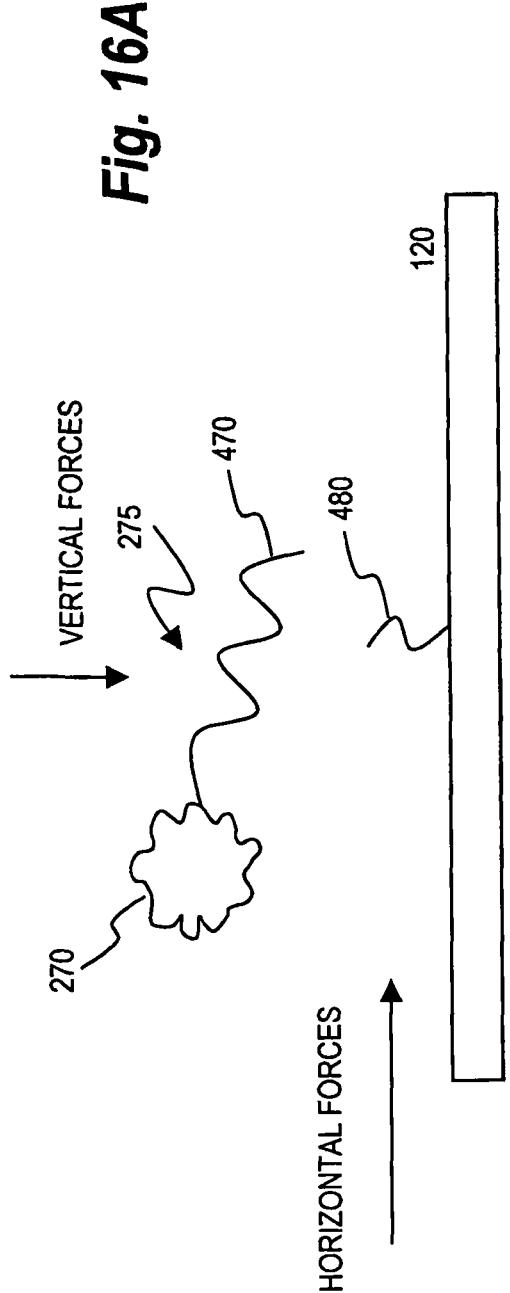

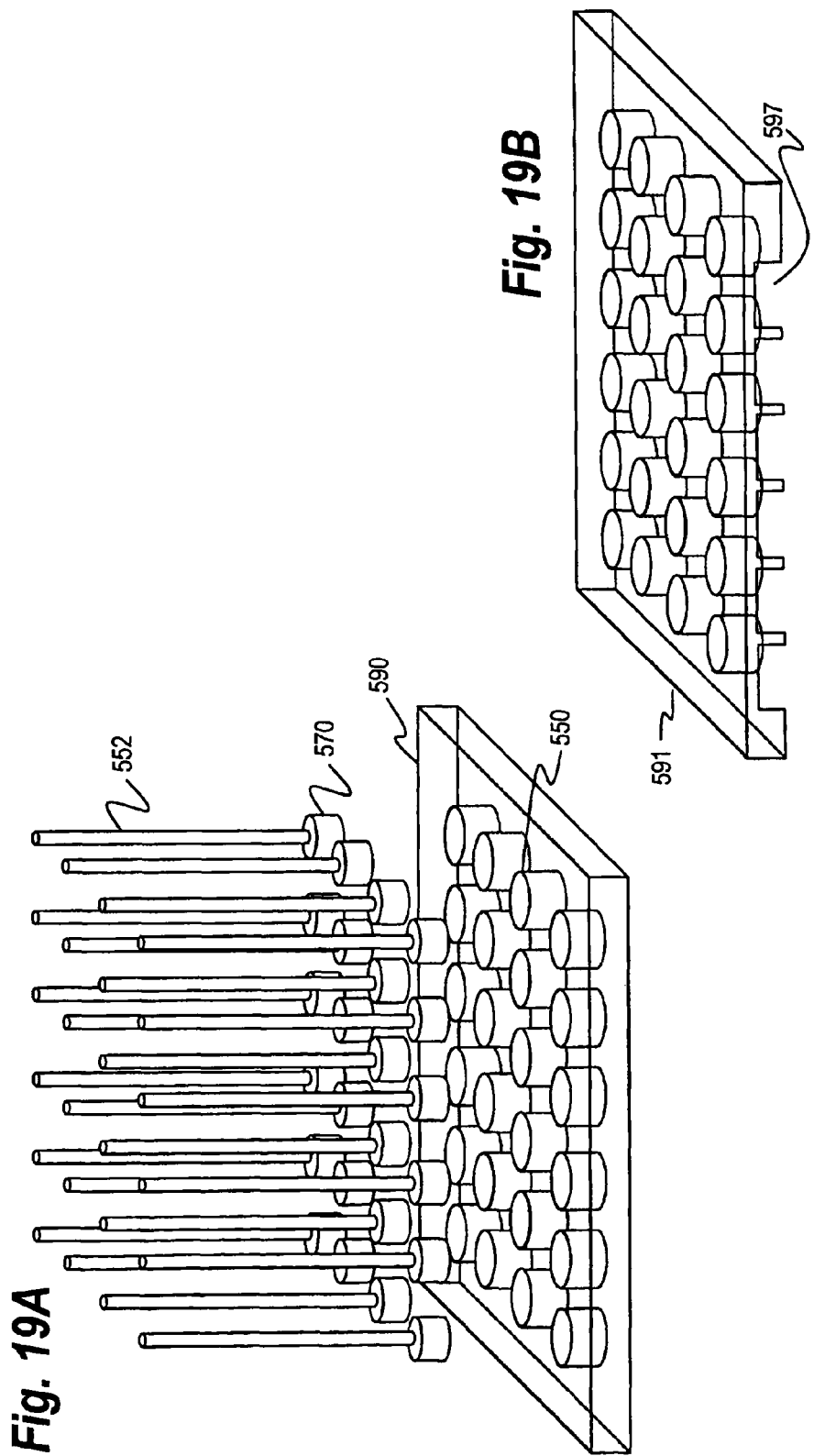

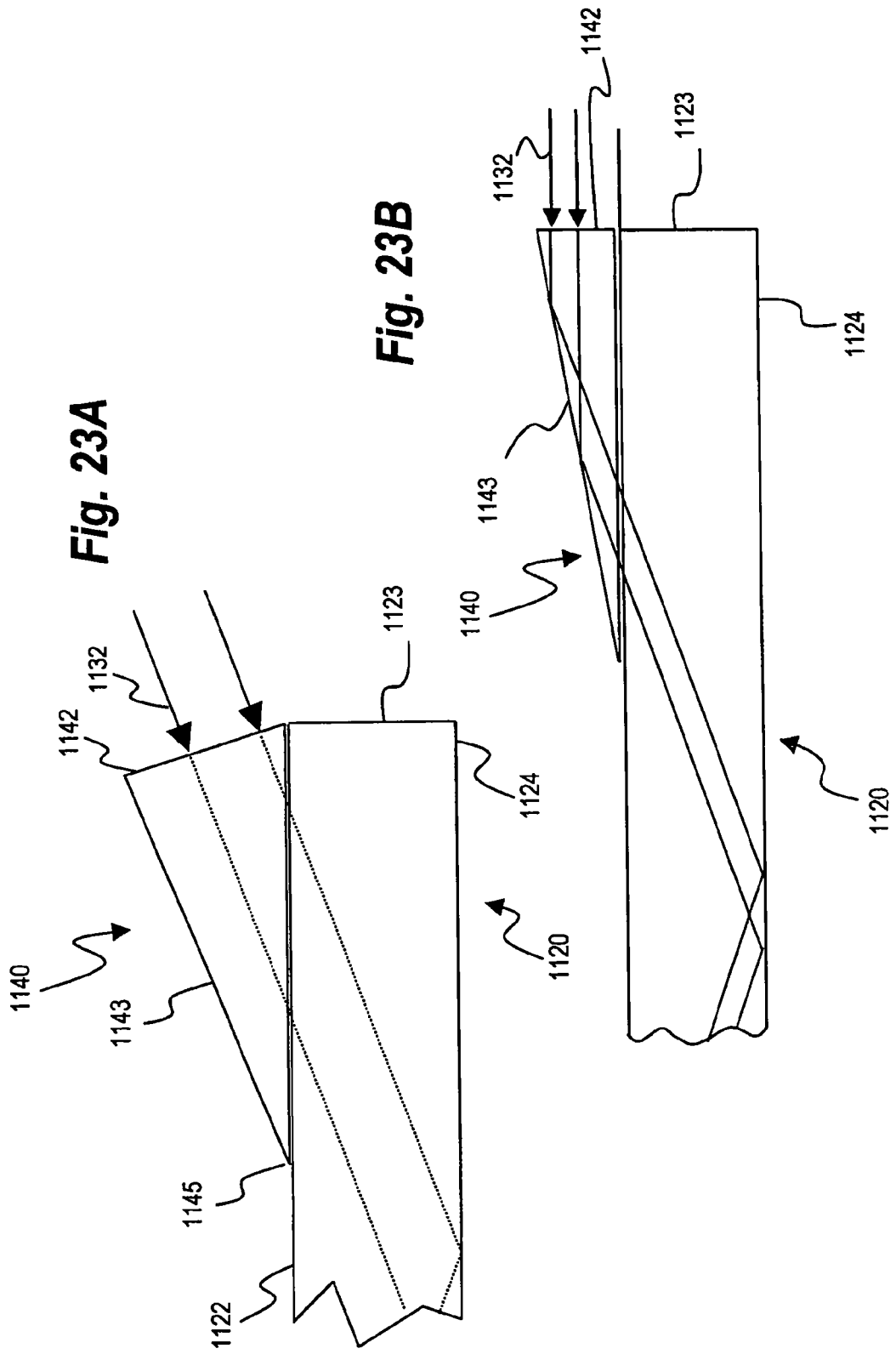

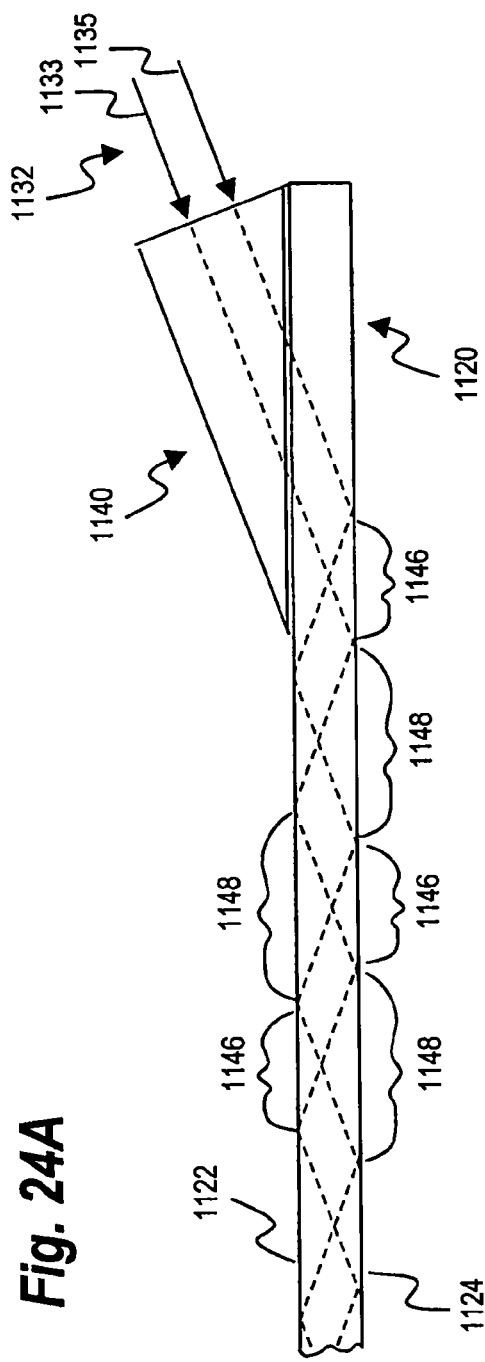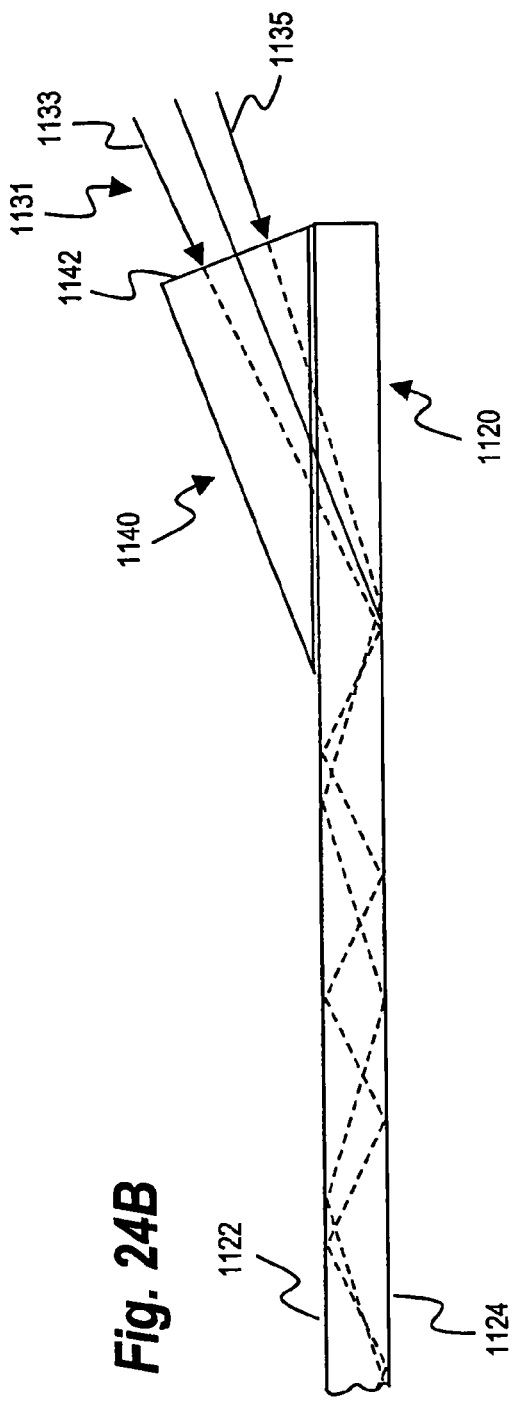

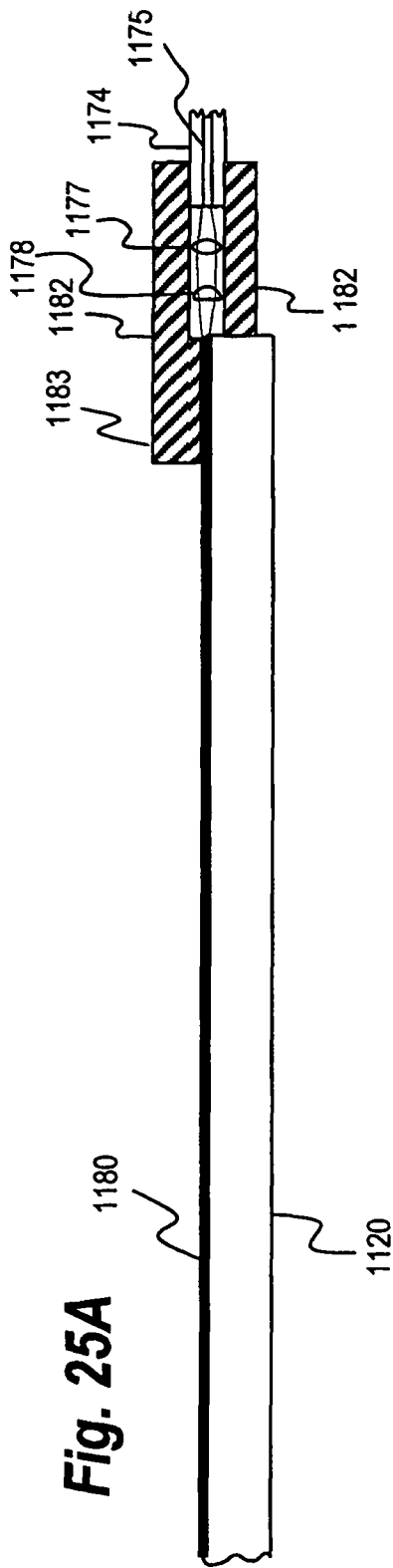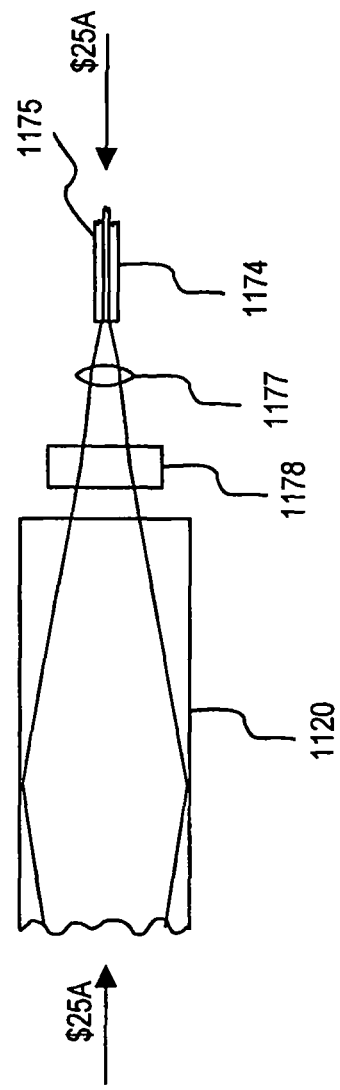
Fig. 25A
Fig. 25B

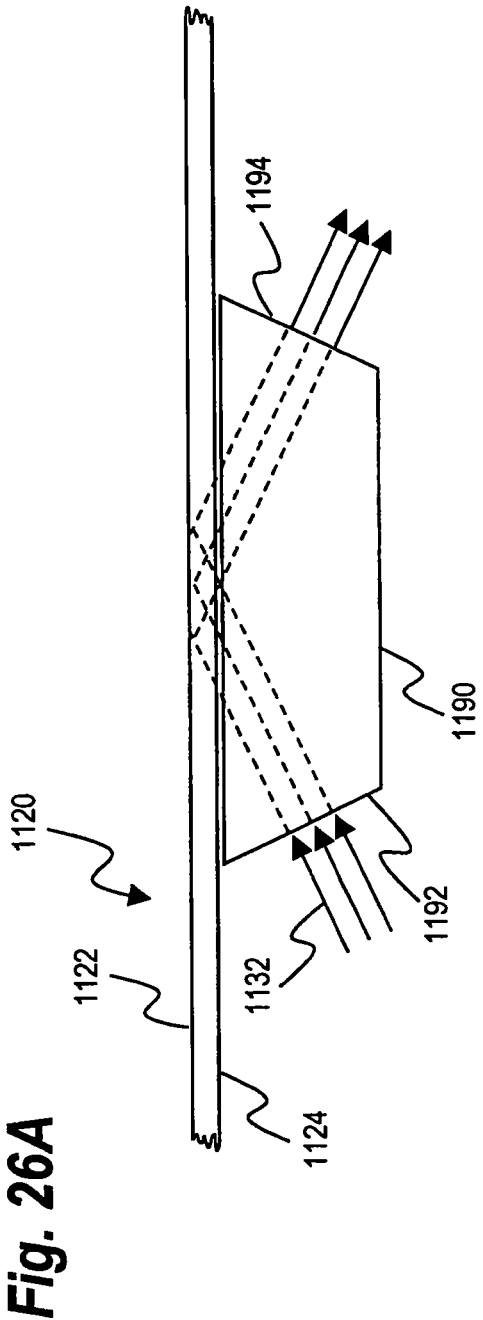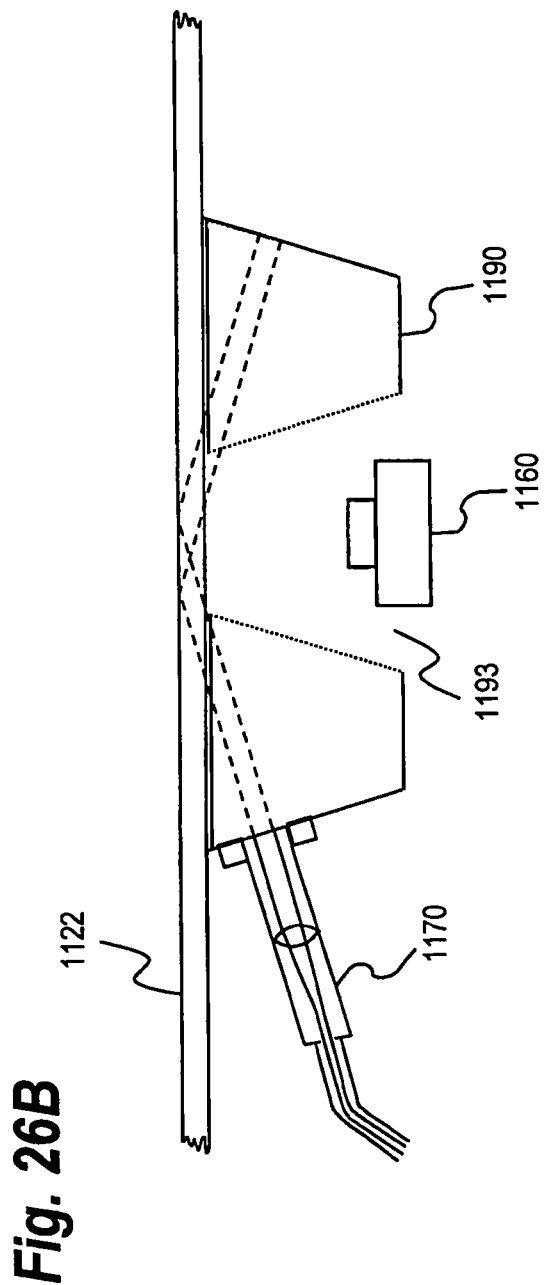

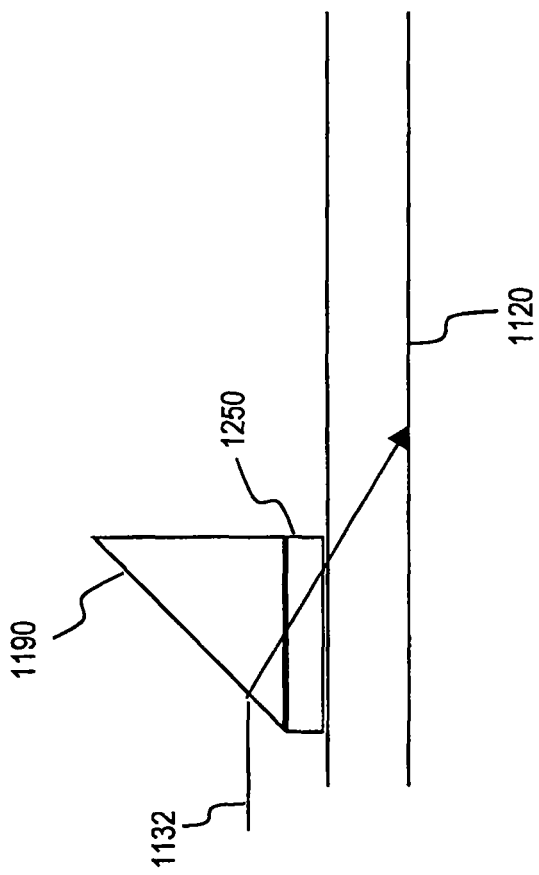

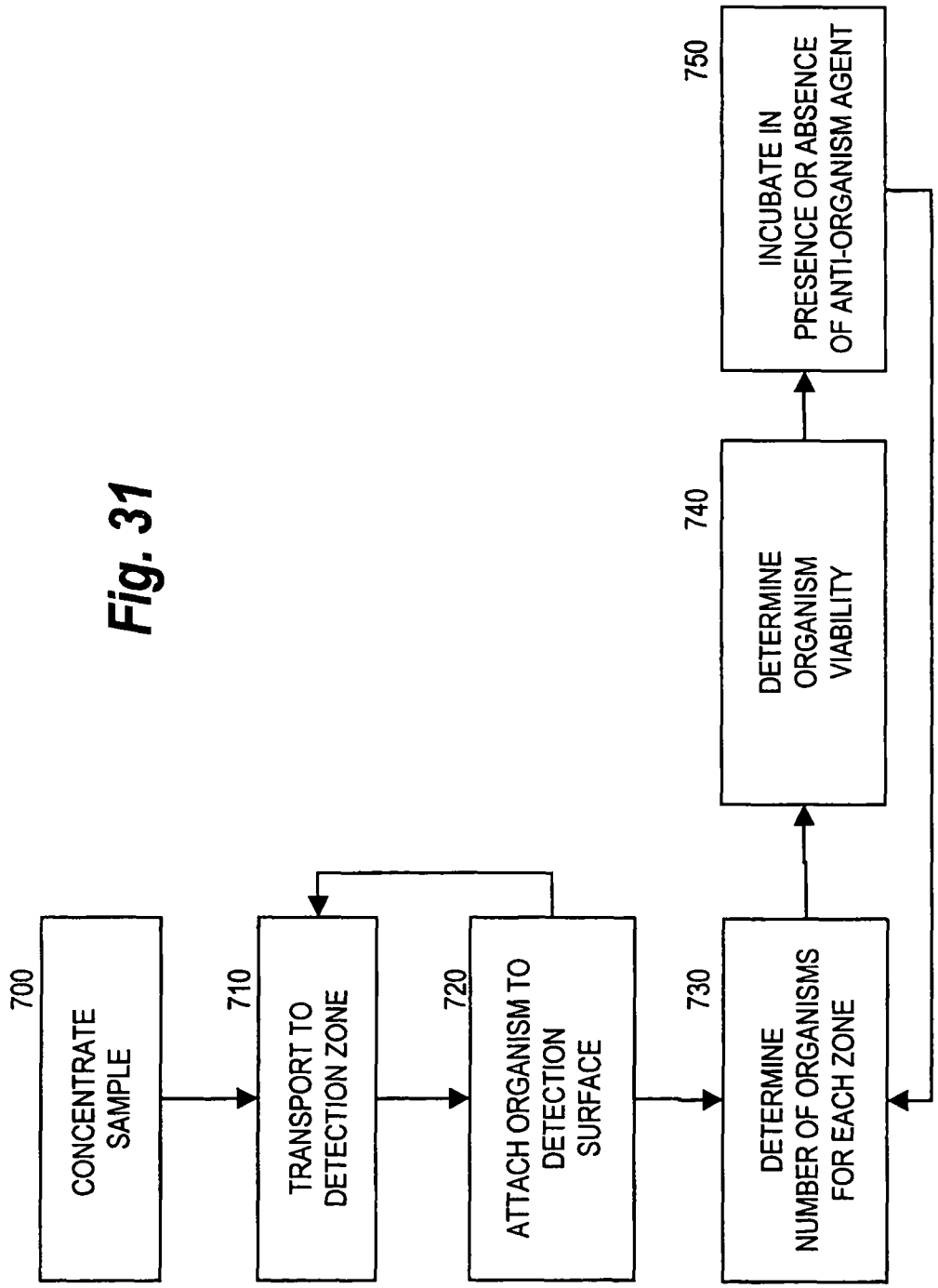

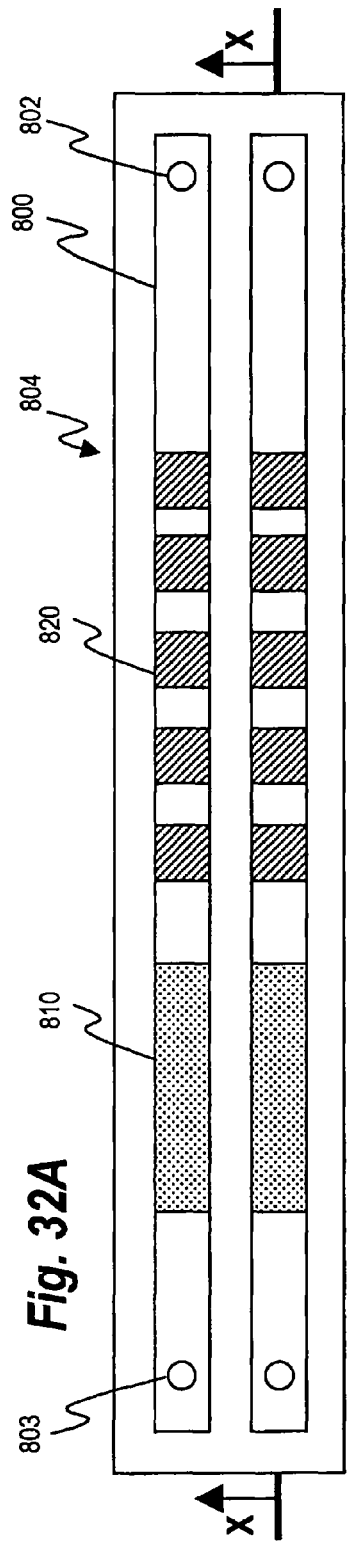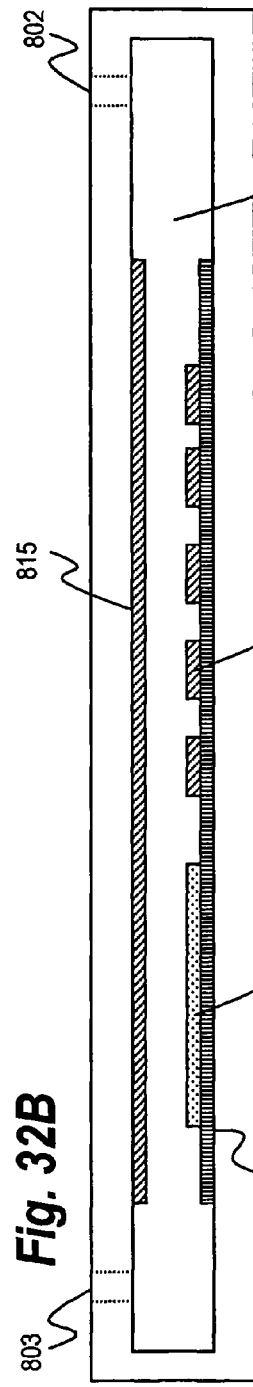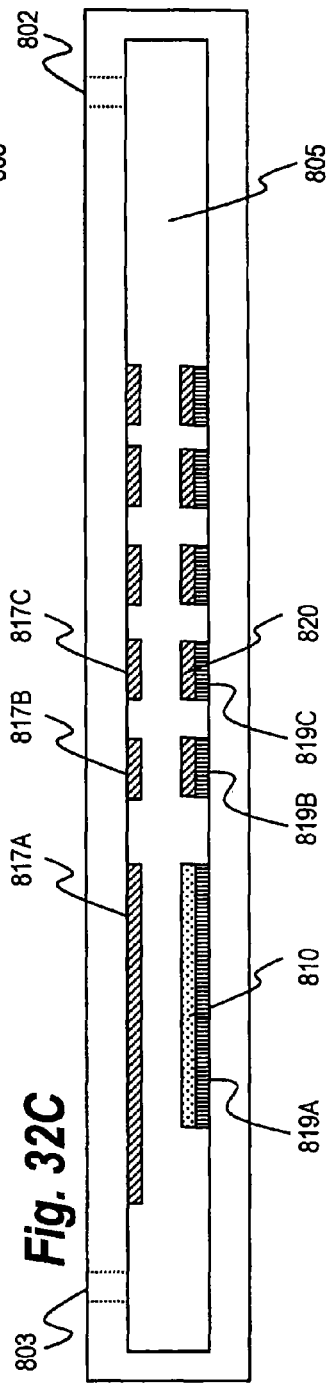

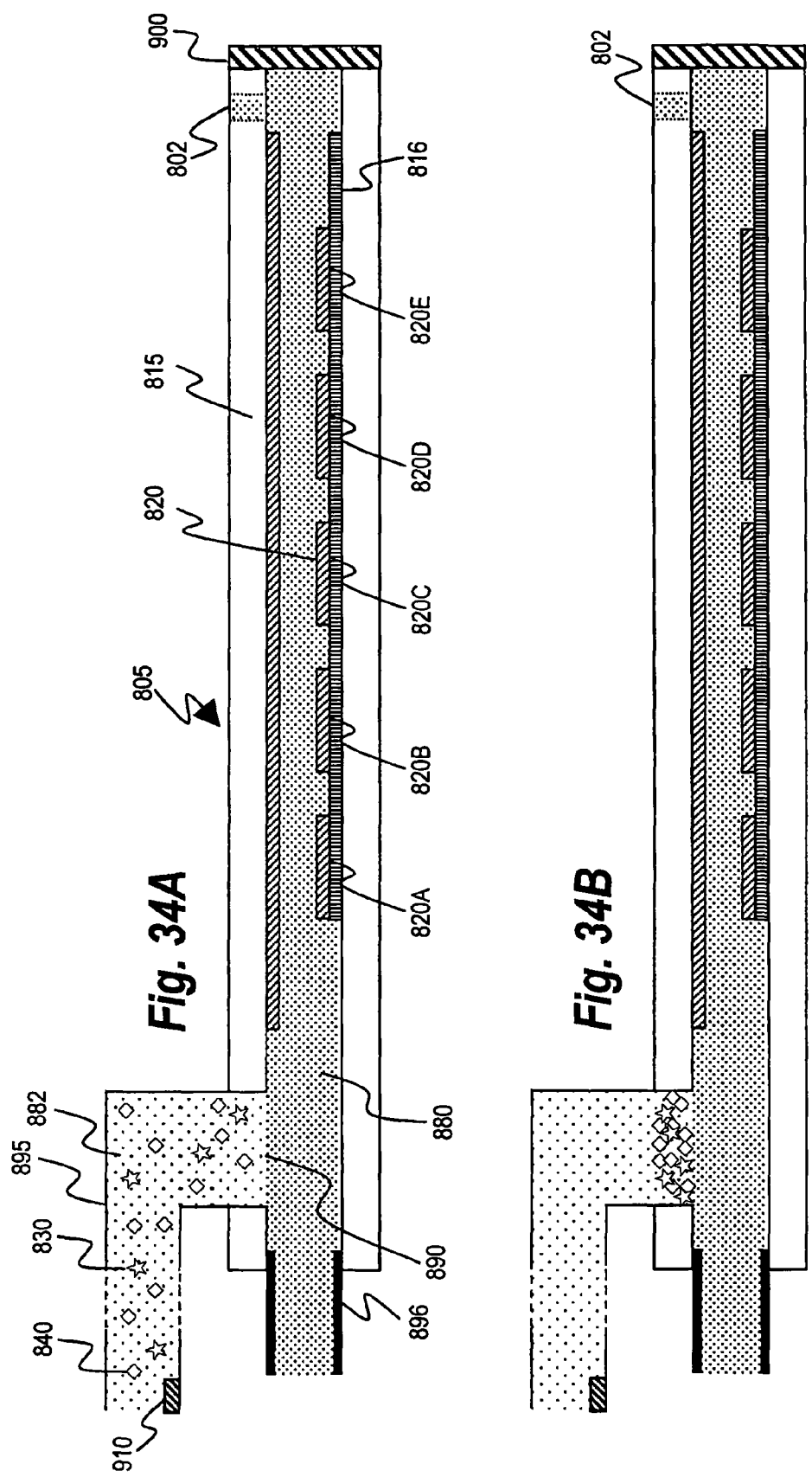

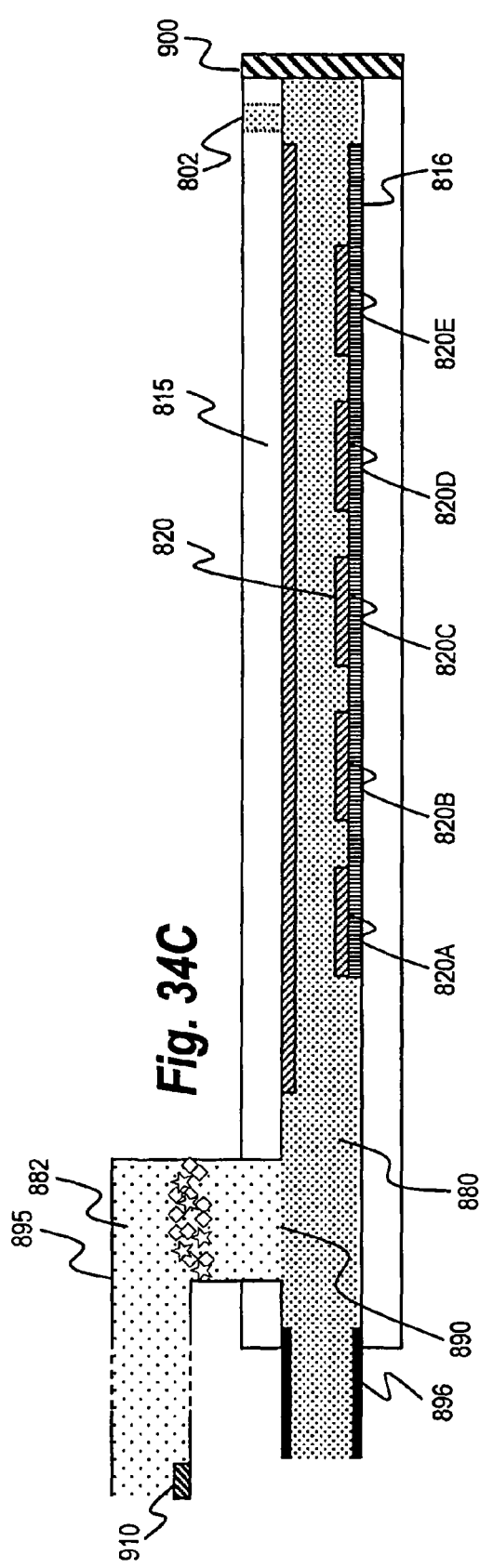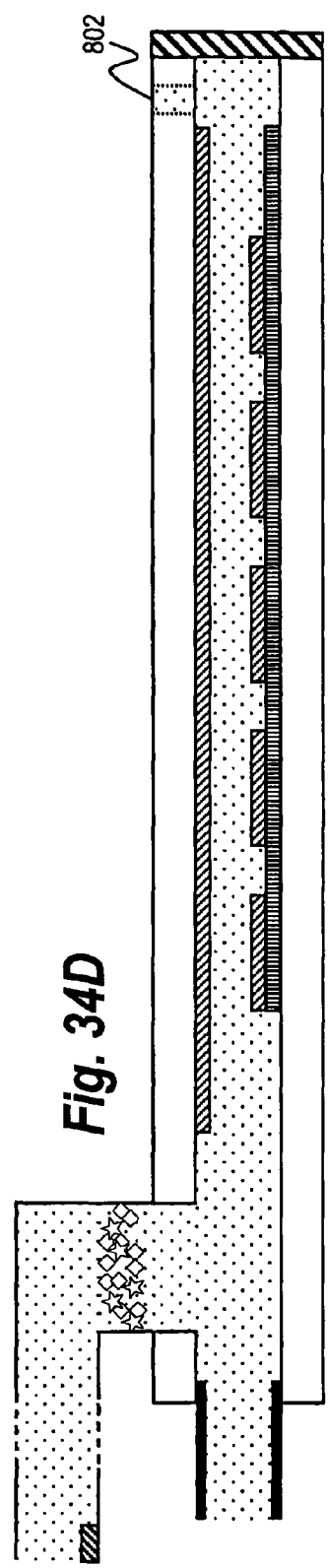

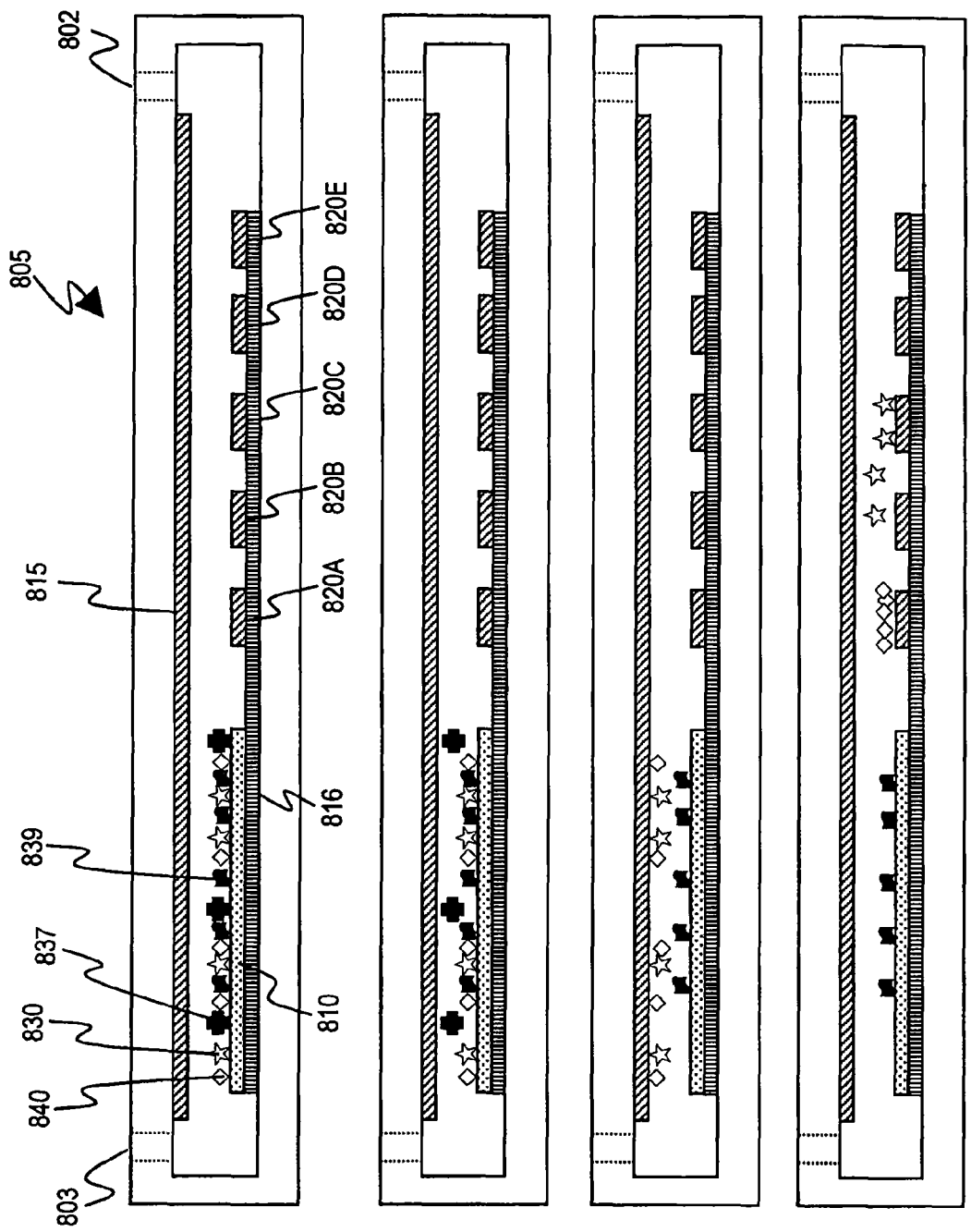

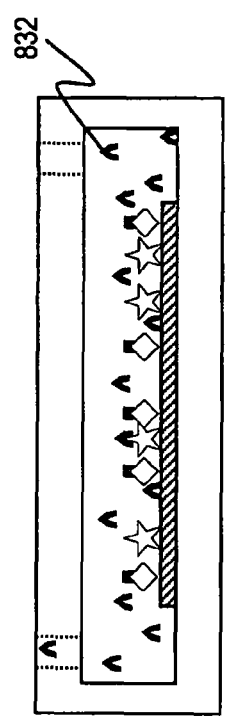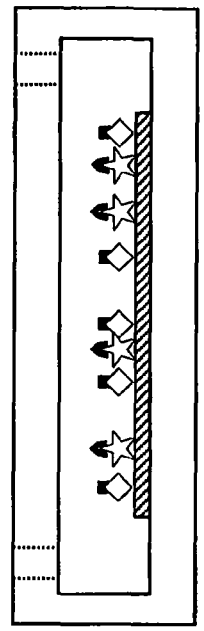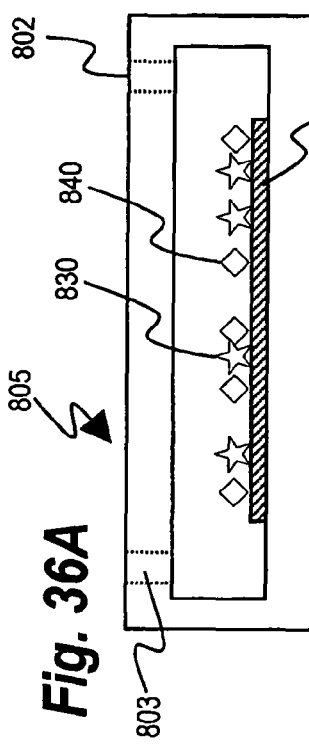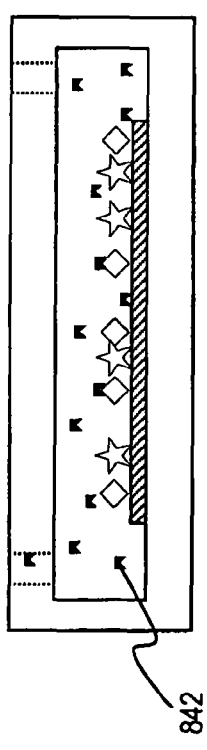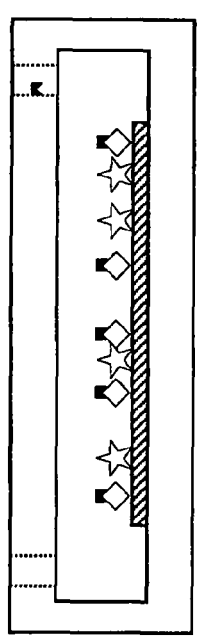
Fig. 36D
Fig. 36E
Fig. 36A
Fig. 36B
Fig. 36C

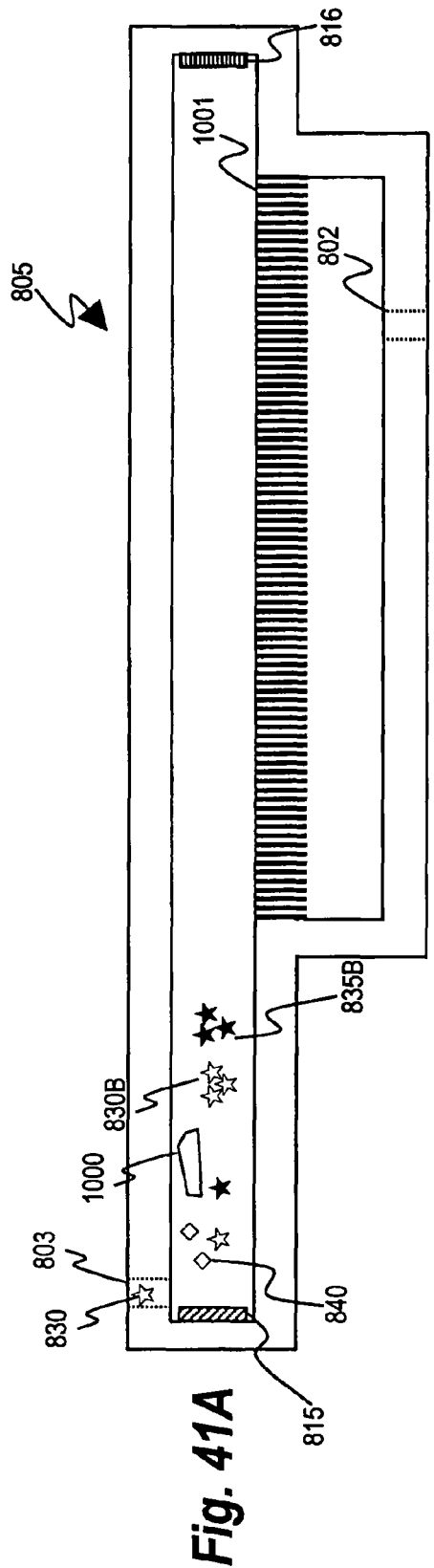
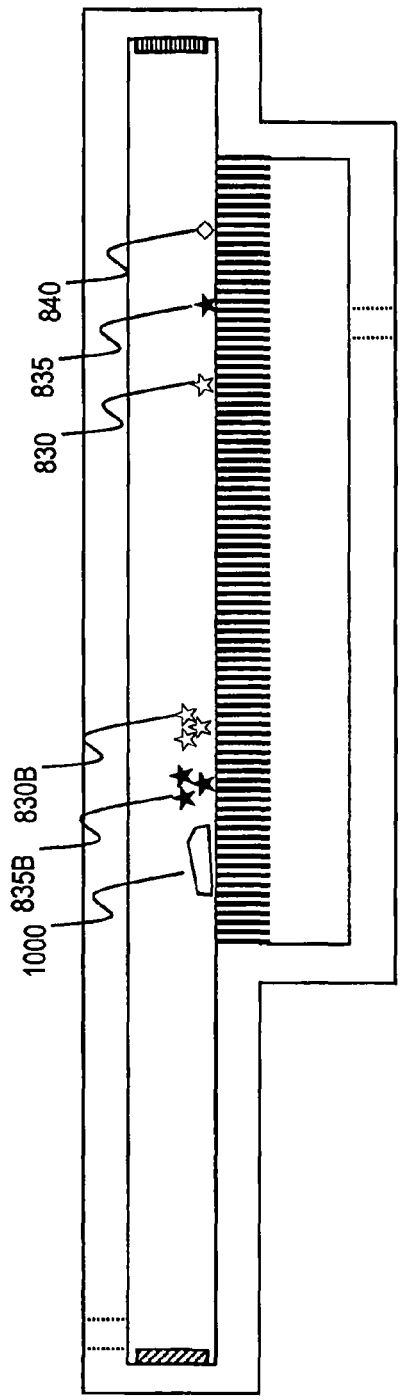

SENSITIVE AND RAPID DETERMINATION OF ANTIMICROBIAL SUSCEPTIBILITY

CROSS REFERENCE TO RELATED PATENT APPLICATIONS

This application is a divisional application of and claims priority under 35 U.S.C. §120 to U.S. patent application Ser. No. 10/888,828, entitled "Sensitive and Rapid Determination of Antimicrobial Susceptibility", filed Jul. 8, 2004, which claims priority to both U.S. Patent Application No. 60/486,605, entitled "Sensitive and Rapid Biodetection", filed Jul. 12, 2003 and U.S. Patent Application No. 60/571,479, entitled "Sensitive and Rapid Biodetection", filed May 13, 2004, and each application listed above is hereby incorporated by reference in their entirety as though fully set forth herein.

TECHNICAL FIELD

The present invention relates to the rapid and sensitive detection of the susceptibility of microorganisms to antimicrobial drugs.

BACKGROUND

Conventional biodetection utilizes immobilized probes to detect targets in solution. Such systems often include DNA probes to detect DNA and RNA targets, antibody probes to detect proteinaceous, carbohydrate, and small organic molecule targets, and aptamer probes to detect nucleic acid, proteinaceous, carbohydrate, and small organic molecule targets. These systems can include conventional ELISA (an enzyme-linked immunosorbent assay) that can take place in a macrowell format (e.g. a microtiter well), as well as microarray formats in which the immobilized probes can be constructed or "printed" in spots less than a hundred microns in diameter. Such methods are extensively practiced today in clinical and research applications (see, for example, U.S. Pat. No. 5,405,783 to Pirrung, et. al., U.S. Pat. No. 6,054,270 to Southern, U.S. Pat. No. 6,101,946 to Martinsky, and Weeraratna et al. "Gene Expression Profiling From Microarrays to Medicine", *J. Clin. Immunol.* 24:213 (2004), the "Packard Biochip Arrayer" from Perkin Elmer, Wellesley, Mass.).

In all of these methods, there is a binding reaction between the probe and the target, and this binding reaction is generally governed by the reaction kinetics of multiple reactant (generally bi-molecular) systems. Because the probes are immobilized, the rate of reaction is primarily determined by the concentration of the target in solution.

In many of the systems, the rate of the reaction is important. For example, in certain nucleic acid hybridizations, the reaction can require over 48 hours to complete, which can increase the cost of the analysis, or reduce the number of analyses that can take place. Furthermore, if not all of the hybridizations react to completion, then the quantitation of the analyses can be incorrect, mixing as it would the results form hybridizations at different levels of completion.

In an important application, the medical outcomes of human infections (e.g. ventilator acquired pneumonia, infectious meningitis, bacteremia, and the like) can be significantly affected by the length of time required to perform analysis of the amount and the identity of bacteria and the susceptibility of the bacteria to various antibiotics. Conventionally, the time for analysis can be 24 to 48 hours or more, during which time the condition of the patient can deteriorate as the bacteria multiply (see, for example, U.S. Pat. No. 4,778,758 to Ericsson et al., U.S. Pat. No. 3,935,073 to Waters, U.S. Pat. No. 6,043,048 to Johnston et al., and U.S. Pat. No. 4,259,442 to Gayral). Contemporary microbial analysis starts with growth of bacteria from a clinical specimen, such as sputum, blood, and the like, to high concentration in culture medium, typically on the order of 100 million organisms per milliliter. Clinical specimens may contain only a few individual organisms (e.g. in testing blood for bacteremia), and diagnostic thresholds even for high-concentration specimens are typically several thousand-fold lower than quantitative culturing detection limits.

After achieving initial bulk growth up to an adequate working concentration, the operator then performs one or more biochemical tests or growth on selective media that incorporate selective biochemical reagents. Thus the standardized current procedures require at least two sequential growth cycles, each typically requiring many hours to complete.

Additionally, drug susceptibility testing requires determination of failure to grow in selective media. Proof of the absence of growth requires additional time in culture over that which might be required of a direct indicator of cell death. It is well recognized in the medical community that such methods, attempting to prove the absence of growth, in certain circumstances produce results that do not correlate adequately with the actual results of treatment.

As a result of these and other serious deficiencies, contemporary practice fails to provide the attending physician with specific diagnostic information that the physician needs in order to select an effective drug to treat the infection within the desired time window. For example, in ventilator-associated pneumonia, clinical research has demonstrated that the odds ratio for increased morbidity and mortality after 24 hours of ineffective treatment remains at 7:1 despite a change to effective treatment. That is, unless the physician initiates effective treatment, i.e. anti-microbial drugs of a type and concentration adequate to quickly kill the infectious organisms, within substantially less than 24 hours from symptom onset, a change from ineffective to effective therapy will not significantly improve outcomes for approximately 87% of patients so treated.

Physicians are well aware of the risk of delay, and so prescribe treatment typically using a combination of broad-spectrum drugs selected empirically, based on a particular hospital or community history of microbial drug resistance or susceptibility. Clinical research has demonstrated that such empiric drug treatment is ineffective in approximately 25% to 50% of cases. Additionally, exposure of a patient to inadequate therapy not only increases the individual patient's costs and medical risks, but also increase the likelihood of fostering the emergence of resistant organisms. The latter problem increases the medical risk not only for the individual patient, but for all other individuals in the hospital and community who may later become infected with resistant organisms.

It is well recognized in the clinical research literature that prior exposure of a patient to ineffective antibiotics constitutes a significant risk factor in the later emergence of resistant organisms in that patient. For these and other reasons, it is desirable within the medical community to devise diagnostic methods that do not suffer the deficiencies of delay and inaccuracy that characterize current practices.

In theory, alternatives to microbial growth culturing include direct microbial analytical methods such as immunoassays of various kinds. Antibodies against various microbes are commercially available or may be readily developed. In fact, many different types of immunoassay are now routinely used in certain aspects of diagnosis for microbial infection.

However, none yet exist for routine bacterial identification, quantitation, and drug susceptibility testing for many serious infectious diseases.

Similarly, the rapid detection of various microbes such as bacteria, viruses, molds, and the like are also desirable for testing contamination in food and water, and in detecting the presence of potential biological warfare agents. In the food industry many products are commercially available for detecting microbial contaminants. In certain circumstances, some of these provide results in approximately 24 hours for a limited set of particular organisms. However all commercial products still require sample enrichment by means of bacterial culturing before applying the tests.

In the research literature concerning defense for biological warfare, many rapid detection devices have also been described, including some that provide results in one hour or even less. Furthermore, some such devices do not require growth cultures before being used.

However, the sensitivity of devices so far described in the literature for food testing or bio-defense falls far short of the requirements for medical diagnostics. Furthermore, these non-diagnostic applications do not require drug susceptibility testing and so the aforesaid devices do not provide it nor apparently do they lend themselves to adaptation for such a purpose.

A key limitation with these devices and with laboratory methods such as ELISA is the their dependency on the target analyte concentration. They rely on passive diffusion of target to an immuno-capture or other detection surface. The rate of occurrence of intimate probe-to-target proximity events, and hence the detection reaction rate, depends on analyte concentration in the sample solution or suspension.

In order to increase sensitivity with these devices, it is necessary to substantially increase analyte concentration. Researchers have described several strategems to increase target analyte concentration and also speed the response time for analysis of various bio-molecular and microbial targets. For example, the electrophoresis of target to the probe has been described before by Nanogen, Inc. of San Diego, Calif. (e.g. U.S. Pat. No. 5,849,486 to Heller, U.S. Pat. No. 6,017,696 to Heller, U.S. Pat. No. 6,051,380 to Sosnowski et al., U.S. Pat. No. 6,099,803 to Ackley et al., U.S. Pat. No. 6,245,508 to Heller et al., and U.S. Pat. No. 6,379,897 to Weidenhammer et al.). These systems and methods describe an addressable array of electrodes to which individual probes are attached at each individual electrode, and then which are sequentially and very rapidly reacted with probes. The reported increase in speed of reaction between the target and probes is hundreds or thousands fold. These systems, however, suffer from a number of limitations, including the need to sequentially immobilize probes on the addressable electrodes, the need to perform sequential reactions, and limitations on the detection methods that can be employed due to the higher voltages that are required for electrophoresis, precluding the use of transparent electrodes (e.g. through the use of indium tin oxide), that cannot operate at the voltages used by the Nanogen system. Furthermore, the higher voltages at which the Nanogen system operate generate oxidation products that are potentially harmful to the probes or targets, and which therefore requires the use of complex passivation surfaces to protect the probes and targets. Systems that could make use of high-speed microarray printing, which did not require complex passivation surfaces, and which did not require the electronic and other control necessary for addressable electrodes would greatly reduce the expense and complexity of such systems.

With regards to the use of immobilized probes for the detection of bacteria or other microorganisms, it is also of use to determine the antimicrobial activity of different therapeutic agents, such as antibiotics. There has been a profusion of systems that use nucleic acid or antibody probes to determine the identity of bacteria in a sample (e.g. U.S. Pat. No. 5,656,432 to Claverys et al. and U.S. Pat. No. 6,403,367 to Cheng et al.). It is difficult with these systems to determine susceptibility to antimicrobial agents, given the difficulty of finding nucleic acid or antibody markers that reliably correlate with antimicrobial resistance or behavior.

It is to the solution of these and other problems that the present invention is directed.

SUMMARY OF THE INVENTION

In light of the deficiencies of existing biodetection systems and methods, it is an objective to perform detection of biological molecules rapidly.

It is additionally an object of this invention to minimize non-specific binding that reduces the sensitivity of biodetection.

It is also an object of this invention to be able to distinguish specific from non-specific binding of a target to a surface.

It is another object of this invention to be able to identify microorganisms and to determine their susceptibility to anti-organism agents.

It is further an object of this invention to capture probes rapidly onto a surface in order to permit their detection.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

In summary, the invention comprises processes and components that can be used singly or in combination for beneficial effect. The resulting methods and devices can be used in the biodetection of a variety of different analytes within a sample, including nucleic acids, proteins, starches, lipids, and organisms and cells. In the most general forms, these entities are captured onto a substrate, where they are detected.

One aspect of the present invention involves the detection of microorganisms on a fixed substrate at more than one time. Changes in the conditions of the microorganisms at the different times can indicate their response to agents to which the microorganisms are exposed. The conditions of the bacteria can include their appearance with various stains, such as vital and mortal stains, or the appearance of growth in the microorganism, either through its size, ability to accept additional staining agent, or the occurrence of nearby "daughter" microorganisms that indicate the doubling of the microorganisms. More generally, the condition can include the identity of the microorganism, as might be indicated by a serological stain. The agents can include a variety of different antibiotics, which can be provided to the microorganisms at a number of different concentrations in order to determine properties of the bacteria such as the minimum inhibitory concentration or the minimum bacteriocidal concentration. The microorganisms can be challenged not only with constant concentrations of the agent, but the agent can also be exposed to a varying concentration that can mimic the pharmacokinetics of the agent.

It should be noted that looking at the growth and behavior of individual microorganisms has great beneficial effect, given that most current means of monitoring microorganisms requires a large number of microorganisms, and it can take an extended period to grow to sufficient numbers of microorganisms. By monitoring individual microorganisms, it is not even required for all of the individual microorganisms to show the effect, but only for a sufficient fraction so that the effect is demonstrated over a statistical background. This can allow for a very rapid test.

Another aspect of the present invention is the movement of the microorganisms or other analytes to a substrate where they can be captured. This movement can comprise a number of different forces, including electrophoresis, dielectrophoresis, centrifugation, magnetic field capture, filtration, gravity or diffusion. In many instances, the naturally occurring forces of gravity and diffusion are not strong enough for the movement to occur in a practical time for the test, and therefore the application of other artificial forces are necessary. The forces can act either directly on the analyte, or the analyte can be bound to a tag that responds to the application of the artificial force. The tag can comprise an electrostatic tag, which can include a polyelectrolyte, which then moves in an electrophoretic or dielectrophoretic field. The tag can also comprise a paramagnetic particle that responds to a magnetic field.

A further aspect of the present invention is to use a movement of the analyte with a component parallel to the surface where the analyte is captured either at the same time as or interspersed with the movement of the analyte towards the surface. This allows the analyte to become distributed along the surface, and can further allow for a larger fraction of the analyte to bind where there are multiple regions of potential binding. If these regions have different specificity for different species of analyte within the sample, then this allows the analyte to be moved from region to region until it contacts the region with the matching specificity. The movement parallel to the surface can comprise electrophoresis, filtration, or bulk flow (which can be instituted, for example, by pumps, electroosmosis, or other means).

Another aspect of the present invention is to tag the analyte with an indicator that confers detectability on the analyte. The indicator can comprise a light scattering particle, an enzyme-containing particle, a fluorophore, an upconverting phosphor, a quantum dot, or an electrochemical agent. It can also be very useful to have a tag that confers both detectability as well as movement with an artificial force (as described above).

A yet further aspect of the present invention is to remove analyte that is non-specifically bound to the surface. This washing can utilize the same forces that move the analyte towards the surface, but now applied in another direction. Such forces can include electrophoresis, dielectrophoresis, and magnetic forces. The forces can also comprise physical and chemical conditions such as pH, ionic strength, and bulk flow (laminar or otherwise).

It is also an aspect of the present invention that there be frequent monitoring of the analyte on the surface. For example, it is preferable for there to be a number of different stringencies of removal of the non-specifically bound material, so that specifically-bound material can be distinguished both from non-specifically-bound material that is less-forcefully bound as well as from material that is more-forcefully bound. The frequent monitoring can then identify specifically-bound material by looking at the stringency at which different material is removed form the surface.

An aspect of the present invention is monitoring in real-time using optical methods, which can not only identify the presence of an analyte on the surface, but also to store the location of individual analytes on the surface so that its presence can be monitored over time. The optical detection can comprise imaging detectors, such as a camera, but can also comprise a scanning laser with a light detector, that can be a photo multiplier tube. The detector can detect either the analyte itself, or as described above, an indicator that is bound to the analyte. The detector can comprise a brightfield, darkfield, phase, fluorescent, or other emitted light detector. Alternatively, the detector can comprise a surface plasmon resonance detector, wherein the surface comprises gold.

An additional aspect of the present invention relates to the use of indium tin oxide and other transparent conductive coatings which facilitate the use of optical detection. In these cases, it is necessary that the voltages that are used not exceed on the order of 2 Volts, which potential does not support electrophoresis and dielectrophoresis with many conventional buffers. It can be convenient to use redox reagents in order to support electrophoresis and dielectrophoresis. These redox reagents can be in pairs, in which the oxidation of the reducing agent gives rise to the oxidizing agent, and the reduction of the oxidizing agent gives rise to the reducing agent. Other arrangements are also possible, for example in which the oxidation product of the reducing agent oxidizes the reduction product of the oxidizing agent. It is also convenient for these reagents to be neutrally charged, so that ionic species do not interfere with the electrophoresis and dielectrophoresis.

It is yet an additional aspect of the present invention for the solutions in which electrophoresis and dielectrophoresis occur to have low ionic strength, so that the electrolytes do not reduce the effectiveness of the electrophoresis. In these cases, it is convenient for the solutions to comprise zwitterionic species both for buffering, for stabilizing the interactions between molecular species, and for providing a growth conducive environment for microorganisms.

Another aspect of the present invention is for the illumination comprises evanescent wave illumination, since this detects only that analyte that is juxtaposed with the surface, and thus analyte or indicators that are not bound can remain in the solution above the surface. The evanescent wave illumination can be coupled into the substrate beneath the surface using gratings, end-couplings, and prisms. While the evanescent wave illumination can bounce multiple times within the substrate, it is also convenient for the evanescent wave illumination to have a single bounce against the surface, which is conveniently performed with prisms which can be either detachable or permanently attached or formed with the substrate. If detachable, the interface between the prism and the substrate can be a transparent, elastic material.

A yet further aspect of the present invention is the use of sample presentation, which can comprise concentration of the analyte from a large sample volume, as well as removal of contaminants. This sample preparation can comprise centrifugation, ion exchange beads or columns, filtration, stacking electrophoresis, or forms of biochemical separation.

As described above, numerous embodiments of the present invention can be assembled from the these and other aspects of the present invention. For example, one preferred embodiment resulting from the combination of aspects of the present invention relates to a system for the quantitation of microorganisms of a first type in a solution. This system comprises a chamber comprising a first electrode and a second electrode on opposing walls of the chamber, an input port, an output port, and a fluid transport means for transporting solution into the chamber through the input port and out of the chamber through the output port. The system further comprises a first affinity component affixed to the first electrode, to which microorganisms of the first type adhere, an electrical controller that controls the potential between the first electrode and the second electrode, an automated detector that can detect the quantity of microorganisms of the first type adhered to the first affinity component, and an information controller that stores the quantity of microorganisms of the first type as determined by the detector. In the system, the solution is introduced into the chamber through the input port, a potential is applied by the controller between the first and the second electrodes sufficient to cause electrophoresis to occur between the electrodes, causing movement of microorganisms of the first type towards the first electrode to occur, such that when the microorganisms are proximate to the first affinity component, they bind to the first affinity component and their quantity is determined by the detector and stored in the information controller.

The microorganisms may comprise bacteria selected from a set of genera such as *Pseudomonas, Stenotrophomonas, Acinetobacter, Enterobacter, Escherichia, Klebsiella, Proteus, Serratia, Haemophilus, Streptococcus, Staphylococcus, Enterococcus, Mycobacterium, Neisseria*, and other human pathogens encountered in medical practice. Similarly, microorganisms may comprise fungi selected from a set of genera such as *Candida, Aspergillus*, and other human pathogens encountered in medical practice. Still other microorganisms may comprise human pathogenic viruses encountered in medical practice.

The oxidizing agent may comprise benzoquinone, a dithiol, a ketone, a ferrocinium, a ferricyanide, dihydroascorbate, oxidized glutathione, oxidized methyl viologen, or a halogen. The reducing agent may comprise dithiothreitol, dithioerythritol, a dithioalkane, a dithioalkene, a thioalkane, a thioalkene, a thiol, a hydroquinone, an alcohol, a ferrocene, a ferrocyanide, ascorbate, glutathione, methyl viologen, or a halide. Also, the reduced product of the oxidizing reagent may comprise the reducing agent.

The conductivity of the solution may be less than 100 microSiemens/cm or the conductivity of the solution may be less than 10 microSiemens/cm. The solution may comprise a zwitterionic buffer.

A concentrator may concentrate the microorganisms from a sample. The concentrator may comprise a centrifuge. The concentrator may comprise ion exchange particles.

The sample may have a higher conductivity than the solution.

The automated detector may comprise an optical detector. The optical detector may utilize optical detection methods including light scattering imaging, brightfield imaging, darkfield imaging, surface plasmon resonance, phase imaging, fluorescence imaging, upconverting phosphor imaging, quantum dot imaging, and chemiluminescence imaging.

An electrode selected from the set comprising the first electrode and second electrode may be optically transparent.

The target may be illuminated by a laser.

The detector additionally may determine the position of each microorganism adhered to the affinity component, wherein the locations of the microorganisms may be stored in the information controller along with the quantity of the microorganism at that location.

The detector may detect total amount of microorganisms of the first type through averaging of signal of a portion of the surface comprising substantially all of the microorganisms of the first type affixed to the first electrode.

The first electrode may be comprised of gold, and the detector may utilize surface plasmon resonance.

The detector may comprise a camera.

The field of view corresponding to each pixel may comprise a long axis that is less than 2 microns, or may be less than 0.5 microns.

The solution may be in bulk movement during electrophoresis.

Two periods of electrophoresis may be interspersed with a period in which the solution is in bulk movement.

The solution additionally may include microorganisms of a second type, wherein the detector can distinguish microorganisms of the first type from microorganisms of the second type.

A first tag may be comprised of a first binding agent linked to a first indicator that is detectable by the detector and a second tag may be comprised of a second binding agent linked to a second indicator that is detectable by the detector and wherein the first indicator and the second indicator are distinguishable by the detector, wherein the first binding agent binds to microorganisms of the first type, and the second binding agent binds to microorganisms of the second type, wherein the first tag and the second tag are reacted with microorganisms of the first type and microorganisms of the second type bound to the affinity component, and the detector substantially simultaneously detects the quantity of the microorganisms on the basis of the tags that are bound to the microorganisms.

A first tag may be comprised of a first binding agent linked to an indicator that is detectable by the detector and a second tag is comprised of a second binding agent linked to the indicator, wherein the first binding agent binds to microorganisms of the first type, and the second binding agent binds to microorganisms of the second type, wherein the first tag is reacted with microorganisms of the first type bound to the affinity component and the detector detects the quantity and location of the microorganisms of the first type on the basis of the tags that are bound to the microorganisms, and subsequently, the second tag is reacted with microorganisms of the second type bound to the affinity component and the detector detects the quantity and location of the microorganisms of the second type on the basis of the tags that are bound to microorganisms that are in locations that were not previously detected by the detector.

A tag may be comprised of a binding agent linked to an indicator, wherein the binding agent may comprise an antibody that binds to microorganisms of the first type.

The detector may distinguish microorganisms of the first type from microorganisms of the second type on the basis of differing electrophoretic properties of the microorganisms.

The first affinity component may comprise a polyelectrolyte. The polyelectrolyte may comprise a polycationic polymer. The polycationic polymer may comprise amine moieties. The polymer may comprise polyethyleimine or polylysine.

The solution additionally may include microorganisms of a second type, wherein microorganisms of the second type do not bind to the first affinity component. The affinity component may an antibody or an aptamer.

A second affinity component may be bound to the first electrode, to which microorganisms of the second type adhere, wherein the detector can detect the quantity of microorganisms of the second type adhered to the second affinity component, wherein the system can distinguish microorganisms of the first type from microorganisms of the second type by whether the microorganisms adhere to the first affinity component or the second affinity component.

The affinity component additionally may comprise a polymer that has intrinsically low affinity for microorganisms, wherein the polymer may comprise polyethylene glycol or polyacrylamide.

The system may additionally comprise a third electrode, co-planar with the first electrode, to which a second affinity component may bind and to which microorganisms of the second type may adhere, wherein the potential on the first electrode and the third electrode may be independently controlled by the electrical controller.

The detector may detect whether microorganisms of the first type are live or dead. The microorganisms may be stained prior to being detected by the detector with a mortal stain or the microorganisms may be stained prior to being detected by the detector with a vital stain. Subsequent to the microorganisms of the first type adhering to the first affinity component, the microorganisms may be placed in conditions conducive to growth. These conditions may comprise temperature between 34 and 40 degrees C.

The solution may be removed from the chamber via the output port and may be replaced by growth medium through the input port. Also, the growth medium may have a conductivity of less than 1 milliSiemens/cm, and the electrical controller may maintain a potential of greater than 100 mV between the first electrode and the second electrode.

Microorganisms of the first type may be detected by the detector at an initial time, and may also be detected at a second time after the microorganisms are allowed growth time sufficient for at least 10% of the microorganisms to double, wherein differences in the detected microorganisms of the first type at the two may provide evidence of the viability of the microorganisms of the first type in the growth conditions. Also, an anti-microorganisms agent may be added to the growth medium during the growth time. The detector may detect if microorganisms of the first type are live or dead in response to the anti-microorganism agent, wherein prior to detection by the detector the microorganisms are stained with a stain selected from the set consisting of mortal stain and vital stain. The anti-microorganism agent may comprise individual agents or combinations of agents selected from antibiotic families such as cephalosporins, penicillins, carbapenems, monobactams, other novel beta-lactam antibiotics, beta-lactamase inhibitors, fluoroquinolones, macrolides, ketolides, glycopeptides, aminoglycosides, fluoroquinolones, rifampin, and other families, including novel agents, used as antibiotics in clinical practice or in research. Also, the concentration of the anti-microorganism agent may be changed over time to reflect the pharmacokinetics of the anti-microorganism agent in animal tissue.

The microorganisms may be reacted with a surplus of microorganism surface binding reactants at a first time period, after which the reactants are subsequently removed, and wherein at a second time period the microorganisms may be reacted with a surplus of microorganism surface binding molecules modified by an indicator so as to be detectable by the detector, wherein the detection of the indicator by the detector indicates the growth of the microorganisms.

The solution additionally may comprise a contaminant that binds to the first affinity component along with the microorganisms of the first type, wherein a condition is applied to the first affinity component which releases the contaminant without releasing the microorganism, whereas the contaminant is removed by application of the condition. The condition may comprise temperature, magnetic field strength, electrophoretic force, dielectrophoretic force, shear fluid flow, ionic strength, pH, non-ionic surfactant concentration, ionic surfactant concentration, or competitor concentration. The solution additionally may comprise a contaminant which binds to the first affinity component along with the microorganisms of the first type, wherein a condition is applied to the first affinity component which releases the microorganisms without releasing the contaminant, whereas the microorganisms may be subsequently bound to a second affinity component affixed to the first electrode. The condition may comprise temperature, magnetic field strength, electrophoretic force, dielectrophoretic force, shear fluid flow, ionic strength, pH, non-ionic surfactant concentration, ionic surfactant concentration, or competitor concentration.

The microorganisms of the first type may be concentrated in the solution prior to being bound to the first affinity component, wherein the microorganisms are present in a first salt buffer of relatively low ionic strength, and the first salt buffer is proximal to a second salt buffer of relatively higher ionic strength and the first salt buffer and the second salt buffer adjoin at an interface, and wherein a first concentration electrode is located proximal to the interface and a second concentration electrode is located distal to the interface, wherein the placement of a potential between the first concentration electrode and the second concentration electrode causes the microorganisms to migrate through the first salt buffer by electrophoresis and their migration is reduced more than X fold upon meeting the interface. The second concentration electrode may comprise the first electrode. Also, the interface may be located substantially at the input port. The ratio of conductivity between the first salt buffer and the second salt buffer may be less than 1:50.

BRIEF DESCRIPTION OF THE DRAWINGS

FIG. 1 is a schematic diagram of a biodetection system that utilizes a probe having affinity for a target.

FIG. 2A, a schematic diagram of a biodetection system taking place in which different probes 116 are placed in an array of locations on a substrate.

FIG. 2B is a side-view through the array of FIG. 2A.

FIG. 3 is a perspective diagram of an electrophoretically-enhanced incubation system.

FIG. 6 is a schematic diagram of an electrophoretic tag in a sandwich configuration.

FIGS. 7A through F are schematic diagrams of electrophoretic tags, showing differing arrangements of components to provide similar functionality.

FIG. 12C is a graph of the potential difference between the electrodes E2 and the four as they vary with time, arranged alternatively to that in FIG. 12B.

FIG. 12D is a graph of potential differences between spatially displaced electrodes, such the electric field changes not only magnitude but also in direction.

FIG. 16A is a schematic block diagram of a reaction involving both vertical forces and horizontal forces so as to accelerate the reaction of a tagged target with the probe 116.

FIG. 19A is a perspective diagram of a microtiter plate with a set of electrodes 570 and shafts 552.

FIG. 19B is a perspective view of a top plate comprising access ports.

FIG. 23A is a cross-sectional schematic of an embodiment of the present invention in which a prism on the top surface is used to introduce light into the slide waveguide.

FIG. 23B is a cross-sectional schematic of a prism on the top surface of a slide, in which light is internally reflected within the prism prior to introduction of the light into the slide waveguide.

FIG. 24A is a cross-section schematic of the prism arrangement of FIG. 3, extended so that the disposition of the distal parallel raypaths can be seen.

FIG. 24B is the cross-sectional schematic of FIG. 4A, modified by the use of convergent illumination instead of collimated illumination.

FIG. 25A is a schematic cross-section of an end-illuminated thin-film waveguide integrated with a slide.

FIG. 25B is a schematic top view of the coupler and the slide of FIG. 5A.

FIG. 26A is a schematic cross-section of evanescent illumination of a region without use of a waveguide.

FIG. 26B is a schematic cross-section of evanescent illumination according to FIG. 6A, in which the prism has a window through which the detector detects reporters on the top surface of the slide.

FIG. 27A is a schematic cross-section of light coupling with a prism using a flexible coupler.

FIG. 27B is a side view schematic of a prism with a curved face coupler.

FIG. 31 is a block flow diagram of the process for determining the identity, number and antibiotic sensitivity of bacteria in a sample.

FIG. 32A is a top schematic diagram of a bacterial detection cell.

FIG. 32B is a side view schematic diagram of the bacterial detection cell of FIG. 32A through the cross-section X.

FIG. 32C is a side view schematic diagram of the bacterial detection cell of FIG. 32B with the use of addressable electrodes.

FIGS. 34A-D are side-view schematic diagrams of electrophoretic transport to the detection surfaces.

FIGS. 35A-D are side-view schematic diagrams of a chamber in which contaminating material is distinguished on the basis of its behavior under electrophoretic fields.

FIGS. 36A-E are side-view schematic diagrams of detection of multiple bacteria on a non-specific surface.

FIGS. 41A-B are schematic cross-sections of a detection system using multiple forces to effect separation of the bacterial sample.

BEST MODE FOR CARRYING OUT THE INVENTION

Biodetection Background

Figure 4A:
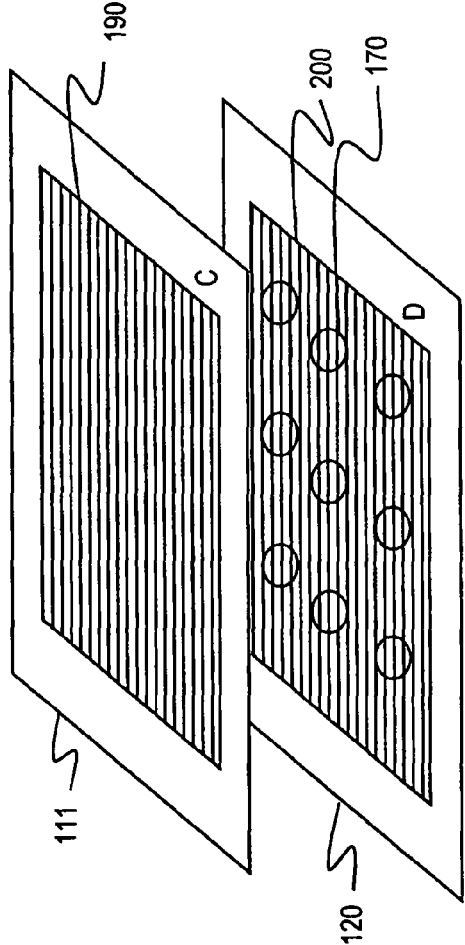
FIG. 4A is a perspective diagram of a biodetection system wherein a single probe electrode underlies multiple probe locations which are placed into an array.

FIG. 1 is a schematic diagram of a biodetection system 100 that utilizes a probe 116 having affinity for a target 114. The probe 116 is affixed to a solid substrate 120 by a probe linker 118. The probe linker 118 will generally comprise a coating that further serves to reduce the adventitious binding of target molecules to the substrate 120. The target 114 is connected via a target linker 112 to a tag 110, which can be detected by a detector, not shown.

The target 114 can comprise a variety of biomolecules, including nucleic acids, proteins, starches, lipids, hormones, and more. Furthermore, the target 114 can comprise, as will be discussed below in greater detail, whole organisms or organelles, including bacteria, fungi, viruses, mycoplasmas, cell fractions (mitochondria, nuclei), animal or plant cells, and other organisms. In each case, the probe 116 will match the target 114, and itself can comprise nucleic acids (both for hybridization and as aptamers), proteins, carbohydrates, and can also include whole organisms and organelles as described above. Indeed, in most cases, wherever one has a target-probe pair, the constituents can generally be switched so that the target acts as a probe, and the probe as a target, on the basis of their affinity for each other.

In operation, the target 114, which is connected to the tag 110, is introduced into solution that is in contact with the probe 116. Because of the molecular affinity of the probe 116 for the target 114, the target 114 binds to the probe 116. Because the tag 110 is attached to the target 114, the presence of the tag 110 in proximity to the surface of the substrate 120 indicates the presence of the target 114. By determining the amount of the tag 110, the amount of the target 114 can be estimated.

Alternatively, the tag 110, instead of being bound directly to the target 114, can be attached via a linker to a second molecule with affinity for the target 114. After incubation with the probe 116 and the target 114, a "sandwich" is formed in which the target 114 associates with both the probe 116 and the tag 110.

One of the difficulties of the systems according to FIG. 1 is the time that it takes for the incubation of the target 114 and the probe 116 to come to dynamic completion. Consider, for example, a common microplate laboratory format in which different probes are placed in a grid of wells arranged in an eight column by twelve row well format (as will be described in greater detail below). The plate well layout is defined by industry standards and the wells are typically on the order of 9 mm in diameter. The binding of the target to the probe requires the two species to be in close proximity measured on a scale of Angstroms. In a typical microplate assay diffusion and sometimes convection are utilized to increase the probability that the two species come in close proximity to complex at the surface. This strategy generates significant signal, at hours long incubation, with typical conventional detection methodologies at pg/ml concentrations of a 50 kd model protein. However at sub or low pg/ml concentrations, the signal generation is limited by the mass transport of analyte to surface, so that unreasonable reaction times measured in days are required for the assay to reach completion.

Furthermore, transport of target 114 to probe 116 is further exacerbated in a micrometer scale array of probes (i.e. microarray format). FIG. 2A, a schematic diagram of a biodetection system taking place in which different probes 116 are placed in an array 140 of locations 130 on a substrate 120. Each location 130 is typically on the order of 50 microns to 500 microns in diameter, and with an array comprising ten to tens of thousands of locations 130, a typical side-to-side dimension for the array 140 can be millimeters or even centimeters. The binding of the target 114 to the probe 116 requires that the two species be in close proximity measured in Angstroms. Given that the passive diffusion of large biological macromolecules is low (e.g. measured in nanometers per second)), the lateral movement of the target 114 to the probe 116 can take on the order of tens of hours, unless active assistance is provided.

Even with assisted movement of the molecules laterally, the vertical scale of the incubation can frustrate the target 114 to probe 116 binding. Consider FIG. 2B, a side-view through the array 140 of FIG. 2A. A cover 111 comprises the top of the incubation cell, and if the target 114 is near the top of the incubation chamber (delimited by the substrate 120 and the cover 111), the vertical dimension is still large by molecular standards. Consider that the smallest vertical thickness used in conventional incubations is typically about 50 microns. Given that the target 111 and the probe 116 need to be within a few Angstroms, in general, in order to bind to one another, the vertical scale is 10,000 times this size. In the best of cases, the target 114 would be limited in its movement to a very small volume in the vicinity of the immobilized probe 116 to increase its apparent concentration.

A prior art embodiment of a means to overcome this problem is provided in FIG. 3, a perspective diagram of an electrophoretically-enhanced incubation system. In this case, the different probes 116 are affixed directly onto electrically conductive electrodes 150. These electrodes 150 are independently voltage-biased relative to a reference electrode 140 so as to cause a current within the incubation chamber, in which target 114 molecules migrate to the electrode 150. Consider, for example, that electrode 150 A is initially voltage biased to attract the target 114. Because of the immediate proximity of the target 114 and the immobilized probe 116 at the electrode 150, the binding between the two species occurs very rapidly—on the order of seconds to tens of seconds. The voltage on the electrode 150 A is then made neutral or opposite to its previous bias, and the electrode 150 B is then biased. In this case, the target 114 molecules would migrate to the second electrode 150 B so as to allow the interaction of the target 114 with the probe immobilized in the second location.

This embodiment has been extensively used by Nanogen (San Diego, Calif.), and the prior art teachings are specified in a series of patents, including U.S. Pat. No. 5,849,486 and U.S. Pat. No. 6,017,696. There are a number of limitations of this embodiment, however. For example, the area covered by the probe 116 and the respective electrode 150 must be exactly coincident. In general, this means that the probes 116 are immobilized sequentially using movement of the probes 116 analogous to the movement of the target 114 during the incubation. Furthermore, each probe 116 electrode 150 must establish its own electrical connection to a power controller, which requires both sophisticated manufacturing and power control.

Arrangement of Components

Some embodiments of the present invention comprise the application of electrophoretic forces on the target 114 wherein the electrodes involved in such forces are not necessarily coincident with the locations on which the probe 116 is attached. The application of electrophoretic force can be according to a number of embodiments, of which two are presented for discussion purposes: firstly, in which the electrodes do not underlie the probe locations 116 whatsoever, and wherein the electrophoretic forces are primarily lateral to the surface of the substrate 120, and secondly, in which a single electrode underlies a plurality of probe 116 locations. It should be noted that the structural arrangement of the probe locations and the electrodes giving rise to the electrophoretic forces will be first considered, along with various components optimized for use with the present invention, and thereafter the operation of the various components in concert will be described. It should also be noted that dielectrophoresis rather than electrophoresis can be used to move targets (or tags that are attached to targets) that are large and electrostatically polarizable. These methods generally require the use of electrodes that are shaped either in two or three dimensions so as to create electrical or electrophoretic fields that are non-uniform. A description of the use of these dielectrophoretic electrodes is presented in G. H. Markx and R. Pethig, Dielectrophoretic Separation of Cells: Continuous Separation. Biotechnol. Bioeng. 45, 337-343 (1995) and G. H. Markx, Y. Huang, X.-F. Zhou and R. Pethig, Dielectrophoretic characterization and separation of micro-organisms, Microbiology, 140, 585-591 (1994).

Arrangement Involving a Single Electrode Underlying Multiple Probe Locations

FIG. 4A is a perspective diagram of a biodetection cell wherein a single probe electrode 200 underlies multiple probe locations 170 which are placed into an array 180. The walls of the cell are not placed in the diagram, and will generally comprise gasket material to form a water tight seal. A reference electrode 190 is physically placed preferably above the probe electrode 200 and of roughly similar size to the probe electrode 200, so that the electric field between the two electrodes is substantially uniform. However, it is also within the spirit of the present invention for the reference electrode 200 to have various shapes and positions that allow for similar or even lesser uniformity. In general, the electrodes are roughly parallel to one another, so that the electrophoretic fields that are generated are roughly perpendicular to the surface of the probe electrode 200, and give rise to even deposition of the targets onto the probe locations 170.

This arrangement of the probe electrode 200 and the probe locations 170 allow for standard methods of placement of probes on the electrode surface using contact or non-contact (e.g. pin or piezoelectric) spotters. Furthermore, the association of the target 114 with the probe 116 can be performed in parallel with all of the different probe locations 170, rather than serially as performed with the prior art.

Arrangement Involving Electrodes not Underlying Probe Locations

Figure 4B:
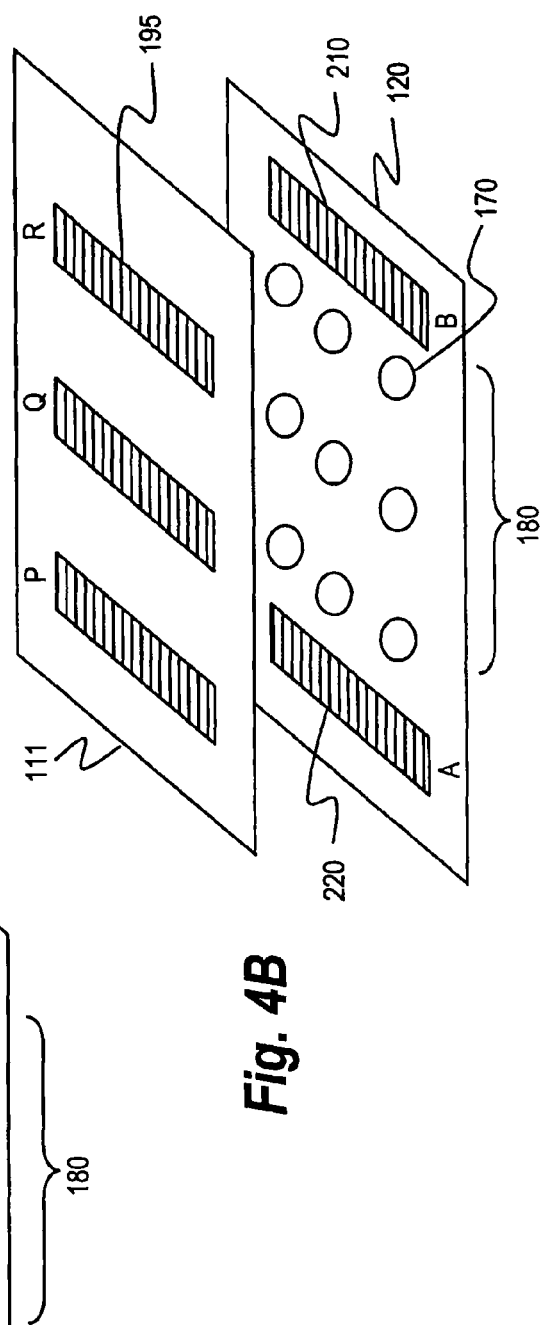
FIG. 4B is a perspective diagram of a biotection system wherein the electrodes do not underlie the probe locations.

An alternative arrangement is shown in FIG. 4B, a perspective diagram of a biodetection cell wherein the electrodes do not underlie the probe locations 170. In this case, the probes 116 are placed in probe locations 170 arranged in an array 180. A first electrode 210 and a second electrode 220 are lateral to the array 180, and sit underneath an array of partial reference electrodes 195, labeled in this figure P, Q, and R. The number and type of partial reference electrodes 195 can be varied, and the goal of the placement of the first electrode 210, the second electrode 220, and the partial reference electrodes 195, is to manage the strength and topology of the electric fields by adjusting the relative voltages of the electrodes. For instance, placing the second electrode 220 and the partial reference electrodes 195 P, Q and R at a negative bias, and the first electrode 210 at a relatively positive bias will cause a largely horizontal electric field across the surface of the array 180. The need for the multiple partial reference electrodes 195 is due to the "shorting" of the electric field that would occur with a large, continuous electrode, making it difficult to maintain an electric field across a larger electrode.

Figure 5:
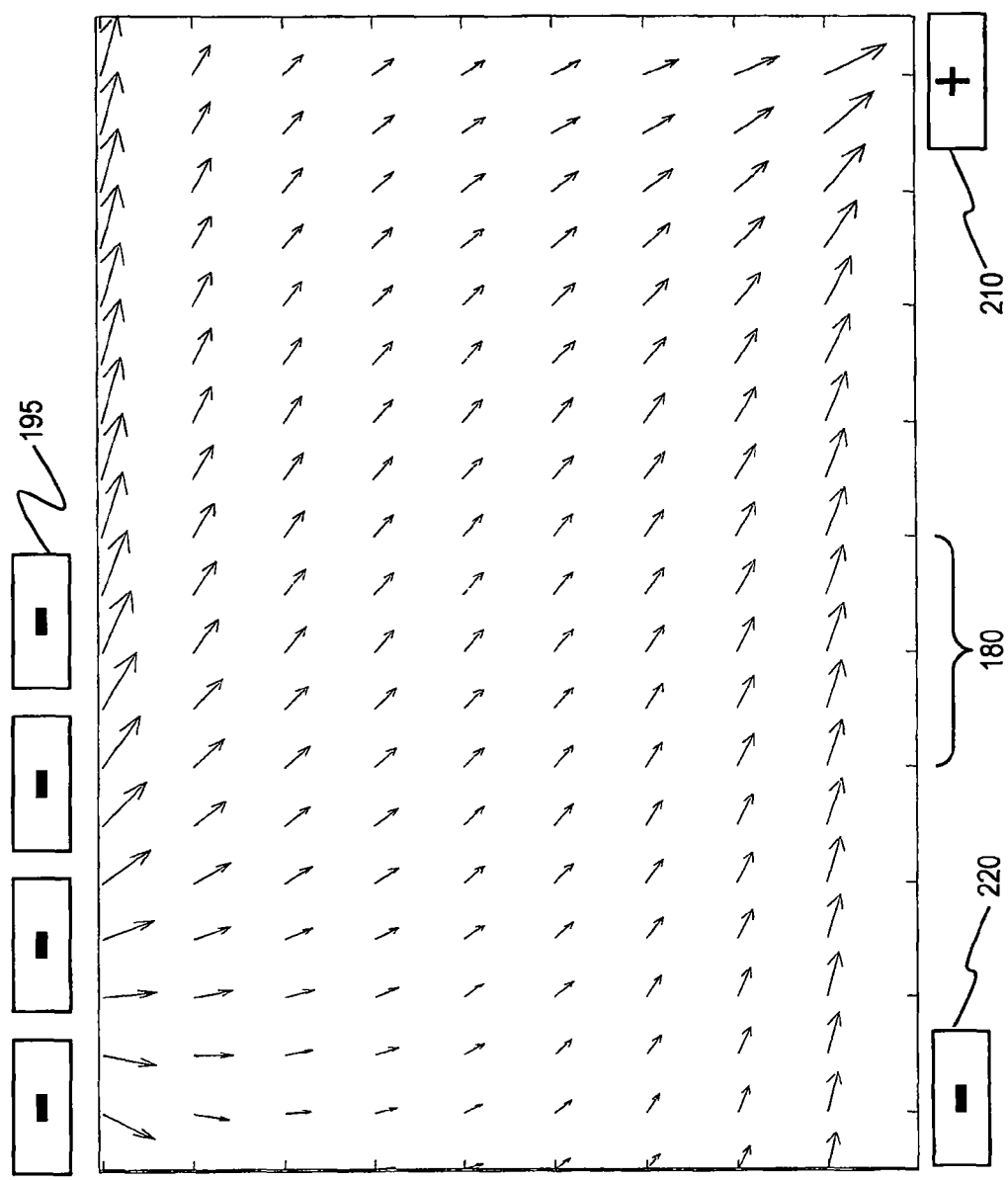
FIG. 5 is a diagram of electric field strengths from a first electrode, a second electrode, and a set of partial reference electrodes.

FIG. 5 is a diagram of electric field strengths from a first electrode 210, a second electrode 220, and a set of partial reference electrodes 195. The second electrode 220 and the partial electrodes 195 have a negative bias, and the first electrode 210 has a relatively positive bias. As can be seen, the vertical component of the electric field at the location of the array 180 is relatively constant with a downwards component. By adjusting the relative strengths of the voltage bias at the different electrodes, a variety of different electric field topologies can be arranged for purposes that will be described below.

Electrophoretic Tags

Most biological molecules have associated electrostatic charge, which can be adjusted by the pH of the solution in which the molecules are maintained. For nucleic acids, the charge is generally negative and determined by the phosphate backbone, and is furthermore directly related to the length of the nucleic acid. For the purposes of the present invention, this has certain disadvantages, since the size of the target 114 molecules can vary. Consider an application in which RNA molecules associated with different genes will be measured. In such case, the length of RNA associated with each gene will vary according to the length of the gene. Furthermore, RNA from higher organisms is poly-adenylated, and the length of the "polyA" tail varies from RNA to RNA. This means that it is difficult to provide a relatively constant force across all of the different RNAs, or even across RNAs associated with the same gene.

One method of overcoming this difficulty is to place an "electrophoretic tag" on each molecule. The electrostatic charge of this tag will be large compared with the charge of the polyA tail variation, and furthermore can be substantial even with regards to the overall charge of the RNA molecules. In this case, the variations of charge within RNAs associated with a particular gene due to polyA tails will be fractionally insignificant, and the charge differences between RNAs associated with different genes will be fractionally small, even if the RNAs are of significantly different size, as long as the charge of the electrophoretic tag is large enough.

FIG. 6 is a schematic diagram of an electrophoretic tag 270 in a sandwich configuration. The electrophoretic tag 270 is generally comprised of three functional components (or fewer components, of which one or more components can comprise multiple functions). A tag binding component 272 binds the tag 270 to the target 114 through a means that can be either specific to the specific target 114 (e.g. a specific antibody or aptamer), or which can be common to a large number of targets 114 (e.g. polyT, which will bind to polyA regions of mRNAs). An indicator component 290 is detectable by a detector. An electrostatic component 280 comprises a charged material, wherein the charge is large and consistent from tag to tag. While the magnitude of the electrostatic charge of the electrostatic component 280 can be broad within the spirit of the present invention, it is preferable for the charge to be at least 1,000 net charges, and even more preferable for the charge to be at least 5,000 net charges, and even more preferable for the charge to be at least 10,000 net charges. Furthermore, it is preferable for the charge on the electrophoretic tag 270 to be of the same polarity as the charge on the target 114. For example, for nucleic acid targets 114, it is preferable for the electrostatic component 280 to be negatively charged.

It should be noted that at certain times, it can be convenient to independently form an association between the electrophoretic tag 270 and the target 114. That is, instead of associating the target 114 with the probe 116, and then associating the tag 270 with the target 114, the tag 270 and the target 114 are first associated, where the associated component is called a tagged target 275.

The structure of the electrophoretic tags 270 can be quite varied within the spirit of the present invention. FIGS. 11A through F are schematic diagrams of electrophoretic tags 170, showing differing arrangements of components to provide functionality within the scope of the present invention.

Figure 7B:
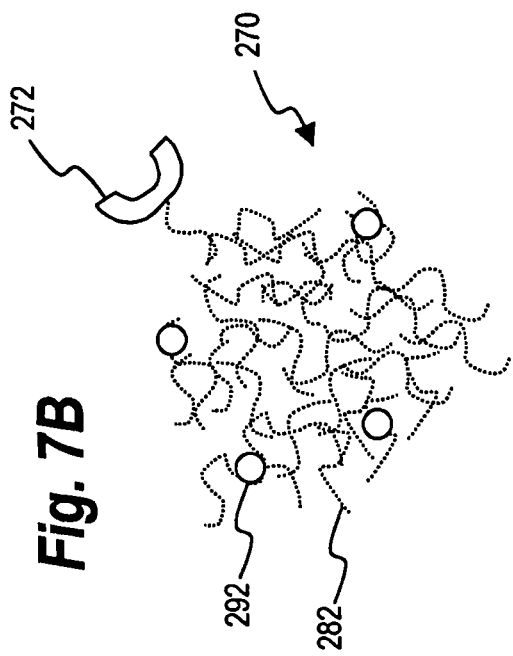
Figure 7D:
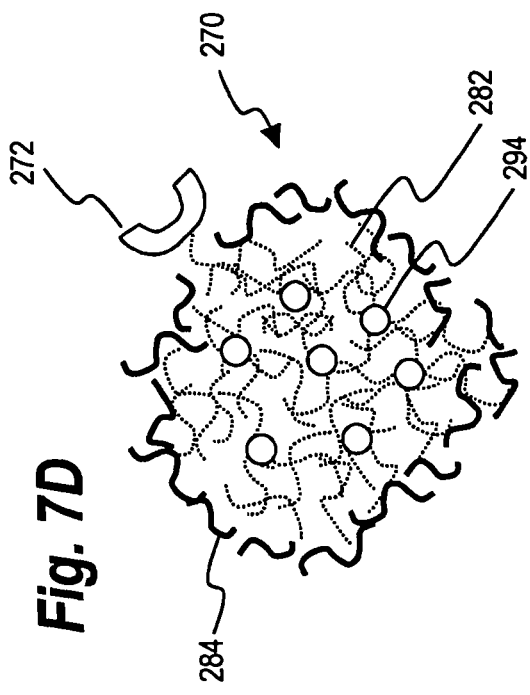
Figure 7A:
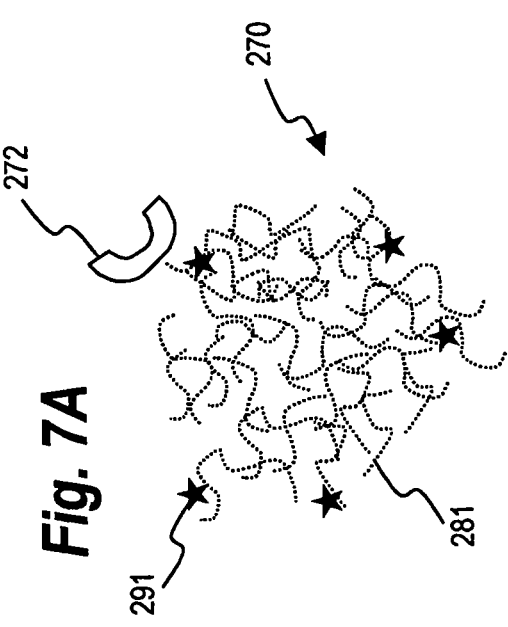

FIG. 7A is a schematic diagram of an electrophoretic tag comprised of cross-linked DNA 281 as the electrostatic component 280 and fluorescent dyes 291 as the indicator component 290. The DNA is best largely double-stranded so that it interferes less with nucleic acid targets 114 and probes 116, and is conveniently comprised of regions of double stranded DNA with single-stranded tails that interact with one another. Furthermore, it is preferable for the interacting regions to be chemically bonded to provide integrity to the tag 270 under a variety of different physical and chemical conditions. An example of this form of electrophoretic tag 270 is 3DNA (Genisphere, Hatfield, Pa.), which is a dendromeric, cross-linked DNA structure which can be bound to both fluorescent dyes as well as to a binding component 272. The binding component 272 is conveniently an antibody with specificity against the target 114, an avidin molecule with specificity to a biotin moiety attached to the target 114 (or conversely, a biotin moiety with specificity against an avidin molecule attached to the target 114), an aptamer selected with specificity to a target, a nucleic acid complementary to a nucleic acid target 114, or other specific binding components. It should be noted that for use with messenger RNA targets, the binding component 272 is conveniently a polyT single-stranded DNA oligomer, which will bind to the polyA tails of the RNA, or alternatively a polyT Locked Nucleic Acid (Exiqon, of Vedbaek, Denmark) which has higher affinity for polyA than the unmodified polyT.

It should be noted that in many cases, the binding energy between the binding component 272 and the target 114 will be chosen to be greater than that of the binding energy between the target 114 and the probe 116. This can be arranged by either making the binding of the target 114 to the probe 116 weaker, or more preferably, making the binding of the binding component 272 to the target 114 stronger. One method to ensure this is to create covalent links between the target 114 and the binding component 272. This can entail, for example, the incorporation of BrdU into the polyT linker of the binding component 272, which can be photo-activated to cause covalent links. In the case of proteins, if the binding component 272 is comprised of a protein (e.g. an antibody), the protein can be modified with photo-activatable cross-linking reagents such as aryl azides (e.g. phenylazide, hydroxyphenylazide, and nitrophenylazide) and after the target 114 is allowed to associate with the binding component 272, light can be used to stimulate cross-linking. The unreacted cross-linking reagent can then be consumed using a deactivation reagent, which in the case of aryl azides can include reducing agents such as thiol-containing reagents.

While in most cases, the binding energy being discriminated is that between the probe 116 and the target 114, it is also within the spirit of the present invention for the discrimination to take place regarding the binding energy between the target 114 and the tag binding component 272. Consider, for example, an antibody sandwich assay, in which both the probe 116 and the tag binding component 272 comprise antibodies or parts of antibodies. In that case, it is equally useful for the weaker antibody-ligand binding energy—that is, the binding energy that is being discriminated in the assay—to be with either antibody. This simplifies the design of such an assay, inasmuch as it is unnecessary to determine which of the antibody components to be used in the sandwich assay has a stronger affinity for the target 114.

This ability to utilize both target 114-probe 116 binding energy as well as target 114-tag binding component 272 is equally applicable to nucleic acids as well. Thus, the methods of the present invention will be effective even if the target 114-tag binding component 272 association is weaker than that of the target 114 to the probe 116.

Furthermore, this method still applies even if the association between the target 114 and the tag binding component is not a specific one-to-one association. Consider, for example, the case where the tag binding component 272 comprises a fixed length polyT oligonucleotide, which may be comprised of Locked Nucleic Acid nucleotides, which associates with the polyadenylated "tails" of messenger RNA. The specific association of probes 116 with their targets 114 can provide the spatial specificity of binding of the targets 114—that is, where in the array 180 that the target 114 will bind—whereas the binding energy between the target 114 and the tag binding component 272 can provide a consistent binding energy that can be discriminated by the system.

It is also within the spirit of the present invention for covalent cross-linking to occur between both target 114 and probe 116, as well as between target 114 and tag binding component 272, so as to make a continuously covalent linkage between the substrate and the indicator component 290. That is, given the incorporation of proper activatable cross-linking components into the probe 116 (see above for a discussion of activatable cross-linking reagents), after the reaction between the target 114 and the probe 116, activation of the cross-linking moiety bound to the probe 116 can be performed, such that covalent cross-links between the probe 116 and the target 114 are formed. Such reaction can occur as well between the target 114 and the tag binding component 272, as described above. In such cases, the binding energy holding the indicator component 290 to the substrate is very large, so that specific binding can be easily distinguished by its large binding force.

FIG. 7B is a schematic diagram of an electrophoretic tag comprised of an ionic polymer 282 as the electrostatic component 280 and up-converting phosphors 292 as the indicator component 290. The ionic polymer can be conveniently linear or branched polyanion, with the ionic groups comprising either carboxyl groups (if the pH of the buffer at which the tag 270 is to be used is near or above the pK of the carboxyl group), or can also be a polyphosphate, polysulfate (e.g. polyvinyl sulfonate, polystyrene sulfonate, sulfated starches, or dextran sulfonate) or other polymer containing an inorganic acid moiety, which can comprise phosphates, quaternary amines, tertiary amines, secondary amines, primary amines, sulfates, nitrates, and carboxylates. These ionic polymers can be created via de novo synthesis from monomeric reagents, or can alternatively be generated by modifications of well-characterized non-ionic or weakly-ionic polymers such as polyvinyl alcohol or various starches. It should be noted that the highly ionic polymers will be highly attracted to highly ionic species of the opposite polarity, and that therefore the electrostatic component 280 needs to be tested to check for non-specific binding to the substrate 120 or other species in the analyte solution that can give rise to high backgrounds in the detection assays.

Up-converting phosphors 292 are particles that convert lower frequency light into higher frequency light (see Orasure Technologies, Inc. of Bethlehem, Pa.), and are convenient to use due to the few natural compounds having this property, leading to generally low background in detection assays.

Figure 7C:
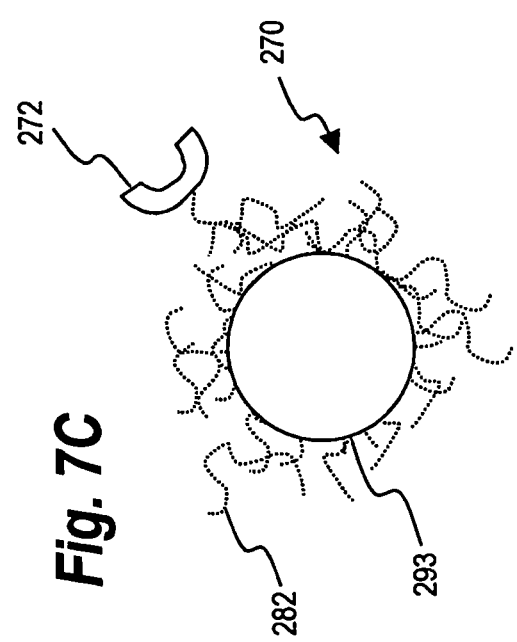

FIG. 7C is a schematic diagram of an electrophoretic tag comprised of an ionic polymer 282 as the electrostatic component 280 and a direct visualization particle 293 as the indicator component 290. The particle can be metallic (e.g. gold), ceramic, colored glass, or other opaque or largely opaque material and is conveniently at least 250 nanometers, and more preferably at least 500 nanometers, so that it is visible via light microscopy. The ionic polymer 282 can be comprised of the same materials as the ionic polymer 282 of FIG. 7B.

FIG. 7D is a schematic diagram of an electrophoretic tag comprised of an ionic polymer 282 in conjunction with a low nonspecific binding polymer 284 as the electrostatic component 280 and a light scattering particle 294 as the indicator component 290 of FIG. 6. The ionic polymer 282 is similar to that shown in FIG. 7B. If this polymer 282 exhibits high nonspecific binding, it can be coated with a second polymer 284, such as a form of polyethylene glycol or polyacrylamide, which exhibit very low nonspecific binding. This coating will in general involve covalent bonding between the ionic polymer 282 and the low nonspecific binding polymer 284.

The light scattering particle 294 can comprise a variety of materials that scatter light, including metals, ceramics and glass. The size of these particles is preferably smaller than 500 nm, and even more preferably smaller than 200 nm and even more preferably smaller than 50 nm. An example of such a light scattering particle 294 is resonance light scattering particles by Genicon (San Diego, Calif.).

FIG. 7E is a schematic diagram of an electrophoretic tag comprised of a double-stranded DNA molecule 285 as the electrostatic component 280 and a quantum dot 295 as the indicator component 290. In this case, the electrostatic component 280 is a linear, rather than a branched or cross-linked DNA molecule. The indicator component 290 and the binding component 272 are connected on either end of the DNA molecule 285. The structure can be assembled by attaching the binding component 272 to one end of the single stranded DNA molecule, and then attaching the indicator component 290 to a complementary single stranded DNA molecule. As the two complementary single stranded DNA molecules hybridize with one another, the desired structure is generated. It should be noted that the double stranded molecule 285 can be replaced with a single stranded DNA molecule or with a linear polyionic polymer within the spirit of the present invention.

Quantum dots 295 function much in the same way as fluorescent dyes, but with a considerably larger shift between the excitation and admission frequencies. This large shift allows the use of higher efficiency optical filters that reduce the amount of background noise in a detection assay. An example of quantum dots 295 is the nanocrystals produced by Quantum Dot Corp. (Hayward, Calif.).

FIG. 7F is a schematic diagram of an electrophoretic tag 270 comprised of a linker component 274 linking double-stranded DNA molecule 285 as the electrostatic component 280 and a quantum dot 295 as the indicator component 290. The linker component 274 comprises attachment sites for three components: the binding component 272, the indicator component 290, and the electrostatic component 280. The linker component 274 will generally have three different binding groups which allow for selective binding of each group by the three components separately. An example of such a linker 274 includes the amino acid cysteine, which has carboxyl, amino and thiol components of separable reactivities for synthesis, or serine, which has carboxyl, amino, and hydroxyl components. There are a number of functional groups that can be used on the linker in order to allow it to interact with the components 272, 290 and 280. These functional groups can comprise, for example, thiols, aryl azides, alcohols, amines, epoxies, n-hydroxy-succinimde, biotin, avidin, or other chemically active groups or groups with high affinities (e.g. avidin and biotin).

It should be understood that in the preceding discussion of an electrophoretic tag 270, the electrostatic component 280 and the indicator component 290 from the different examples can be combined separately to create tags of useful benefit. It is further understood that the electrostatic components 280 and indicator components 290 discussed are not exhaustive, and any chemical or physical component providing similar function is within the present invention. For instance, the indicator component 290 can comprise many materials, such as (and including modes of detection discussed above) enzyme indicators, chemiluminescent indicators, electrochemical (e.g. redox) indicators, radioactive indicators, and others types that are used in microarray, ELISA, and other biochemical and chemical assays, upconverting phosphors, fluorophores, quantum dots, light scattering particles, light absorbing particles (e.g. colored particles), or phase contrast particles (i.e. to confer index of refraction differences that can be visualized in a phase contrast microscope or by surface plasmon resonance).

Many of these indicators can be used with optical detection means which is matched to that of the indicator. Thus, for fluorophores, quantum dots, and upconverting phosphors, paired excitation illumination (e.g. laser excitation or broad-spectrum illuminators with bandpass filters) and emission-specific detectors (e.g. bandpass filtered) are utilized along with proper imagers (e.g. cameras with or without magnification optics). Light scattering particles will often use oblique incident illumination (including standard darkfield condensers) or evanescent illumination, or may alternatively use phase contrast optics, since particles with sufficient difference in refractive index to give rise to phase optical effects will also give rise to light scattering. In addition, the phase contrast particles will also generally be visible in surface plasmon resonance. Phase microscopy can be used for phase contrast particles, and light absorbing particles and enzymatic reactions can be used in both phase contrast microscopy and brightfield imaging (e.g. with microscopic imaging or other forms of magnification). Chemiluminescence can be detected with proper magnification and detectors arranged to have the proper receptivity to the chemiluminescent signal. The descriptions above are not exhaustive, and other combinations of indicator and detector are within the spirit of the present invention.

It should also be noted that is preferable that there be only a single binding component 272 for each electrophoretic tag 270 so that each target molecule 114 is associated with only a single electrophoretic tag 270. This can be handled by associating targets 114 with a large numerical excess of electrostatic tags 270 such that, on average, most electrophoretic tags 270 will be unassociated with target, and that most tagged targets 275 will have only a single target 114.

The amount of charge on the electrophoretic tag 270 should generally be comparable to or greater than the charge on the targets 114. For proteins, the charge may not be large, those nucleic acids in general have approximately one charge per nucleotide, and the size of the targets can be hundreds to thousands of nucleotides (in a small number of cases tens of thousands of nucleotides or more). While bacteria and other organism targets can have a large charge, there are also generally a number of places for the tag 270 to bind, and so the sum of many tags 270 will often exceed the charge on the organism surface. In general, it is preferable for the electrophoretic tag to have an average absolute net charge of greater than 1000, and even more preferably greater than 5000, and most preferably greater than 20000.

It should further be understood that in most applications of the present invention the use of an electrophoretic tag 270 is not a requirement. That is, most targets 114 intrinsically comprise an electrostatic charge that allows the target's 114 movement in electrostatic or electrophoretic fields, and for which targets 114 the tags do not require an electrostatic component. It is within the spirit of the present invention, where the term electrophoretic tag 270 is used in this description, that a non-electrophoretic tag can be used in conjunction with the naturally occurring electrostatic charge on the target 114. Furthermore, the charge of these molecules can often be adjusted by pH, and it can be convenient to adjust the pH at which electrophoresis occurs to alter the electrostatic charge on the target 114.

Competitive Assay Formats

The assay formats described above related primarily to sandwich assay formats. However, in the case of very small targets 114, such as hormones or drugs of substance abuse, it is difficult to bind to find reagents that allow simultaneous, high-affinity binding of both a probe 116 and a tag binding component 272. Without two such binding reagents, the sandwich assay is performed with difficulty.

An alternative is a competitive assay, in which a specific binding probe 116 to the target 114 is immobilized, as before, on the substrate. Added to the analyte containing the target 114 is a competitor, which binds to the probe 116 with similar affinity to that of the target 114, and to which is covalently bound an indicator 290. In the absence of target 114 in the analyte, a given amount of the competitor will bind to the probe 116. However, if the analyte contains the target 114, the binding of the competitor will be reduced. Thus, in the competitor assay, the target 114 is not directly detected, but rather its abundance is evidenced by the reduced binding of the competitor.

The competitive assay format is used advantageously in the present invention, given the requirements for consistent and reproducible binding, which is improved by the reaction acceleration of the present invention. Furthermore, because the present invention uses relatively short reactions, as well as rapid washing, relatively low affinity probes 116 can be used that would otherwise lead to loss of signal with conventional washing and detection methods. Note that this latter advantage accrues not only to competitive assay formats, but sandwich assay formats, as well.

Attachment of Probes

As mentioned above, the probe 116 is attached to the substrate 120 through a linker 118. This linker 118 conveniently comprises a coating with functional groups, wherein the functional groups permit the binding of the probes 116. Also, the coating preferably has low non-specific binding, so that target 114 or indicator 290 in solution that is not specific for the probe 116 does not bind to the surface. Examples of such coating material includes Codelink by Amersham and OptiChem by Accelr8, which comprise hydrogel-like coatings with both very low non-specific background, as well as electrical properties. Alternatively, the coating can comprise a derivatized silane.

Other Components

There are a number of other components comprising compete systems according to the present invention, including power controllers for establishing the potential differences between electrodes that will be cause and control the electrophoretic force on the targets 114, illuminators to illuminate the indicators 290, detectors to detect the signals generates by illumination of the indicators 290, and storage controllers (e.g. controllers and hard disk drives) that store the information from the detectors and then present it to the user or compare information from multiple sources or times. Some of these components are well-known in the art, such as electrophoresis power supplies (which can be computer controlled and which can be set to provide either constant voltage or constant current, and which can be supplemented with digital or analog electronic circuitry to provide low to high frequency waveforms as described elsewhere in this specification and which can also be used for dielectrophoresis), illuminators (e.g. lasers, arc lamps, incandescent lamps, microscope light condensers, and which can involve methods of coupling the light into light waveguides), indicators (as described above and below), detectors (cameras, lenses, filter sets, image analysis software), and the like, even as their arrangement and use is novel and to novel effect in the present invention. Where the components differ from prior art, they will be discussed both above and below.

Functional Description of the Present Invention

Figure 8:
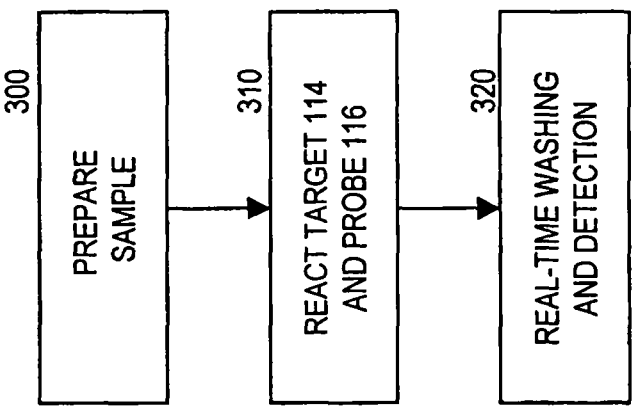
FIG. 8 is a schematic block flow diagram of the steps of the present invention.

The present invention can be considered to comprise three steps as shown in FIG. 8, a schematic block flow diagram of the steps of the present invention.

In a first step 300, the sample comprising the target 114 is prepared for use in the assay. The method of preparation depends upon the type of material being assayed, and can include the maceration of solid tissue, or alternatively the lysis of cells if the material to be assayed is of intracellular origin. Solid material can be removed from the preparation by centrifugation, filtration or other means, and if nucleic acid is the target 114, the nucleic acid can be purified away from the rest of the starches, lipids, and proteins of the preparation (indeed, whatever the nature of the target 114, it can be convenient to remove components that may interfere with later stages of the analysis). If the material is nucleic acid, it can be amplified by means such as polymerase chain reaction (PCR) or rolling circle amplification or other amplification methods. Generally, the material should be maintained in a condition that preserves target 114 reactivity with the probe 116, as well as the reactivity of the electrophoretic tag 270 with the probe 116. In general, the least amount of preparation will be used that allows for both high signal and low background, due to the cost, time, and artifacts that are generally introduced via preparation.

In this preparation step, the electrophoretic tag 270 can be reacted with the target 114 in order to generate a tagged target 275 as described in FIG. 6. Alternatively, this reaction can occur later in the process as described below.

In a second step 310, the tagged target 275 and the probe 116 are reacted. In the case of nucleic acids, this can comprise a step of hybridization. In the case of protein targets 114, this can comprise an antibody-hapten reaction, a protein-aptamer reaction, or a protein-protein reaction.

It is a teaching of the present invention to accelerate the reaction between the tagged target 275 and the probe 116. If the reaction is incomplete, the amount of target 114 bound to the probe 116 will be less than optimal. Additionally, because the rates of reaction for different targets to different probes 116 are generally different, and because the amounts of target bound to the probe will not be linear with time, it is hard to quantitate the amount of target 114 bound to the probe 116 without the reaction having gone to completion.

The means of accelerating the reaction involves the movement of the tagged target 275 under the influence of an externally applied force, which can be conveniently an electrophoretic, dielectrophoretic or magnetostatic force. For this description, electrophoretic forces will be used as an example. This force can be applied either by the placement of an electrode 200 under the positions of the probe 116, or through the influence of electrodes 210 and 220 that are placed to the sides of the probe locations 170, in a manner to be described below.

Figure 9:
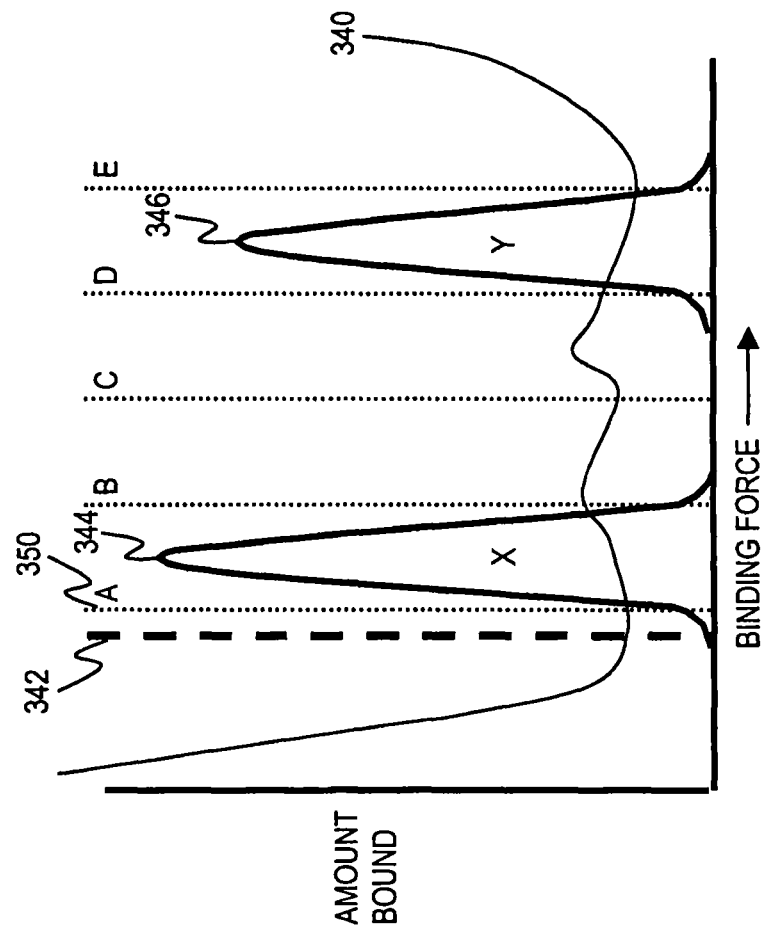
FIG. 9 is a graph of the amounts of material bound versus the binding force.

In the third step 320, unreacted tagged target 275 is separated from the probe 116 and the tagged target 275 that remains attached to the probe 116 is detected. Importantly, conditions are set such that tagged target 275 that is properly reacted with the probe 116 is not removed, and that other tagged target 275 that is non-specifically bound to the probe 116 or to the substrate 120 is removed. It should be appreciated that with multiple tagged target 275 and probe 116 pairs, the binding force will be different in the case of each pair. In order to discriminate specific from non-specifically bound material, a different discriminating force will optimally be used for each probe 116. This methodology is outlined in FIG. 9, a graph of the amounts of material bound versus the binding energy. Line 340 represents the amount of non-specifically bound material, and is characterized by a very large amount of material that is loosely bound, a variable amount of material bound with the intermediate energy, and some amount of material which is bound strongly. It should be noted that the shape of this curve will be different depending upon the materials being assayed, and that the arguments made below are not dependent upon the particular shape of the curve.

Two targets are shown in the figure: target X is represented by line 344 and target Y is represented by line 346. Target X has a lower binding energy with its corresponding probe 116 than the target Y. In a conventional assay in which a single discriminating wash is used for all target-probe pairs, the discriminating energy must be chosen such that it is less than the binding energy of the least tightly bound target. This binding energy is represented by dashed line 342. It can be seen, however, that using a single discriminating energy results in a background represented by the total of all non-specific binding 340 to the right of the line 342. In the location of target Y, for instance, significant nonspecifically bound material with binding energy both less than and greater that of the specifically bound target Y will be present.

In the present invention, washings corresponding to a number of binding energies will be used. These binding energies are represented by dashed lines 350 at forces represented by lines A, B, C, D, and E, which are successively applied. For instance, a first "wash" at discriminating energy A is applied, and virtually all of the tagged material bound at the location of probe X is detected. Then, washing at discriminating energy B is applied, and the material bound at the location of probe X is once again determined. The difference between the material at wash A and wash B is considered to be specifically bound material corresponding to target X. After subsequent washings at discriminating forces C, D, and E, the amount of target Y is considered to be that material present in wash D and not present in wash E at the location of probe Y. Thus, the proper discriminating energy for each target-probe pair is utilized using a bracketing pair of discriminating washes. In each case, the nonspecific background is only that part of line 340 that falls between the pair of discriminating washes specific for that probe location.

It should be noted that the rupture force is dependant on applied force and the rate of force applied. For example, under non-equilibrium conditions, the rate of force applied per unit of time actually changes the width of the potential energy landscape effectively increasing the integrated energy (force through applied through a distance) required to rupture the interaction. Another way of stating this is that rapid pulling apart does not allow time for the relatively slower unbinding process, so a large force is required to rip apart the molecules and that the energy landscape or barrier is significantly higher at rapid loading over lower loading rates of force. So depending on force loading rate, there will be multiple critical rupture forces. Furthermore, the shape of the loading rate versus critical rupture force is different for each receptor ligand interaction, since the intermolecular interactions are different. Thus, multiple antibody-antigen interactions and non specific binding can be resolved with dynamic force analysis—that is, by observing the rupture force plotted against loading rate, overlapping binding energy curves can be separated depending on loading rate. Therefore, the shape of the applied voltage curve is very important to control.

It should be noted that the reaction step 310 and the washing and detection step 320 can be performed cyclically multiple times. That is, after the washing and detection step 320 has removed all of the target 114 from the probe 116 (or the tag 270 from the target 114), another cycle of reaction and washing/detection can take place. This has two primary advantages. Firstly, if there are a small number of targets 114 in the analyte, the number of binding events detected will be small. By repeating the reaction and washing/detection steps, a larger number of binding events can be counted, improving the statistics of the results.

Furthermore, differing voltage dynamics (for example, voltage ramp profiles) can be utilized in each cycle of the two steps 310 and 320, in order to distinguish specific from non-specific binding events that might be distinguished in only by differing responses to voltage dynamics. For example, in a first cycle, the voltage dynamics can involve a step function in which voltages are changed rapidly, whereas in a second cycle, the voltage dynamics can involve a slow, ramped increase in voltage.

It should be noted that in order for the foregoing methods to be used, a means of real-time detection of the tagged target 275 to the probe must be available. That is, if each wash were to take a considerable amount of time and require many manipulations, only a small number of different discriminating washes could be used. With a real-time detection method, however, a large number of discriminating washes can be implemented, getting better definition of specific versus non-specific bound material.

It should be further noted that in the following discussion, the use of electrophoretic forces can be used in both accelerating the reaction as well as in providing discrimination between specific and nonspecifically bound material. It should be understood, however, that it is within the spirit of the present invention that in a given application, both uses of the electrophoretic forces acting on target-probe complexes, or alternatively, only one or the other of these uses of electrophoretic forces can be used to beneficial effect.

The number of discriminating washes used for a given assay can depend on the specific target-probe pairs used, but in most cases, the number of washes is preferably less than two times the total number of targets 114 being detected (with two steps each to "bracket" a particular target 114). It is also convenient for the spacing of the discriminating energies not to be evenly spaced, but to be tuned to bracket individual or groups of target-probe binding energies. It is also within the spirit of the present invention for the wash to be performed as a continuous gradient of stringency, which can be linear in stringency versus time, or non-linear, with detection of the target 114 being performed at intervals, wherein the number of detections is preferably less than two times the total number of targets 114 being detected.

Because of the natural dissociation constant for each of the target-probe pairs, which relates to a stochastic dissociation that is often thermally driven, it is convenient to choose conditions for discriminating washes in which this statistical component of dissociation is most attenuated. These conditions will in the case of nucleic acids, for example, involve moderate pHs, low temperatures, and higher salt concentrations. These conditions for proteins might include ionic strength, pH gradients, hydrophobicity, and solvent polarity as well.

It should be noted that while the present invention teaches the use of electrophoretic potential for discriminating washes, one aspect of the present invention relates more generally to the realtime detection of varying washing regimes, wherein the washing regimes can comprise a variety of different physical and chemical conditions beyond electrophoretic force. These forces can comprise increasing temperature, magnetic field strength (should the tagged target comprise a paramagnetic particle), dielectrophoresis (for particles, bacteria, and other targets and tagged targets), shear fluid flow, ionic strength (either increasing or decreasing), pH (either increasing or decreasing), surfactant concentration (either ionic or non-ionic), or competitor concentration (e.g. if the target 114 is a protein, to add increasing amounts of that protein so that when the bound target 114 is released, the competitor preferably binds to the probe due to its high concentration). In addition, more than one of these conditions can be applied either simultaneously or in sequence. While it is generally preferable for these conditions to be applied with gradually increasing stringency, it is also within the spirit of the present invention for the stringency to be increased in a step function, with rapid discreet increases in stringency. By monitoring the binding of the target 114 to the probe 116 at various increased stringencies of any of these conditions, discrimination of specific form non-specific binding can be improved.

Function Involving Electrodes Not Underlying Probe Locations

Figure 10:
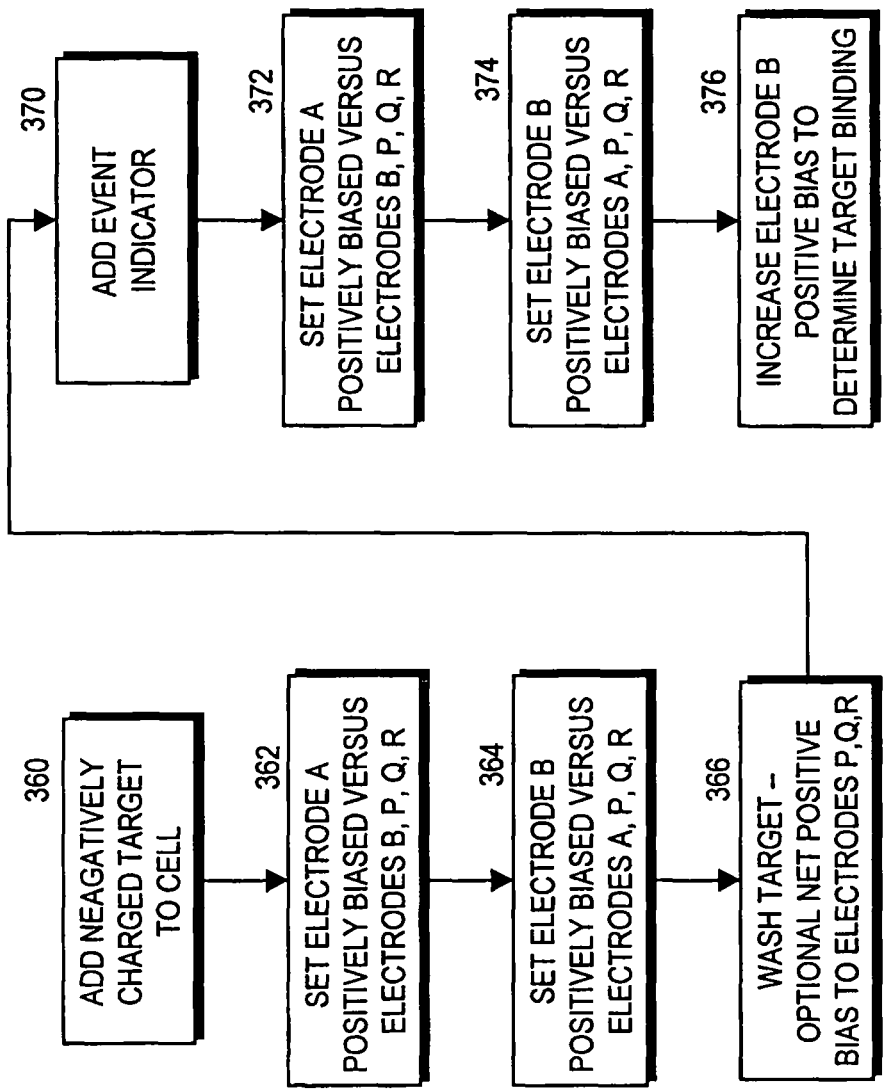
FIG. 10 is a schematic block flow diagram of a system involving electrodes not underlying probe locations.

FIG. 10 is a schematic block flow diagram of a system involving electrodes not underlying probe locations. In a step 360, a negatively charged target 114 is added to a reaction cell similar to that shown in FIG. 4B. For purposes of this discussion, the target 114 will be considered to be a nucleic acid, and the probe 116 will be considered to be a complementary nucleic acid sequence, although in practice, the probe 116 could also comprise proteins, glycoproteins, starches, or other molecules of interest. In a step 362, the electrode A will be positively biased relative to electrodes B, P, Q, and R, attracting the negatively charged target 114 to that electrode, on which it will collect. In a step 364, electrode B is positively biased relative to electrodes A, P, Q and R, so that the target 114 is drawn to the electrode B, during which transit it is brought into close proximity with the probes 116 at locations 170 in array 180, so as to facilitate reaction between the target 114 and the probe 116 can take place. The negative bias on the electrodes P, Q, and R maintains electric field vectors with downward pointing components during movement of the target 114 so that the target maintains close proximity with the probes 116. Once again, it should be noted that the location and the relative voltages on the upper electrodes P, Q, and R can be adjusted to shape the electric field vectors in the cell. The magnitude of the electric field vectors upward and lateral from the positions 170 must be lower than the binding force that binds the specifically bound targets 114 to their corresponding probes 116.

In an optional step 366, weakly-adhered nonspecifically-bound material can be removed from the array 180 by placing a small net positive bias to electrodes P, Q, and R, drawing the material away from the array 180. In a step 370, an event indicator, for example an electrophoretic tag 270, is added to the cell. Because of the high concentration of the electrophoretic tag 270, reaction with the target 114 occurs rapidly. In addition, reaction of the electrophoretic tag 270 with the target 114 can be accelerated by electrophoretic means. In a step 372, the electrode A is positively biased relative to electrodes B, P, Q, and R, transporting the electrophoretic tag 270 to the electrode A. In a subsequent step 374, the electrode B is placed positively biased relative to electrodes A, P, Q, and R, moving the electrophoretic tag 270 from electrode A to electrode B, with generally downward pointing electric field vectors, so that the electrophoretic tags 270 are in close proximity to the targets 114, with which they react. In a step 376, the electrode B positive bias is increased in a generally stepwise fashion as the amount of material bound at the probe locations 170 is monitored in order to determine the material that is specifically bound and to discriminate it from material that is nonspecifically bound. It should be appreciated that the event indicator can be a tag without particular electrophoretic properties, should the target 114 be itself charged. Furthermore, there may be no event indicator should the target 114 itself have properties of fluorescence, light absorption, index difference with the medium, or other properties such that it is detectable, rendered the step 370 optional.

It should also be noted that the targets 114 can be made to move back and forth multiple times between the electrodes 210 and 220, in each case increasing the amount of target 114 that binds to the probes.

Function Involving Electrodes Underlying Probe Locations

Figure 11B:
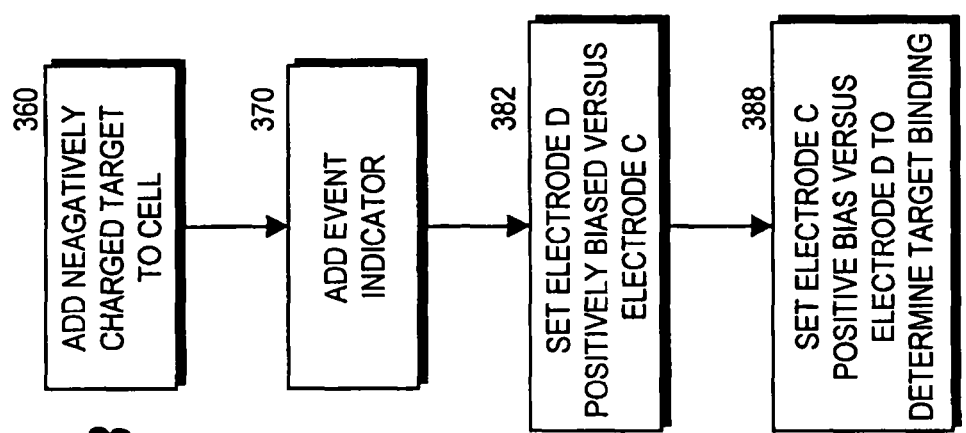
FIG. 11B is a schematic flow diagram of the operation of a cell involving electrodes under the probe locations using a tagged target.
Figure 11A:
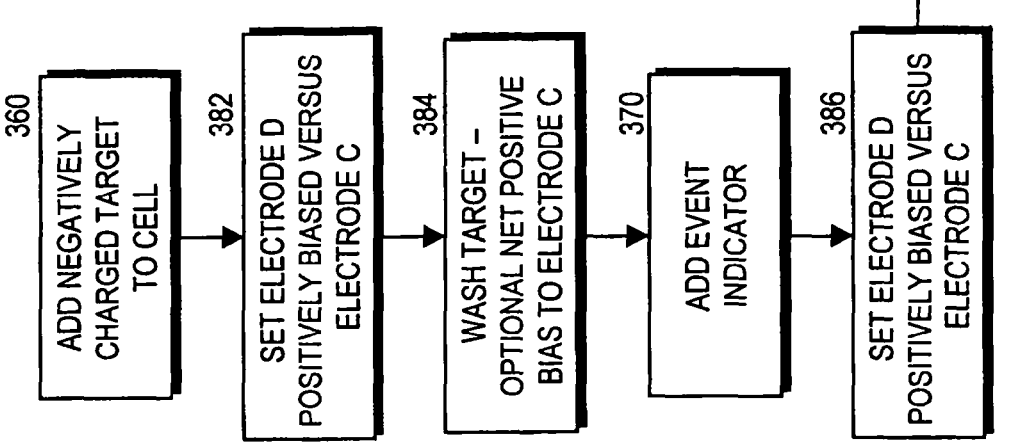
FIG. 11A is a schematic block flow diagram of the operation of a cell involving electrodes underlying probe locations, and can be best understood in relation to FIG. 4A.

FIG. 11A is a schematic block flow diagram of the operation of a cell involving electrodes underlying probe locations, and can be best understood in relation to FIG. 4A. In the step 360, a negatively charged target is added to the cell. In a step 382, the electrode D is positively biased relative to electrode C, causing the target to migrate onto the electrode where it is in close proximity to the probe 116 placed on array locations 170 on the array 180. Because of the close proximity, the reaction between the target 114 and the probe 116 occurs very rapidly. In a step 370, an event indicator, for example an electrophoretic tag 270, is added to the cell. In a step 386, electrode D is once again positively biased relative to electrode C. Under the influence of the electric field, the electrophoretic tag 270 migrates to electrode C wherein it reacts with the target 114. In a step 388, electrode C is set at a positive biased relative to electrode D. Electrode C's positive bias is increased in a generally stepwise fashion as the amount of material bound at the probe locations 170 is monitored in order to determine the material that is specifically bound and to discriminate it from material that is nonspecifically bound.

It should be appreciated that the step 370 and the step 386 can be eliminated by adding the electrophoretic tag 270 to the target 114 prior to adding the target 114 to the cell in the step 360. In this case, the target 114 is converted to a tagged target 275 prior to the application of a positive bias on electrode C in the step 382. The creation of the tagged target 275 can occur within the cell as shown in FIG. 11B, a schematic flow diagram of the operation of a cell involving electrodes under the probe locations using a tagged target 275. In the step 360, the negatively charged target is added to the cell, and in the step 370, electrophoretic tag 270 is additionally added to the cell. At this point, a tagged target 275 is generated. In the step 382, the electrode D is positively biased relative to electrode C and the tagged target 275 moves into close proximity with the probes 116 at the target locations 170, where reaction with the probes 116 occurs. In the step 388, discrimination of specifically bound versus nonspecifically bound material is performed as before.

The monitoring of the binding of the target 114 that occurs in the step 388 can be performed for an average of all of the material that is bound—for example, measuring the total output of light that is scattered from a tag that has a light scattering indicator. However, if the detector is an optical detector, and the detector is an imaging detector such as a camera or a laser scanner coupled with a photo multiplier tube, it is also within the spirit of the present invention for the binding to be determined for individual targets 114. In this case, the detector will need to store the locations of each target 114 between sequential detections, and the strength of binding of each target 114 to each probe 116 can then be determined.

Use of Magnetostatic Forces

It should be noted in the discussions above that magnetostatic forces can be substituted in certain cases for electrostatic forces. For the use of magnetostatic forces, however, the targets 114 must be tagged with paramagnetic particles, given that for the most part, the biological molecules or organisms to be detected are not in themselves magnetic. Examples of such particles include Estapor particles from Bangs Laboratories (Fishers, Ind.), and Dynabeads from Dynal, Inc. (Norway). Thus, the particles 293 and 295 of FIGS. 7C, E and F would be substituted with paramagnetic particles, which are preferably less than 1 micron in diameter, and more preferably less than 250 nm in diameter, and most preferably less than 100 nm in diameter; in general, the smaller the particle, the less it interferes with the diffusion of the target 114 towards the probe 116, and the faster the reaction kinetics. Instead of electrodes, the placement of permanent or electromagnets either above or below the probe 116 (in relation to the substrate 120) than provides the force the moves the magnetically tagged targets 114 towards or away from the probe 116. The magnitude of this force can be adjusted either by changing the distance of the magnetic field source from the probe 116 or the placement of shims of differing magnetic permeability, or in the case of an electromagnet, adjusting the current through the coils, the physical distribution of the coils, the presence of magnetically permeable material in or around the coils, and other such means as known in the art.

Real-Time Detection

As described above, the use of multiple washes of differing discrimination, as well as the monitoring of the binding of the target to the probe require the use of real-time monitoring. This is to be distinguished from the common conventional situation wherein after the reaction has proceeded for a predetermined period of time, the reaction is competed, the washes are performed, and then the substrates on which the reaction was performed are then prepared for detection. In many of the preferred embodiments of the present invention, an optical means of detection is employed. In those instances where the electrodes are opposed to each other (e.g. parallel and opposite), in order for optical detection to take place, one or both of the electrodes is preferably optically transparent, in order for an external optical device to receive the optical signal that is generated between the two electrodes.

With reference to FIG. 4B, this is easily accommodated, wherein the substrate on which the array 180 is placed can be transparent. However, it may be preferable for the detector in that case to be placed above the electrodes 195P, Q and R, or alternatively in the case of an arrangement such as FIG. 4A, the detector will generally be external to the electrodes 190 and 200. In such cases, the use of optically transparent electrodes is preferred, for which the preferred material for these electrodes is indium tin oxide (ITO). Because ITO is not stable generally to voltages above 2 V, this means that the potential between the electrodes in the case of ITO should be preferably maintained below this potential, as will be described in more detail below.

A more general discussion of detection will be provided below.

Control of Reaction Acceleration

Figure 12A:
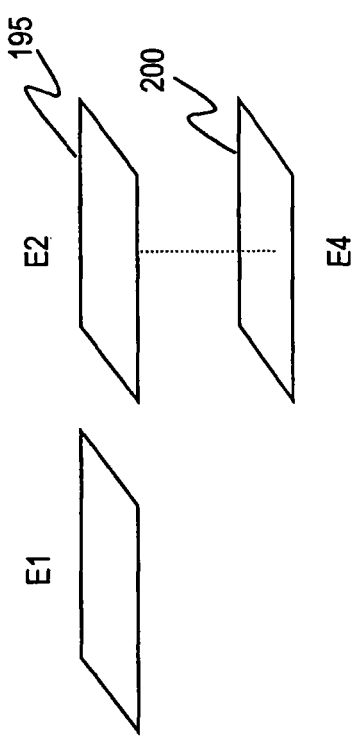
FIG. 12A is a schematic diagram of three electrodes arranged on two perpendicular axes within a reaction cell.

The acceleration of reaction according to the methods above can be improved by varying the electric fields both spatially and temporally so as to improve the reaction of the probe 116 with the target 114. FIG. 12A is a schematic diagram of three electrodes arranged on two perpendicular axes within a reaction cell. Electrode E1 and electrode E2 are representative of electrodes 195, while electrode E4 is representative of an electrode 200. That is, the array 180 is placed on top of the electrode E4. The voltage potential between the different electrodes will be varied in such a way so as to improve the reaction rates as described below. In the discussion below, the use of the terms target 114 and tagged target 275 are used roughly interchangeably.

Figure 12B:
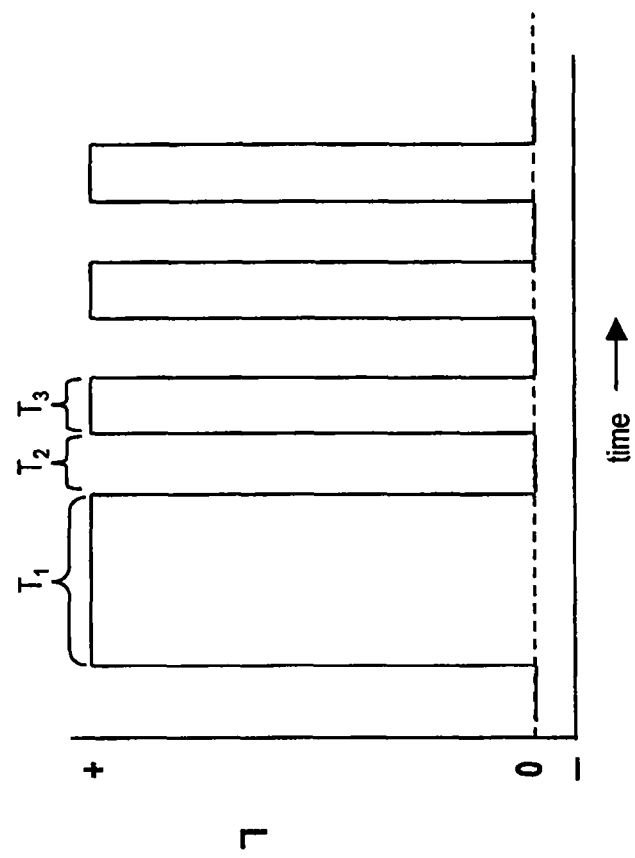
FIG. 12B is a graph of the potential difference between the electrodes E2 and E4 as they vary with time, with electrode E4 biased positively to E2.

FIG. 12B is a graph of the potential difference between the electrodes E2 and E4 as they vary with time, with electrode E4 biased positively to E2. There are three time periods represented on the graph, denoted as times T1, T2 and T3. In the period T1, the voltage potential is maintained for a considerable period, such that the majority of the target 114 is brought into juxtaposition to the probe 116. Because of the potential difference, both the probe 116 and the target 114 can be forced downward onto the substrate 120, wherein the maintained voltage restricts their ability to react with one another. This will occur when the probe 116 and the target 114 are of the same polarity of electric charge, such as in the case of nucleic acid hybridization, although in other target/probe pairs (e.g. protein-protein interactions), the charge polarity can be different in the target 114 and probe 116. Even in such cases, the target 114 can then be electrophoresed beyond the probe 116, impeding the reaction between the probe 116 and target 114. In both cases, it is convenient to have a period, described below, that reverses or relaxes the effects of the electrophoresis.

In the period T2, the voltage potential can be removed allowing free movement of the target 114 and the probe 116, accelerating the rates of reaction. However, during this period T2, the target 114 is allowed to diffuse away from the probe 116. Thus, during the period T3, the voltage potential is once more applied to maintain the close proximity of the target 114 in the probe 116. The periods T2 and T3 can be cyclically repeated, until such time that the majority of the complementary target 114 and probe 116 are reacted. The durations of the various periods can be varied depending upon the topology of the reaction cell, the characteristics of probes 116 and targets 114, as well as the various electrostatic charges on the different components, and the manner in which probe 116 is affixed to the surface 120. In general, for larger vertical and lateral dimensions of the cell, period T1 will be larger to allow for the larger distances over which the target 114 must be moved.

FIG. 12C is a graph of the potential difference between the electrodes E2 and E4 as they vary with time, arranged alternatively to that in FIG. 12B. Again, as in FIG. 12B, during initial period T1, the target 114 is allowed to migrate under the influence of the electrophoretic force to the probe 116. In this case, during a period T4, the electric field is maintained at a very low level so as to maintain the juxtaposition of target 114 to probe 116, but with a lower force than that used in FIG. 12B. This lower force is used in order to allow more movement of both the target 114 and the probe 116 so that they are not topologically constrained during the reaction. During an optional period T5, the electric field can be reversed very mildly, so as to release any target 114 that may have become enmeshed on the surface 120. The relative duration of the periods T4 and T5 will depend upon the number of factors, including the type of surface to which the probe 116 is attached, the charge of the electrophoretic tag 270, the binding force between the target 114 in the probe 116, the physical size of the electrophoretic tag 270, and other factors. It should also be noted that the duration of the successive periods T4 or the successive periods T5 need not be equal and may change over time.

FIG. 12D is a graph of potential differences between spatially displaced electrodes, such that the electric field changes not only magnitude but also in direction. With reference to FIG. 12A, electrode E2 is nearly vertically displaced (i.e. directly opposed) from the electrode 200 E4, and the electrode E1 is both vertically and laterally displaced from the electrode E4. As can be seen from the graph, electrode 4 is alternately biased positively and negatively relative to the vertically-displaced electrodes E1 and E2. In addition, in certain cases the bias is relative to E1 and in other cases the bias is relative to E2. This causes the electric field to vary in polarity, in magnitude, and in direction. This variation in direction means that tagged targets 275 that become sterically trapped on the surface 120 will feel force in varied directions that can facilitate in releasing them from their entrapment.

Figure 13B:
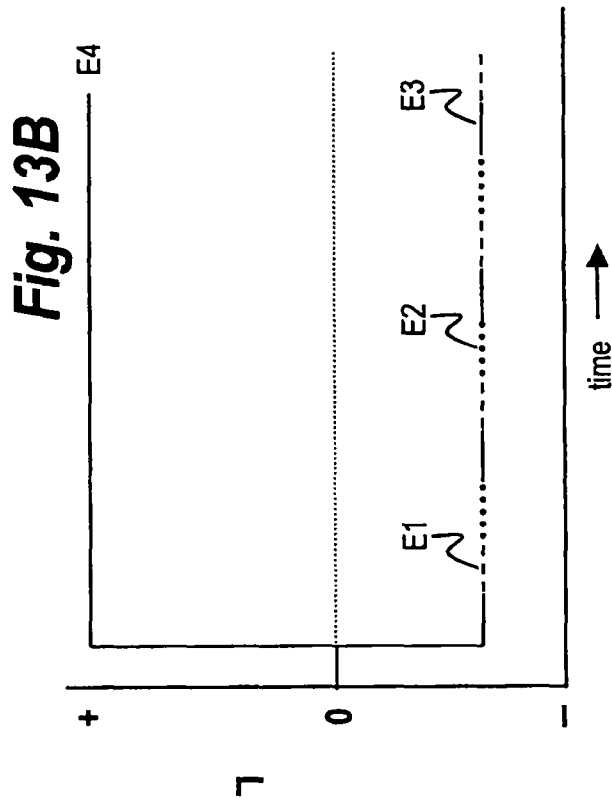
FIG. 13B is a graph of potential differences between the electrodes of FIG. 13A.
Figure 13A:
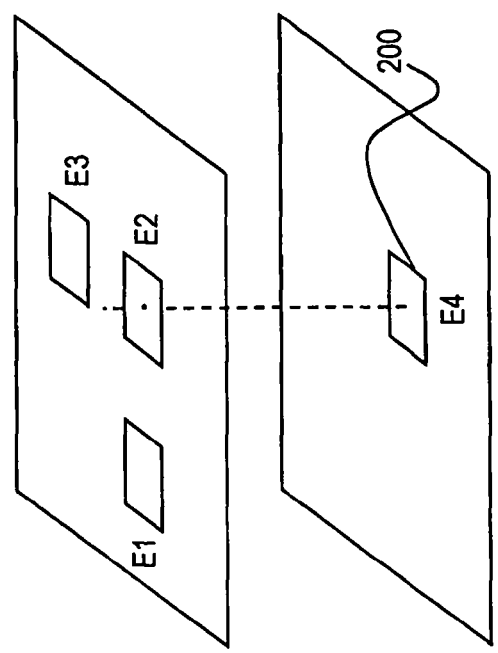
FIG. 13A is a schematic diagram with three electrodes displaced in two dimensions over a single electrode 200.

This arrangement can be carried out with various topological arrangements. FIG. 13A is a schematic diagram with three electrodes 195 displaced in two dimensions over a single electrode 200. Electrodes E1 and E3 are displaced in perpendicular directions from the electrode E2 which is vertically displaced from the electrode E4. FIG. 13B is a graph of potential differences between the electrodes of FIG. 13A. Electrode E4 is maintained at a roughly constant positive potential. The other electrodes, however, cycle between a nearly neutral potential and a negative potential, causing the electric field to cycle in direction with relatively constant magnitude.

It should be noted that the topological arrangements of the electrodes E1, E2 and E3 will vary with the shape of the cell. For instance if the cell is between a microscope slide and a cover slip, the thickness of the cell can be measured in hundreds of microns, which would cause an electric field between the electrodes E1 and E4 to be nearly horizontal. If the cell is within a microtiter well, the depth of the cell will be comparable to that of its width, such that the electric field between electrodes E1 and E4 will be more nearly vertical.

Electrochemistry to Improve Electrophoretic Acceleration

The electrophoretic reaction acceleration can be performed in a normal buffer, using the electrolysis of the water or the constituent salt ions (e.g. sodium and chloride) to engage in redox reactions at the electrodes as required to provide the current for the electrophoresis. There are a number of difficulties associated with the use of these buffers, however, for which we will use sodium chloride as an example. Firstly, if indium tin oxide (ITO) or other redox active materials is used at one or both electrodes (e.g. to provide an optically transparent or translucent, conductive electrode), the redox potentials powering the electrophoresis need to be less than that at which the electrode will participate in redox reactions. In the case of buffers with sodium chloride, for instance, the potential at which redox reactions occur at high rates is greater than 2 Volts, at which potential the ITO is unstable.

Furthermore, the redox products of sodium chloride electrochemistry include Na metal which reacts in water to form the strong base NaOH, and $Cl_2$, which reacts with water to form strong oxidizing reagents. These reagents, being very active, may be deleterious to the targets 114 and tags 270 being electrophoresed towards the electrodes.

Also, while salt provides conductivity to the electrophoresis, it also competes with the charged material being moved—the larger the conductance of the buffer, the lower electrophoretic force that is encountered by the material. Thus, it is beneficial to limit the conductance of the buffer. In general, it is preferable therefore for the conductivity of the buffer to be less than 1 mS/cm, and even more preferable for the buffer to be less than 100 µS/cm, and even more preferable for the conductivity of the buffer to be less than 10 µS/cm. In many instances, it is important for the ionic strength of the buffer, however, to be maintained at some reasonable level (e.g. >10 mM), for example for the viability of cells or to preserve the reaction of proteins or nucleic acids (e.g. hybridization), or alternatively to have a buffer to maintain a pH range. In these cases, it is convenient to use zwitterionic molecules to maintain ionic strength or pH. Specifically, in the case where nucleic acid hybridization is desired, it is convenient to use histidine buffer (e.g. see U.S. Pat. No. 6,051,380).

Choosing Appropriate Redox Accelerants

In order to reduce these effects, it is preferable to provide redox agents that do not suffer from the problems listed above. An example of such reagents is the benzoquinone/hydroquinone system. In this case, hydroquinone is oxidized at the anode to benzoquinone, and benzoquinone is reduced at the cathode to hydroquinone. Because the reactions are complementary at the electrodes (i.e. have reversed potentials), the only cell potential is due to differences in concentration rather than differences in standard potential at the electrodes, and thus the electrophoresis redox reaction occur at relatively low potentials between the two electrodes. Furthermore, because the two species are not charged, the redox agents do not significantly increase the conductivity of the solution and thus do not compete with the charged molecules (e.g. DNA) or material (e.g. bacteria) for transport via electrophoresis.

Figure 14A:
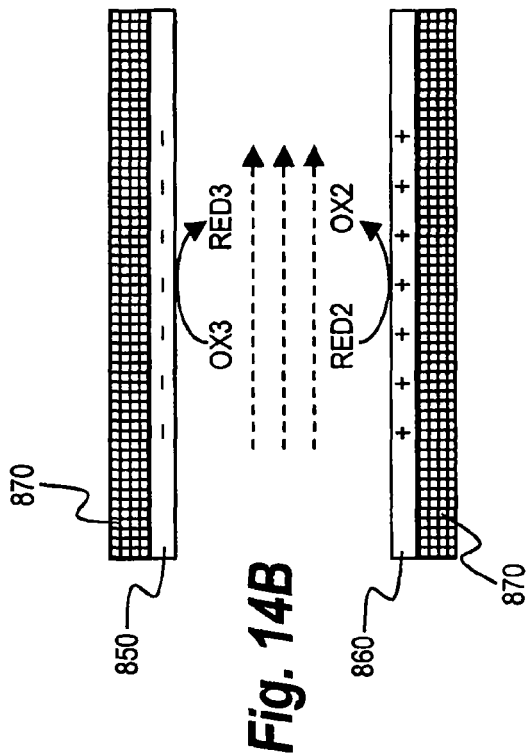
FIG. 14A is a schematic diagram of a closed system for electrophoresis.

The redox scheme as described above can operate either with respect to a closed or open system. FIG. 14A is a schematic diagram of a closed system for electrophoresis. On an upper substrate 870 is a cathode 850, and on a lower substrate 870 is an anode 860. In the region between the electrodes are two compounds, an oxidized molecule (OX1) which according to the discussion above could be benzoquinone, and a reduced molecule (RED1) which according to the discussion above could be hydroquinone. At the cathode 850, OX1 is reduced to RED1, which then moves either by electrophoresis or by diffusion to the vicinity of the anode 860. At the anode 860, RED1 is then oxidized to OX1, which then moves either by electrophoresis or by diffusion to the vicinity of the cathode 850, where the cycle can repeat itself.

Depending on the amount of availability of charge carriers (which can be unrelated electrolyte, RED1 and/or OX1, or charged molecules or materials to be transported), the electrophoretic force, and therefore the rate at which molecules or materials can be transported, can be limited to the rate of diffusion of OX1 to the cathode and RED1 to the anode. This rate of diffusion can be improved significantly be making the distance between the cathode 850 and the anode 860 small—it is preferable for this distance to be less than 2000 microns, even more preferable for this distance to be less than 1000 microns, and even more preferable for this distance to be less than 500 microns.

Figure 14B:
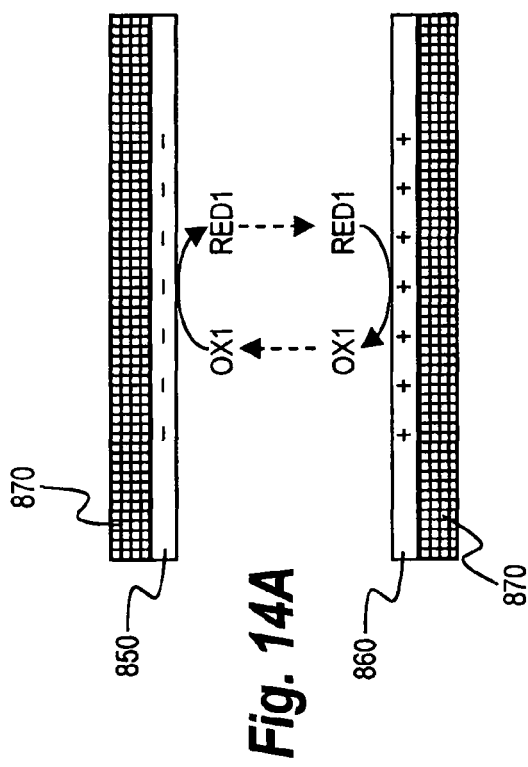
FIG. 14B is a schematic diagram of an open system for electrophoresis.

The system of FIG. 14A is closed, in that the system can be closed off from the environment, and electrophoresis can be continued indefinitely without replenishing the redox reagents. FIG. 14B is a schematic diagram of an open system for electrophoresis. The arrangement of substrates 870, cathode 850 and anode 860 is the same as that of FIG. 48A. However, in this case, there are two pairs of reagents which do not regenerate each other (either directly as in benzoquinone and hydroquinone, or by mutual quenching of redox products, as described below). At the cathode 850, an oxidized molecule OX3 is reduced to the molecule RED3, while at the anode 860, a reduced molecule RED2 is oxidized to OX2. The products RED3 and OX2 do not react with one another to regenerate the reactants, and so as soon as OX3 and RED2 are exhausted, electrophoresis will terminate. Thus, in this open system, in order to maintain electrophoresis, the reactants OX3 and RED2 must be continuously replenished, which is accomplished generally by maintaining a flow of new reactants in the electrophoresis buffer into the space between the electrodes. It should be noted that this flow will also remove any targets 114 to be transported, unless such targets 114 are somehow immobilized to the cathode 850 or anode 860 by the time that the buffer exits the region between the electrodes 850 and 860.

There are numerous redox pairs that can operate within the present invention. As described above, benzoquinone and hydroquinone are well suited to this, and are preferably used in concentrations above 1 mM, more preferably used in concentrations above 10 mM, and most conveniently used in concentrations above 30 mM. It should be noted that the use of benzoquinone and hydroquinone are limited to an extent by their limited solubility, and so more polar or charged derivatives can be conveniently used to increase their solubility, such derivatives including the substitution of the ring carbons not bonded to carbon with halogens, nitrates, hydroxyls, thiols, carboxylates, and amines, and other such moieties. It should be noted that it is optimal for the system for the resulting redox agents to be uncharged (except as will be shown below), so that their distribution is not affected by the system electrophoresis, and so the substitution with a positively charged group (e.g. an amine) is balanced by a second substitution with a negatively charged group (e.g. a carboxylate), such as in 2-amino, 5-carboxy para-benzoquinone. In such cases of derivatized benzoquinones and hydroquinones, the concentrations of the redox reagents can be conveniently increased.

Other similar redox pairs include ketone/alcohol and aldehyde/alcohol pairs, whose ketone carbonyl group can be flanked by alkyl or aryl groups, which groups can also be derivatized with halogen, nitrate, hydroxyl, thiol, carboxylate, amino and other groups so as to modify the charge on the molecule or to increase its solubility. Another convenient system is that of dithiothreitol/dithioerythritol and their oxidized forms (which can be formed by the partial oxidation of solutions of the reduced forms, for example, by hydrogen peroxide), or alternatively by alkanes with terminal thiol groups (e.g. 1,5 dithiobutane). In general, it is preferable for the two thiols groups to be on the same molecule (as in dithiothreitol) as opposed to on separate molecules (e.g. as in beta-mercaptoethanol), so that the oxidation reaction is a unimolecular reaction that is relatively less sensitive to concentration (although the single thiols, such as beta-mercaptoethanol are acceptable reducing agents for many applications).

It should be noted that the redox pairs above are oxidized and reduced in pairs of electrons in such a manner that the charge on both redox pairs is the same, and is preferably neutral. The requirement that pairs of electrons be transferred can, however, reduce the rate of the reaction, and so it can also be convenient to use pairs in which one electron is transferred in the redox reaction. Examples of such pairs include ferrocene/ferrocinium and their derivatives, and ferrocyanide/ferricyanide. In such cases, it is preferable to use pairs in which the reduced product is neutrally charged, and the oxidized product is positively charged in those cases where negatively charged molecules or materials will be transported. The reason for this is that the oxidized product supplies countercharge to the transport of the negatively charged transported molecules, and the reduced product is uncharged, and so does not compete for transport with the negatively charged transported molecules.

Another configuration of the system is that where the products of the redox reactions quench one another, such as in the following:

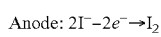

Anode: $2I^- - 2e^- \rightarrow I_2$

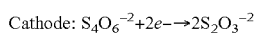

Cathode: $S_4O_6^{-2} + 2e^- \rightarrow 2S_2O_3^{-2}$

The products of this reaction spontaneously react with one another according to $2S_2O_3^{-2} + I_2 \rightarrow S_4O_6^{-2} + 2I^-$, regenerating the starting state. The use of iodide or another halide is convenient, since the iodide is moved through electrophoresis towards the anode, and the resulting iodine is neutrally charged and can move through osmosis towards the other electrode where it will meet with the thiosulfate for the regeneration of the initial system.

In open loop systems without recycling, where the redox pairs do not regenerate one another during their respective reactions, the range of redox agents is broader, and conveniently includes compounds including glutathione, ascorbate, methyl viologen, phenazine methosulfate, trolox, and others, including their redox pairs (such as GSSG for glutathione and dehydroascorbate for ascorbate, oxidized methyl viologen for methyl viologen). In this case, it is sometimes convenient that the charge of the molecule be such that the reactant be attracted towards the electrode at which it will participate in redox reactions (i.e. reactants to be oxidized at the anode should be negatively charged and reactants to be reduced at the cathode should be positively charged). This can generally be accomplished by derivatizing the molecule with one or more appropriately charged moieties. The main disadvantage of this is that a negatively charged redox agent, while increasing the rate of reaction, can also compete with the negatively charged transport molecules, such that increasing the amount of redox reactant can even reduce the overall transport of the transport molecules. Thus, care needs to be taken through experimentation to ensure that negatively charged redox reagents do not have an overall deleterious effect.

It should be noted, however, that small molecules of a redox pair, because of their high diffusion rates, are only moderately affected by the electrophoresis, and over the short distances that generally exist between the cathode and anode, show a modest gradient over the electrodes (often only 2-3 fold, and generally less than 10-fold). In this case, it may be useful to have one or both redox reagents be neutral or positively charged. In the case where both agents are positively charged, it is preferable that the agent that reacts at the positively charged anode be in larger overall molar concentrations to compensate for the lower local concentrations at the anode.

In those cases where microorganisms are being transported in the presence of redox agents, it is important to note that some of the redox agents mentioned above can have toxicity for microorganisms. In cases where the subsequent growth or monitoring of live organisms is desired, this can be a significant problem. For that reason, it is useful either to use low concentrations of the toxic redox reagent (generally the oxidizing agent), to limit the duration at which the microorganism is exposed to the agent, or to use an agent with lower toxicity, even should that agent have less desirable redox properties. In addition, bacteria that have been exposed to a toxic redox agent can be treated after exposure to a counteracting agent. For example, should the toxic redox agent be an oxidizing agent, the addition of a reducing agent such as beta-mercaptoethanol or dithiothreitol can reduce the effects of the oxidizing agent.

It should be noted that the one of the goals of the use of the redox agents is to allow electrophoresis to occur at a lower potential, both so as to minimize the production of harmful redox products (e.g. chlorine products from chloride), and as well so that optical detection can occur using ITO electrodes, which can be harmed by high potentials. Thus, the cell potential of the redox pairs chosen for the application is preferably under 2 V (the potential at which ITO begins to be affected), and even more preferably under 1 V and most preferably under 500 mV, since the range of potentials between the lowest potential at which electrophoresis occurs (i.e. 500 mV) and the endpoint (i.e. 2 V) will give some measure of control over the rates of electrophoresis. Even in those cases where the standard cell potentials of the redox agents may be outside of these ranges, the use of differing concentrations of oxidizing agent and reducing agent can provide a cell potential that allows for useful operation.

Passivation

Redox products generated at the anode and cathode can be potentially harmful to the molecules and materials being transported to these surfaces. For example, many of the redox reactions generate $H^+$ ions at the anode, which cause a local reduction of pH. This reduction in pH, if large enough, can disrupt nucleic acid hybridization, denature proteins, interrupt protein-protein or protein-nucleic acid interactions, or kill bacteria. Other redox products that are of potential danger also include strong bases, and strong oxidizing or reducing agents. In order to prevent these products from interfering with the molecules or materials to be detected at the anode or cathode, it is preferable to have a passivation layer over the electrode.

In general, it is convenient for this passivation layer to be such that proteins and nucleic acids are not detrimentally affected by the chemical or physical properties of the passivation layer directly and that the passivation layer not have a significantly detrimental effect on the redox reactions that occur at the electrode. It is preferable that the passivation layer be at least 2 nanometers thick, and more preferable that the passivation layer be at least 5 nanometers thick, and most preferable that the passivation layer be at least 25 nanometers thick, so that the interaction of the targets 114 and probes 116 with the products of redox reactions at the electrodes be reduced. Convenient forms of passivation layers include polymers comprising either with polyacrylamide (e.g. Codelink by Amersham) or polyethylene glycol constituents (e.g. OptiChem by Accelr8), modified with functional groups to which probes for detection can be attached.

Inhomogeneity Artifacts

Figure 15:
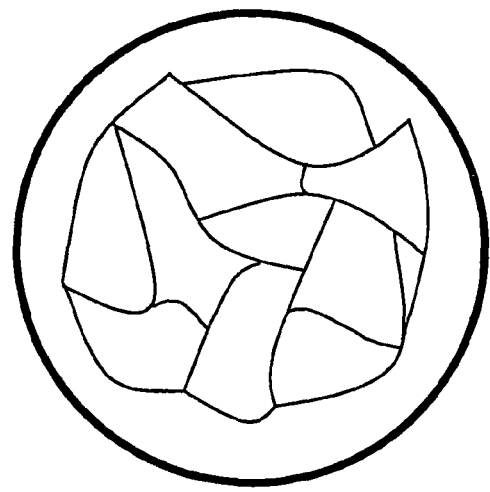
FIG. 15 is a topview schematic of a region in which cell of inhomogeneity have formed.

It has been observed that under conditions of 10 mM benzoquinone and 10 mM hydroquinone, an indium tin oxide (ITO) electrode separation of 300 microns, and a potential of greater than 1.5 Volts and less than the breakdown voltage of the ITO, an inhomogeneity develops either with soluble (e.g. nucleic acid coupled with a fluorescent dye) or insoluble (e.g. polystyrene spheres) markers. The inhomogeneity is evidenced by areas of concentration and rarefaction, where the areas of concentration start as roughly circular spots hundreds of microns across that elongate and condense into a pattern of cells, in which the borders are areas of concentration, and the central regions of the cells are areas of rarefaction. FIG. 15 is a top-view schematic of an approximately 1 cm diameter region in which such cells have formed. In general, this inhomogeneity can be an impediment to the use of accelerated transport via electrophoresis.

There are a number of methods of reducing this inhomogeneity. In a first reduction method, the strength of the electrophoretic force can be reduced, either by decreasing the voltage, or by increasing the conductivity of the solution. For example, in a solution of 10 mM benzoquinone and 10 mM hydroquinone and very low conductivity (e.g. <100 μS/cm), the cells do not appear very strongly below 1.4 volts. In a second reduction method, periods of strong electrophoretic force can be interspersed with periods of lesser or no electrophoretic force, wherein the amount of lesser electrophoretic force is preferably less than 50% of the maximal force, and more preferably less than 25% of the maximal force, and is most preferably less than 10% of the maximal force. In general, the period of strong electrophoretic force should be less than that at which the cells first form, and such periods are preferably no more than 5 seconds, and more preferably no more than 2 seconds, and most preferably no more than 1 second. The periods without electrophoretic force are conveniently substantial enough to allow diffusion of ions to distances large compared with the vertical size of the cells (i.e. the distance between the electrodes), and are preferably more than 100 milliseconds, and more preferably more than 300 milliseconds, and most preferably more than 1 second. In a third reduction method, it is convenient to allow liquid flow to break up the cells, such as through the use of temperature convection aided by unequal heating of the walls of the chamber 805, or through movement of fluid through the chamber 805.

It should be noted that while ITO or other transparent electrode material is preferable for real-time monitoring via visible indicators, this does not mean that both the cathode and the anode need to be comprised of ITO. In other instances, it can be preferable for one of the electrodes to be transparent, allowing observation into the reaction cell, while the other electrode to be a relatively non-reactive, opaque electrode, such as gold or a refractory metal, such as platinum, palladium, or iridium which are stable in electrophoresis. In these cases, the resistance in the metallic electrode will be very small, which can reduce the inhomogeneity effects above, and furthermore, the potential on the metallic electrode may not have the same deleterious effect as on the ITO electrode (e.g. with a Pt electrode), allowing higher potential to be used in the cell.

Alternatively, both electrodes can be opaque, with one electrode being coated with gold. In this case, the detection can be made optically via surface plasmon resonance.

Combination of Mixing and Electrophoretic Reaction Acceleration

Given that the electrode 200 is small relative to the lateral dimensions of the cell, application of force towards the electrode 200 will result in relatively even distribution of the tagged target 275 on the electrode. If the specific location 170 is small relative to the size of the electrode 200, this will result in only a small fraction of the tagged target 275 being bound to the probe 116. It is therefore advantageous to combine the step of mixing with or interspersed with the application of forces towards the electrode 200. This is depicted in FIG. 16A, a schematic block diagram of a reaction involving both vertical forces and horizontal forces so as to accelerate the reaction of a tagged target 275 with the probe 116. The methods of providing mixing, such as horizontal forces, will be discussed in greater detail below, but can be considered to include physical mixing of the medium in the cell (e.g. through the use of a physical stirring mechanism, pumps, electroosmotic flow, surface wave acoustics, and other means), the use of horizontal electrophoretic forces on the targets 114, the use of magnetic forces on the targets 114, and other convenient means. Those forces comprising bulk flow of the solution (e.g. electroosmosis, stirring, pumps, and surface wave acoustics) are particularly easy to implement. The vertical forces can comprise electrophoresis, dielectrophoresis, filtration, magnetic field attraction and other such forces as will bring the tagged target 275 (or a suitable target 114 that is not tagged) into proximity with the probe 116.

It should be noted that the use of "vertical" and "horizontal" is used in relation to the surface of the electrodes, and is not related to gravity, up/down or other coordinate schemes. Given the orientation of the diagrams, horizontal can be understood in this context to be parallel to the electrode (or more generally, the surface on which the probe resides), while vertical can be understood in this context to be perpendicular to the electrode.

For example purposes, the target 114 is a single stranded DNA 470, and the tagged target 275 additionally comprises an electrophoretic tag 270. The probe 116 comprises a complementary single stranded DNA probe 480, which is attached to the substrate 120. Vertical forces will tend to move the tagged target 275 vertically towards the probe 480, whereas the horizontal forces will allow the tagged target 275 to interact with probe 480 at various locations 170 within the array 190.

Figure 16B:
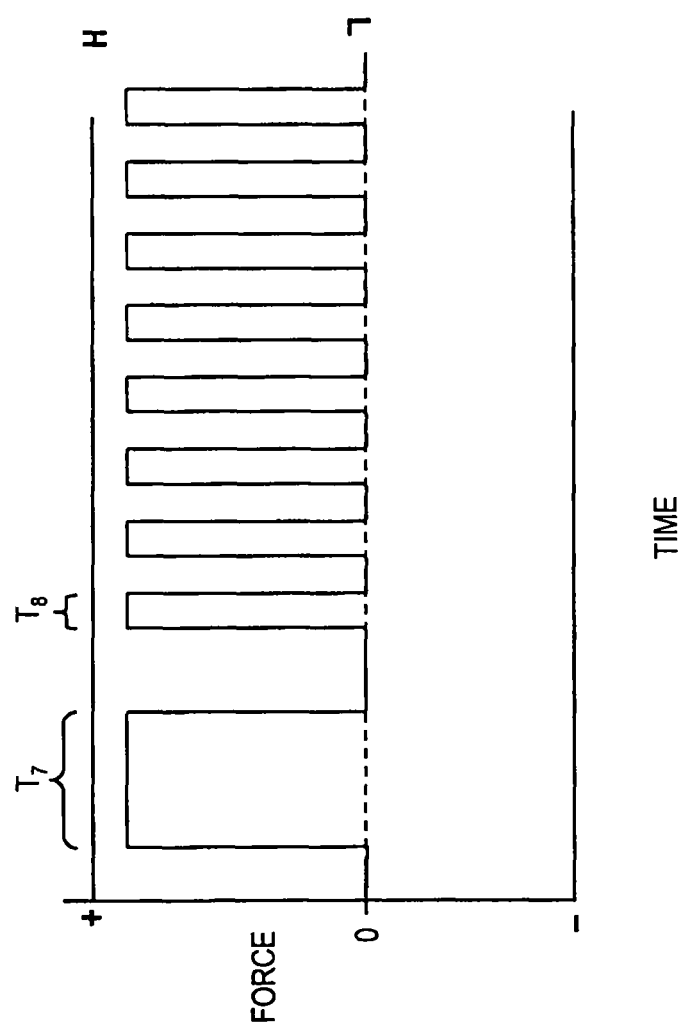
FIG. 16B is a graph of the electrical potential causing movement of the tagged target vertically, in time relation to the horizontal forces causing mixing of the tagged target.

FIG. 16B is a graph of the electrical potential causing movement of the tagged target 275 vertically, in time relation to the horizontal forces causing mixing of the tagged target 275. For purposes of this graph, a positive horizontal force is considered to be in a constant arbitrary direction along the substrate 120. Furthermore, a positive vertical force is considered to be in a direction that encourages the movement of the tagged target 275 towards the probe 480. As can be seen from the figure, the horizontal force is relatively constant. However, the vertical force varies in time, and is sometimes approximately neutral and at other times very strong. The vertical force is released periodically in order to allow the tagged target 275, which can become enmeshed on the substrate 120 during the application of the vertical force, to move laterally. The vertical force is applied initially for a long duration T7 in order to bring the tagged target 275 near to the probe 480. Once the target is in close proximity to the surface of the substrate 120, subsequent applications of vertical force can be either of shorter duration, or of lower magnitude, or both.

Consider, for example, a horizontal force that is sufficient in magnitude and in duration such that during the course of the reaction, the tagged target 275 moves approximately the width of a location 170. In such case, the location 170 will encounter approximately twice the tagged target 275 than it would without the application of horizontal forces, assuming minimal diffusion.

It is also within the spirit of the present invention for the horizontal forces to switch direction, so that the target 275 moves back and forth over the probe 116. In such case, the target 275 will have multiple possibilities of interacting with the probe, and will thereby increase its binding. Also, if the probe is attached through a hydrogel coating, some probe 116 may be sterically hindered from interacting with the target 275 if the target is moving from one or another direction, and it can be advantageous for the target 275 to move back and forth across the probe so as to provide different movements of the target 275. Also, in order to increase the amount of binding, the rate of horizontal movement can be decreased, or the rate of vertical movement increased.

Control of Mixed Vertical/Horizontal Reaction Forces

Figure 17B:
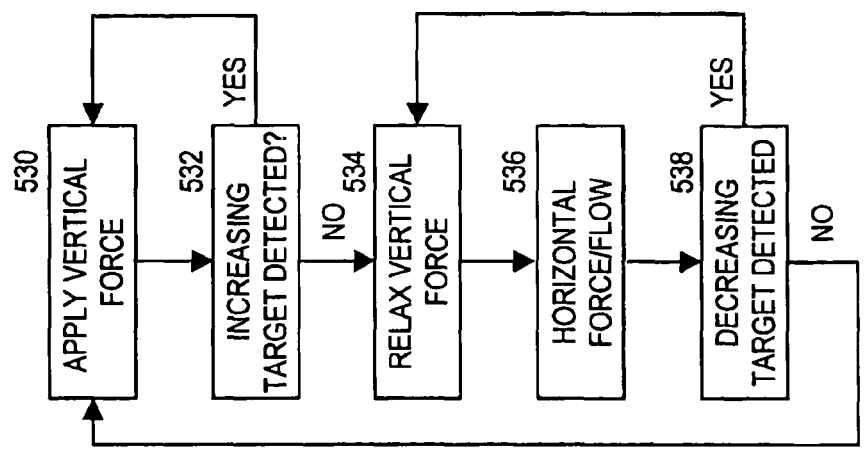
FIG. 17B is a schematic block flow diagram of the operation of the system of FIG. 17A.
Figure 17A:
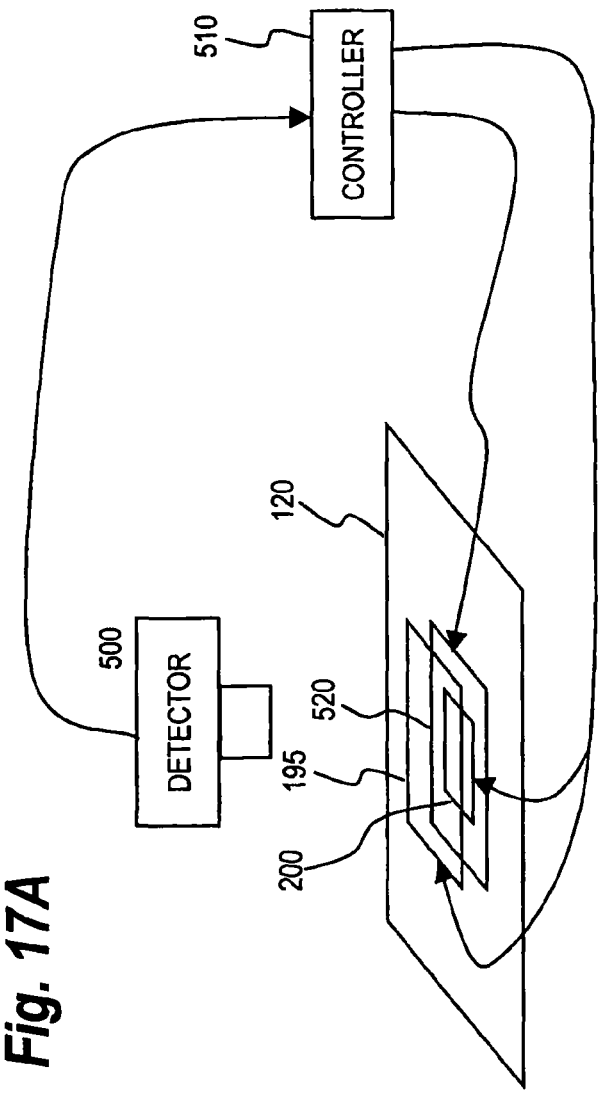
FIG. 17A is a schematic block diagram of the means of controlling the horizontal and vertical forces.

FIG. 17A is a schematic block diagram of the means of controlling the horizontal and vertical forces. The electrode 200 lies on the substrate 120 and is surrounded by a horizontal force applicator 520. Different means of applying horizontal force will be described in detail below. The applicator 520 is connected to a controller 510, which in turn receives input from a detector 500. The controller controls both the magnitude of horizontal force applied by the applicator 520, as well is the vertical force that is directed by the electrodes 195 and 200. The detector 500 monitors tagged target 275 that is in close proximity to the electrode 200 in real time. That is, tagged target 275 that is within tens or hundreds of nanometers of the electrode 200 is detected, whereas other tagged target 275 at a further distance from the electrode, is not. The means by which this real-time monitoring is performed by the detector 500 will be discussed in greater detail below.

FIG. 17B is a schematic block flow diagram of the operation of the system of FIG. 17A. In the step 530, the controller 510 causes a vertical force to be exerted between the electrodes 195 and 200 such that the tagged target 275 moves towards the electrode 200. In a step 532, input from the detector 500 is used by the controller 510 to determine whether an increasing amount of tagged target 275 is being detected that is juxtaposed to the electrode 200. If increasing target is being detected, continued vertical forces are applied in the step 530. If no new tagged target 275 is detected by the detector 500, the controller relaxes the vertical force in a step 534. In a step 536, the horizontal force or flow is either maintained or activated at this point. Because of the relaxation of vertical force in the step 534, tagged target 275 diffusing from the surface of the electrode 200 comes under the influence of the horizontal force or flow and moves laterally along the surface of the electrode 200. In a step 538, the detector 500 monitors the amount of tagged target 275 juxtaposed to the surface of the electrode 200. If the amount of target is still decreasing, the relaxation of the vertical force in the step 534 is maintained. Alternatively, a fixed amount of time can be allowed to elapse. Once the amount of target detected by the detector 500 is relatively steady, or the fixed amount of time elapses, the cycle is repeated beginning with the step 530.

Horizontal Forces and Flows

There are a number of different horizontal forces and flows that may be used within the spirit of the present invention. Among these include electrophoretic forces, electroosmosis, acoustic waves, mechanical stirring, and fluid pumping. For example, in FIG. 4B, lateral electrodes 210 and 220 can be used to apply horizontal forces to tagged targets 275. In such case, the magnitude of the vertical electric field can be adjusted by the potential on the reference electrodes 195, in relation to the magnitude of the horizontal electric field from the electrodes 210 and 220.

With respect to acoustic waves, piezoelectric actuators can be placed either on the substrate 120 or on the cover 111 in a topological arrangement such that under a high frequency control signal, surface acoustic waves in the glass cause mass transport of the fluid in which the tagged target 275 is suspended. In such case, a convection current is created within the cell which maintains a constant laminar flow across the surface of the substrate 120. By alternating the control of the piezoelectric signals, periods of turbulent mixing can be alternated with periods of laminar flow.

Mechanical or electroosmotic pumping can also be used to create laminar flow across the surface 120. While mechanical pumping is convenient for larger volumes, electroosmotic pumping can be used to assist even in the case of extremely small volumes. In such case, the electroosmotic surfaces can be incorporated either into the substrate 120, or more conveniently into the cover 111, since the substrate 120 is often covered by a custom surface used primarily to bind probe 116 and to reduce the amount of nonspecific binding, and which may be a less effective surface for creating electroosmotic forces.

Figure 18B:
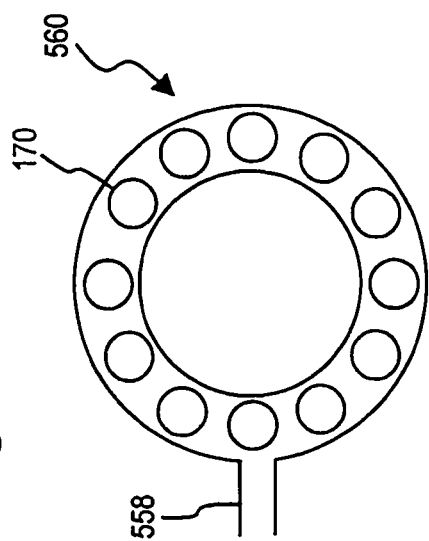
FIG. 18B is a top view diagram of the probe electrode.
Figure 18A:
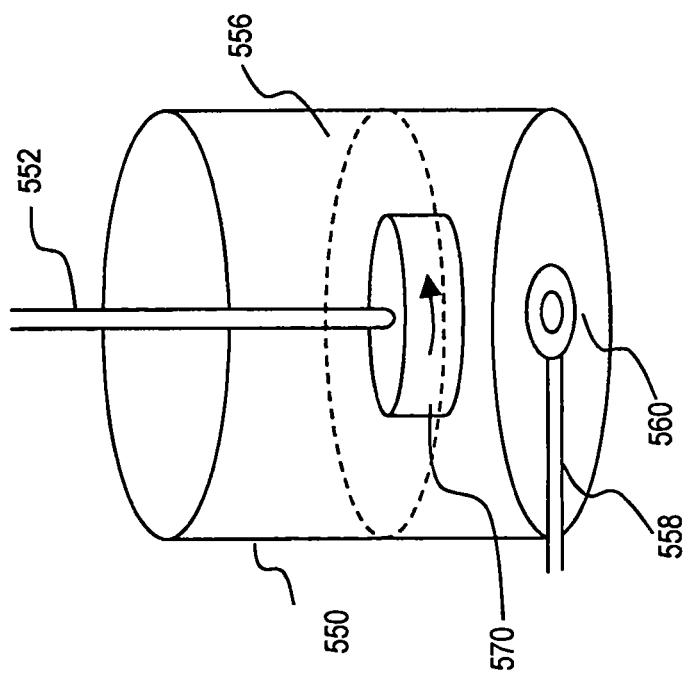
FIG. 18A is a perspective diagram of a mechanical stirring system that can be used within a microtiter plate well.

FIG. 18A is a perspective diagram of a mechanical stirring system that can be used within a microtiter plate well 550. The microtiter plate well 550 has a round probe electrode 560 on its bottom surface connected to the outside of the microtiter well 550 by an electrical trace 558. A reference electrode 570 is immersed within the analyte fluid whose height is represented by the dashed line 556. The reference electrode 570 is mounted on a shaft 552 which has both mechanical and electrical connections to actuators not shown in the figure.

During operation, the shaft 552 provides not only electrical connections through which a potential bias can be placed on the reference electrode 570, but in addition, the shaft 552 causes the reference electrode 570 to rotate. Because of the viscosity of the analyte fluid, the fluid convects in a circular motion around the microtiter plate well 550, with roughly equal degrees of movement within each radius from the center of the well 550. By reversing the direction of rotation of the shaft 552 in the reference electrode 570, turbulent flow within the well 550 can be induced.

It should be noted that due to the symmetry of the situation, and due to the desire to have roughly equal amounts of conductive flow for each of the probe locations 170, it can be preferable for the probe electrode 560 to have circular symmetry. FIG. 18B is a top view diagram of the probe electrode 560. The electrode 560 is arranged as an annular ring of conductive material attached to the trace 558. Probe locations 170 are arranged around the ring, and are roughly equidistant from the center of the microtiter well 550. In this arrangement, there is no preference in the electric field or the association of targets 114 to probes 116 based on physical location. Furthermore, conductive laminar flow induced by the electrode 570 will cause tagged targets 275 to move in a circular movement around the electrode 560.

It can alternatively be convenient for the reference electrode 570 not to be symmetrically placed at the bottom of the shaft 552, but rather to be asymmetrically disposed. In such case, the electric field direction will rotate with the shaft 552, providing the benefits of changing electric field directions, as described above.

The microtiter plate assays can be run either one at a time, or multiple assays at a time. FIG. 19A is a perspective diagram of a microtiter plate 590 with a set of electrodes 570 and shafts 552. The electrodes 570 and shafts 552 each fit into single microtiter wells 550 arranged in a grid. The electrodes 570 and shafts 552 can either rotate or be in fixed position. Depending on the arrangement, it is convenient either to have all of the electrodes 570 and shafts 552 be fixed with respect to each other, allowing for parallel operation in all wells and for simple and inexpensive construction, or individual electrodes 570 and shafts 552 can be independently controlled. Alternatively, instead of a two-dimensional array of shafts 552 and electrodes 570 as shown, there can be a one-dimensional array, in which a single row of wells on the microtiter plate are processed at one time.

The microtiter plate 590 can be of unitary construction, or alternatively be constructed of a top plate and a bottom plate, in which the top plate is made of plastic and defines the sides of the wells, whereas the bottom plate is made of plastic, glass or other substrate that is substantially flat, and which is coated with a material reducing non-specific binding and to which probes 116 can bind. In such case, the bottom plate is adhered to the top plate using adhesive, preferably after the printing of the array 180 of probe locations 170. For purposes of the present invention, it is convenient for electrodes to be placed on the bottom plate prior to the printing of the probes 116 or the adhering of the bottom plate to the top plate.

Figure 20B:
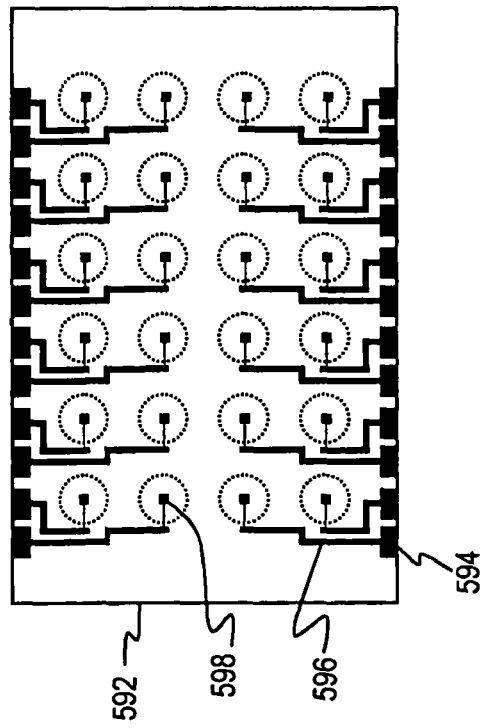
FIG. 20B is a top view of the arrangement of electrically-connected well electrodes on a bottom plate.
Figure 20A:
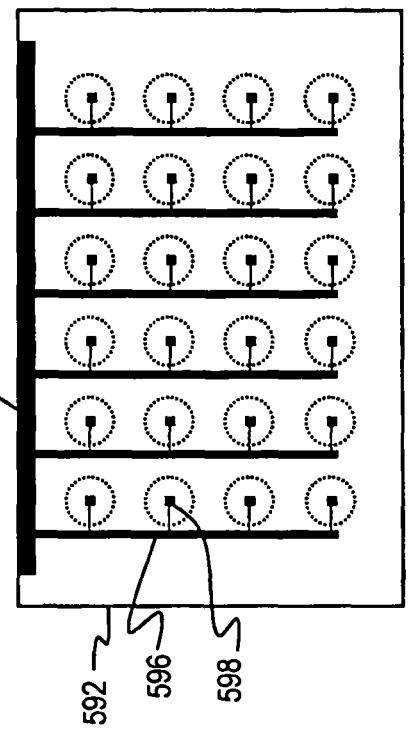
FIG. 20A is a top view of the arrangement of well electrodes on a bottom plate 592.

FIG. 20A is a top view of the arrangement of well electrodes 598 on a bottom plate 592. The well electrodes 598 can be square (as shown), rectangular, ellipsoidal, circular or annular (as in electrode 560), and are connected to end pads 594 via traces 558. These traces can be of relatively constant width, but are preferably narrower at the locations of the wells (denoted by dotted lines), where the majority of the electrically conductive area is preferably that of the well electrodes 598. It is also within the spirit of the present invention for the electrically-conductive traces that are not part of the electrode 598 to be covered with a non-conductive coating (e.g. semiconductor materials, ceramics, oxides, and other materials), but this is an additional step and cost of manufacture and may not be always convenient. In addition, there may be multiple traces per well, such as would be convenient with electrodes not underlying probe locations.

There is an attachment pad 594 for each electrode 598, to which the electrical attachment is made. This is less convenient when the number of wells 550 (and therefore electrodes 598) becomes very large. Alternatively, multiple electrodes 598 can be connected to a single pad 593, as shown in FIG. 20B, a top view of the arrangement of electrically-connected well electrodes 598 on a bottom plate 592. In this case, there is a single electrode 593 to which all electrodes 598 are electrically connected. Even if not all electrodes 598 are in simultaneous use, this arrangement allows for simple electrical connectivity, and no harm occurs with the parallel connection with the unused electrodes 598. Other arrangements are also within the spirit of the present invention, such as connection of all electrodes 598 within a single row or column of the array of wells 550, whereas each row or column is connected to a different attachment pad 594.

As described above, the bottom plate 592 is adhered to a top plate. If the bottom plate 592 is smaller than the top plate, the pads 594 or 593 can be grabbed by an electrical attachment device from underneath the plate (access through the top and sides is prevented by the top plate). An alternative arrangement that succeeds regardless of the relative sizes of the top plate and the bottom plate 592 is shown in FIG. 19B, a perspective view of a top plate 591 comprising access ports 597. In this arrangement, the access ports 597 provide side access to connect with the pads 593 or 594. The access ports 597 are placed according to the locations, number and sizes of the pads, and access to multiple pads from a single port 597 is within the spirit of the present invention.

An alternative arrangement is for the bottom plate 592 to be uniformly conductive, and maintained at a ground potential. In such case, the electric field within each microtiter well 550 can be independently adjusted by adjusting the potential on the corresponding electrode 570. In the case where one electrode 570 is operating at the time, the use of the uniformly conductive bottom plate 592 is straightforward. When multiple wells 550 are simultaneously being operated via a multiplicity of operating electrodes 570, it is optimal if the electrical conductivity of the analyte solution in each well is low relative to that of the bottom plate 592. The electrical conductivity of the analyte solution can be adjusted by, for example, lowering the concentration of ions in solution.

Figure 21:
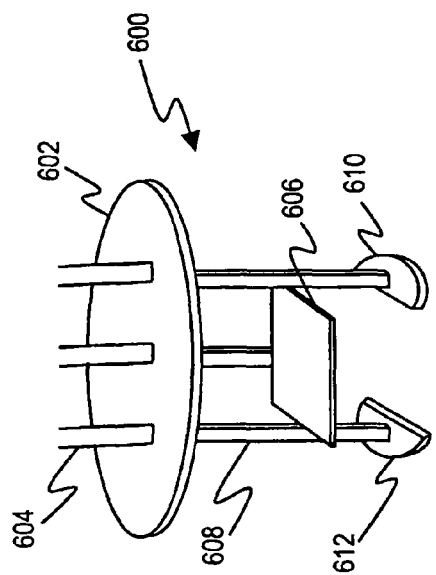
FIG. 21 is a schematic drawing of a cross-section of a detection system comprising a detection sandwich on a substrate.

Microtiter wells can be used within the present invention without use of permanent electrodes on the bottom plates 591. FIG. 21 is a perspective side diagram of an integrated electrode 600 for microtiter plates. The integrated electrode 600 comprises three sets of independently modulatable electrodes: a reference electrode 606, a first lateral electrode 610 and a second lateral electrode 612. Each of these electrodes can, in turn, comprise electrodes that can be independently controlled.

The electrodes 606, 610 and 612 are mounted on a shaft comprising vertical members 608 and plate 602, which provide both physical support as well as electrical connections. Input electrical control is provided through shafts 604, which comprise both physical and electrical connections as well. The number of shafts 604 can be as small as one. The lateral electrodes 610 and 612 correspond roughly to electrodes 210 and 220 of FIG. 4B, and the reference electrode corresponded roughly to the electrodes 190. These electrodes are conveniently comprised of a relatively unreactive metal with high conductivity, such as gold. It is preferable for the lateral electrodes 610 and 612 to be relatively thin, and can also taper at their interior edges to maintain a flat lower surface, allowing electric fields to be controlled near to the bottom of the electrode 600.

The integrated electrode 600 is placed in a microtiter plate well 550 with the bottom surface of the lateral electrodes 610 and 612 placed on to or very near to the bottom of the well 550, with the array 180 of probes 116 sitting between the two lateral electrodes. The electrode 600 performs similarly to the arrangement of FIG. 4B. As the conclusion of each assay, the electrode 600 is removed from the well 550 and washed with strong applied electrical potentials, physical agitation in a solution, and possibly chemical washes in strong acids, oxidizing reagents and other cleaning solutions. It is also within the spirit of the current invention for the electrode 600 to be turned in a roughly circular or in a back and forth motion so as to mix and/or move the target 114 in accordance with the methods described above (e.g. see FIGS. 33A and 33B).

Acceleration of Signal Generation Using Electrophoretic Manipulation

In some cases, the tagged target requires subsequent exposure to substrate in order to generate signal that can be detected by a variety of means. For example, chemiluminescence requires the addition of substrate to enzyme tag in order to generate chemiluminescent signal. Electrophoretic forces can be used to drive enzyme reaction by bringing substrate in close proximity to enzyme and then upon enzymatic conversion of substrate to opposite electric charged state can be use to drive converted substrate away from enzyme rapidly enabling more rapid conversion of the substrate by the enzyme.

Washing-Detection

Overview

Figure 22:
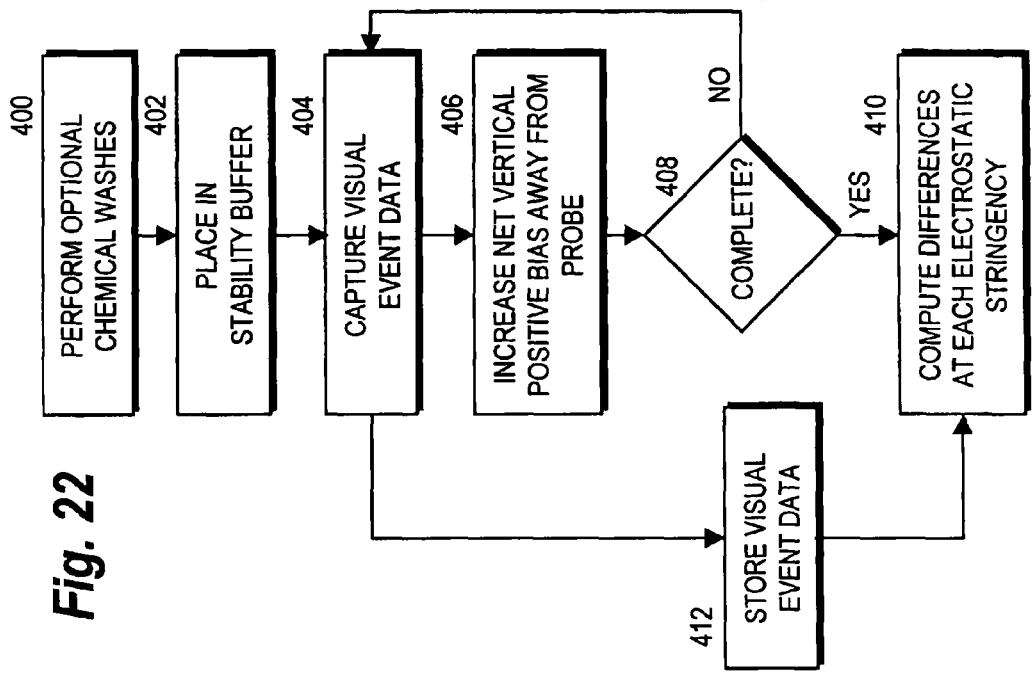
FIG. 22 is a schematic block flow diagram of discrimination using electrophoretic force.

In the sections above, numerous references are made to discriminating specifically bound versus nonspecifically bound material by increasing the bias on an electrode that pulls the electrophoretic tag 270 and the attached target 114 away from the probe 116 with increasing amounts of electrostatic force. This process is described in more detail in FIG. 22, a schematic block flow diagram of discrimination using electrophoretic force.

In a step 400, optional chemical washes are used to remove loosely-bound nonspecifically bound material. These chemical watches can include low-salt, high pH, low pH, or other chemical treatments which lower the binding force between the target 114 and the probe 116.

In a step 402, the chemical washes performed in the step 400 are replaced with a stability buffer that tends to increase the binding force between the target 114 and the probe 116. The stability buffer reduces the chances that the target 114 and the probe 116 will separate adventitiously. It should be noted that in the absence of the step 400, the step 402 can also optionally be eliminated.

In a step 404, the tagged target 275 attached to the probe 116 is visually monitored. In general, this will involve either capturing an image of the array 180, or scanning the array 180 in a manner to be described below. In general, the detection means is matched to the type of indicator component used in the electrophoretic tag 270. It is important that the tagged target 275 which is not associated with the probe 116 is not monitored in this situation. Methods of real-time detection for discriminating bound from unbound electrophoretic tag 270 are described above and below. In a step 412, the visual data that is captured is stored.

In a step 406, the net vertical bias away from the probe 116 is increased in a manner to be described below. This increase will generally be incremental in a manner shown in FIG. 9. In a step 408, it is determined whether or not the maximum stringency from the electrophoretic force has been reached. If it has not been reached, new visual data is captured in the step 404. If the maximum stringency has been reached, the differences in binding for each electrophoretic stringency is computed from the differences between successive captured visual data in a step 410, as described below.

It should be noted that for visual detection, there are a variety of different illumination schemes that can be employed. Some of these illumination schemes require specialized condensers, for use in phase and other types of microscopy. For use in the detection of scattered light, as well as with the use of fluorescent, quantum dot and up-converting phosphors, and certain other modes of detection, the use of other forms of illumination can be used. In many cases, the use of evanescent wave illumination can be of particular use, because the light that does not interact with the target 114 or its tag 270 can be oftentimes prevented from interfering in the detection, and because the only tags 270 that will interact with the light will be those tags that are proximal to the probes 116 on the surface or the substrate. The following discussion will go into detail into the means by which evanescent illumination can be used in visual detection of the tagged target.

Evanescent Illumination Detection Using Parallel Beam Illumination

FIG. 23A is a cross-sectional schematic of an embodiment of the present invention in which a prism 1140 on the top surface is used to introduce light into the slide waveguide 1120. The prism 1140 shown in the figure is a triangular parallelopiped, in which one surface is placed on the top surface 1122 of the slide 1120, and the acceptance surface 1142 faces roughly in the same direction as an edge 1123 of the slide 1120. Roughly parallel light rays 1132, which are preferably nearly perpendicular to the surface 1142 but which can be non-normal and therefore refracted at the surface 1142, enter the surface 1142 with little reflection. These light rays 1132 encounter the bottom surface of the prism 1140, and due to the flatness and juxtaposition of the bottom surface of the prism and the top surface 1122 of the slide, the light rays 1132 bridge the gap between the prism 1140 and the slide 1120, entering the slide 1120. The direction of the light rays 1132 is chosen so that the rays 1132, when encountering the bottom surface 1124 of the slide 1120, will nearly all reflect off of the surface 1124, impinging at greater than the critical angle between the surface 1124 and the medium (generally air) below.

The top surface 1143 of the prism 1140 is chosen so that all of the light rays 1132 that enter the prism 1140 are captured into the slide 1120, and it is of some convenience that the angle between the acceptance surface 1142 and the top surface 1143 of the prism 1140 should be roughly perpendicular. It should be noted, however, that if the apex 1145 of the prism were to be extended far enough along the slide, that raypaths reflected off of the bottom surface 1124, moving upwards to the top surface 1122, could encounter the bottom surface of the prism 1140, resulting in "escape" of the light from the slide. This should be avoided by not extending the apex 1145 too far distally along the slide 1120.

While the parallel rays 1132 are shown to be nearly perpendicular to the acceptance surface 1142, and therefore exhibit almost no refraction, it is within the spirit of the present invention for the light rays 1132 to enter non-perpendicularly to the surface 1142, such that the refracted ray paths have an appropriate trajectory, resulting in nearly total internal reflection within the slide.

FIG. 23B is a cross-sectional schematic of a prism 1140 on the top surface of a slide, in which light is internally reflected within the prism prior to introduction of the light into the slide 1120. In many cases, it is preferential to keep device components roughly perpendicular to one another in order to aid alignment, and in this case, the incident light rays 1132 can be nearly perpendicular to the edge 1123 of the slide 1120 (and therefore parallel to the top surface 1122 of the slide 1120). The acceptance surface 1142 can be parallel to the slide edge 1123, so that the rays 1132 are perpendicular to the surface 1142, thereby limiting reflection at the surface 1142.

After an internal reflection on the top surface 1143 of the prism 1140, the light rays 1132 now have the proper angle into the slide 1120 so as to exhibit total internal reflection. It should be noted that the angle of the ray paths 1132 after reflection on the surface 1143 of the prism 1140 will be twice that of the slope of the prism 1140—therefore, the slope of the top surface 1143 needs to be reasonably small in order to maintain total internal reflection of the raypaths 1132 within the slide 1120.

FIG. 24A is a cross-section schematic of the prism arrangement of FIG. 23, extended so that the disposition of the distal parallel raypaths 1132 can be seen. Parallel ray paths 1132 enter the prism 1140, and then enter the slide 1120. Because of the parallel nature of the ray paths 1132, the pattern of reflections within the parallel walls of the slide 1120, acting as a waveguide, are maintained along the length of the slide 1120. If the rays are bounded by the parallel topmost raypath 1133 and the bottommost raypath 1135, and the top surface 1122 and bottom surface 1124 are parallel, illuminated sections 1146 will be repeatedly interspersed with unilluminated sections 1148 along the length of the slide 1120. This will cause significant differences in reporter 1110 illumination along the slide 1120. This non-uniformity can be to some extent handled by the use of a wide beam of illumination, but it will generally be difficult to modulate beam width so that illumination is precisely uniform Evanescent Illumination Detection Using Convergent Beam Illumination FIG. 24B is the cross-sectional schematic of FIG. 24A, modified by the use of convergent illumination instead of collimated illumination. Converging illumination 1131 enters the prism 1140, during which it is refracted somewhat at the acceptance surface 1142. It is convenient that the point of convergence of the ray paths 1131 not be at the interface between the prism 1140 and the slide 1120, since any imperfections in the glass or contaminants (e.g. dust) at the interface could contribute to light scattering. Scattered light would not necessarily maintain total internal reflection in the slide 1120, and so the point of convergence is preferably either before or after the point at which the light 1131 enters the slide 1120.

Looking at the light in the slide, the trajectories of the topmost raypath 1133 and raypath 1135 can be observed. As can be seen, there is no repeating nature to the areas of illumination and non-illumination for the ray paths 1133 and 1135. Indeed, there is a large range of raypath angles within the light 1131, so that indeed much of the top surface 1122 of the slide 1120 is illuminated after only a small number of internal reflections, and given a very large number of reflections, the illumination of the top surface 1122 becomes nearly uniform. As before, a wider beam will generally result in somewhat more uniform illumination in the case of fewer reflections.

It should be noted that a divergent spread of illumination entering the acceptance surface 1142 would have a similar effect to a convergent illumination, resulting in nearly homogeneous evanescent illumination of the top surface 1122.

Evanescent Illumination Detection Using Non-Uniform Illumination

While the embodiments of FIGS. 23A and B and FIGS. 24A and B can be used with the prism 1140 and/or associated illumination source being in a fixed location, possibly near the end of the slide, it is also in the spirit of the present invention that the prism 1140 and/or its associated illumination source can move to illuminate different areas of the slide, particularly wherein the illumination is intentionally non-uniform.

Figure 24C:
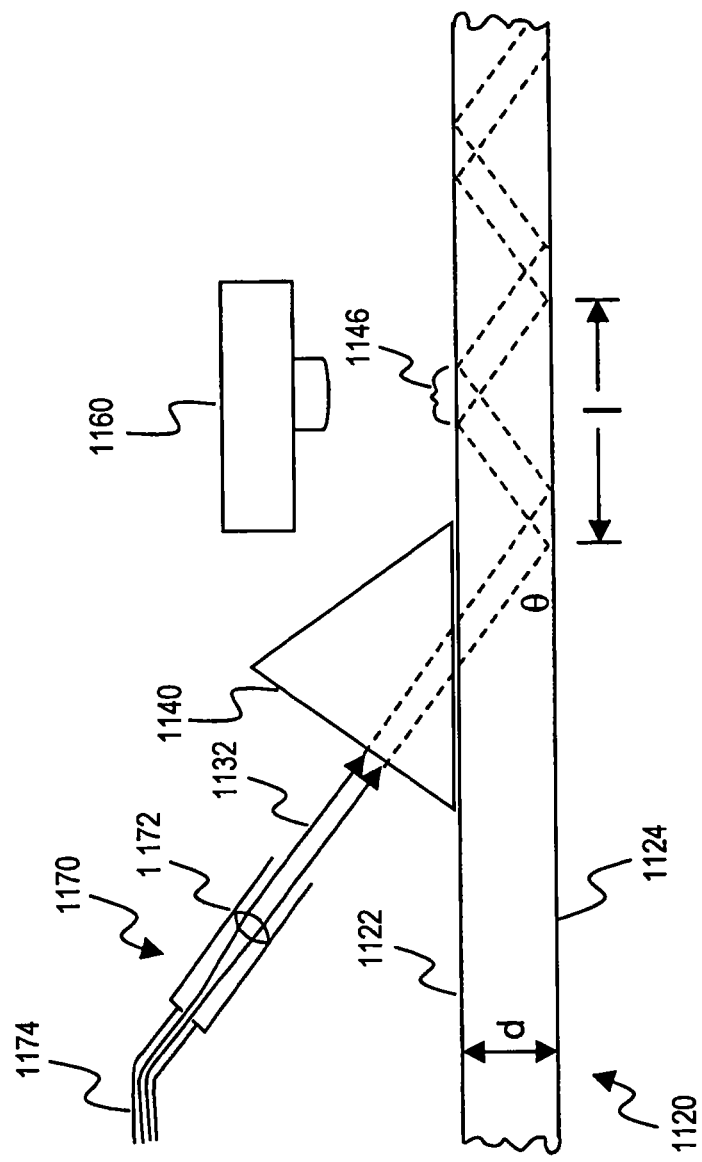
FIG. 24C is a schematic cross-sectional diagram of a slide illuminator in which the slide is non-uniformly illuminated.

FIG. 24C is a schematic cross-sectional diagram of a slide illuminator in which the slide is non-uniformly illuminated. The prism 1140 sits on the top surface 1122 of the slide 1120, and accepts parallel rays 1132 from a collimator 1170. A fiber optic cable 1174 conveys light to the collimator 1170, and light rays diverging from the end of the fiber optic cable 1174 are captured by and converged by a lens 1172, producing collimated rays 1132.

As in FIG. 24A, the light rays 1132 enter into the prism 1140, and thence into the slide 1120, wherein they then reflect multiply against the top layer 1122 and the bottom layer 1124, illuminating the top surface 1122 at regular intervals l. The length l can be computed to be $2*d/\tan \theta$, where d is the thickness of the slide and $\theta$ is the angle complement of the angle of incidence of the light onto the top or bottom surface of the slide.

A detector 1160 is positioned over the spot of illumination 1146 on the top surface 1122 of the slide 1120, and detects a signal resulting from the evanescent illumination of the reporters 1110 residing on the top surface 1122. It should be noted that the detector 1160 could also be positioned over integral multiples of l in distance on the top surface, which is of special convenience should there be topological constraints on the location of the detector 1160 relative, for example, to the prism 1140. It should be understood that the detector technology can comprise both imaging devices (e.g. CCD or CMOS cameras operating with a relatively constant light source) and non-imaging devices (e.g. a photomultiplier tube (PMT) operating in conjunction with a laser scanner illuminating the surface through prism or other coupling).

While this arrangement is effective for illuminating material at a particular position relative to the prism 1140, this arrangement can also be used to illuminate many areas on the top of the slide 1120. This can be accomplished, for example, by sliding the prism 1140 and the associated collimator 1170 in concert over the top surface of the slide 1120. A movement of the prism 1140 and collimator 1170 would result in a concomitant movement of the spot of illumination 1146 of an equal amount.

Alternatively, the prism can be kept in a single location, and the collimator 1170 can be translated horizontally or vertically, maintaining its orientation, such that the point of entrance of the light ray 1132 into the prism is altered. This will translate the light ray 1132 laterally within the slide. Furthermore, rotation of the collimator 1170 would have a translational effect on the position of the spot of illumination 1146. It is also within the spirit of the present invention for there to be a combination of more than one of the movements of the collimator 1170, possibly in concert with movement of the prism 1140, in order to effect translation of the spot 1146 along the top surface 1122.

Evanescent Illumination Detection Using Top Surface Thin Film Waveguide

Another embodiment of the present invention is to make a very thin waveguide, rather than using the slide, which generally has a thickness of a millimeter or larger. This can be accomplished in a variety of ways. For example, the slide itself can be constructed as a film, possibly of a flexible high index plastic material. This may not be convenient in certain applications, including such cases where the film is to maintain structural rigidity; the plastic material is inappropriate for the biological and chemical reactions used in the detection process, and allowing the material to bend will potentially allow light to escape when internal reflection angles become less than the critical angle.

An alternative embodiment is shown in FIG. 25A, a schematic cross-section of a high index thin film waveguide 1180 deposited on a slide substrate by physical vapor deposition (e.g. sputtering or evaporation), by chemical vapor deposition, by spin coating, dip coating, or by other means that provides a film of roughly uniform thickness. Furthermore, graded index of refraction thin films can be generated using sol-gel and ion exchange methods. A review of the methods for producing such thin waveguides is provided in "Planar integrated optical methods for examining thin films and their surface adlayers" by Plowman, Saavedra and Reichert (Biomaterials (1998) 19, pg. 341-355).

The thin film waveguide 1180 is comprised of a material that has a substantially higher index of refraction than the underlying slide 1120. The material is conveniently $Ta_2O_5$, which is commonly used in the high-index layers in the production of thin-film interference filters, although other materials can be used, such as $TiO_2$, silicon nitride, ion-doped silica, and ion-doped glasses. The thickness of the waveguide is generally on the order of a wavelength of the guided light, which in this case will typically be in the visible or ultraviolet (UV) range, and can conveniently be on the order of 100-5000 nm, and is more preferably 150-2000 nm. Because of the small thickness, only one or a few modes are transmitted in the waveguide (i.e. single-mode) as opposed to the multimodal transmission of light in a thick waveguide (e.g. the slide).

Coupling of the incident illumination into the thin film waveguide can be accomplished in a number of ways. FIG. 25A is a schematic cross-section of an end-illuminated thin-film waveguide 1180 integrated with a slide 1120. A fiber optic cable 1174 transmits light along a single-mode fiber 1175, which terminates in a coupler 1182. The coupler 1182 can also be seen in FIG. 25B, a schematic top view of the coupler 1182 and the slide 1120 of FIG. 25A. Light exiting the fiber 1174 encounters a conditioning lens 1177 that is used to adjust the divergence of the emergent light rays, and may be either convergent or divergent. The light is then passed through a cylindrical lens 1178 to converge the beam in a single dimension, oriented in such a way that the emerging light lines up roughly with the waveguide 1180. Optimally, the focal point is roughly coincident with the edge surface of the waveguide 1180. The beam so constrained gains significant admittance into the waveguide 1180.

The coupler 1182 encapsulates the terminus of the fiber optic cable 1174, as well as the conditioning lens 1177 and cylindrical lens 1178. A positioning lip 1183 on the top front of the coupler 1182 is used to position the coupler 1182 onto the slide 1120 with the optics arranged to couple light into the waveguide 1180.

It should be noted that the optical arrangement of lenses can be varied within the teachings of the present invention. For example, the fiber optic cable can be butt-end juxtaposed directly to the edge of the waveguide 1180. Alternatively, the conditioning lens 1177 can be left out, in part depending on the placement of the cable 1174. Also, the cylindrical lens 1178 can be omitted, given a conditioning lens 1177 that converges on the edge of the waveguide.

It should be noted that there can be some leakage of the beam either above the waveguide 1180 or into the slide 1120, which for very narrow waveguides can comprise the majority of the light from the cylindrical lens 1178, since coupling tends to be inefficient. With leakage above the waveguide, the coupler 1182 has an overhang that lies on top of the waveguide 1180, both helping in aligning the coupler 1182 so that light from the fiber optic cable 1174 enters the waveguide 1180, and secondly, blocking light escaping from the coupler 1182 forwards. With leakage into the slide 1120, small amounts of light that leak into the slide 1120 will tend to be constrained within the slide 1120 (acting as a waveguide). Other light with a higher angle (so that it doesn't reflect) will first encounter the bottom surface of the slide 1120, where it will escape and also not affect the evanescent or other illumination above the waveguide 1180.

Figure 25C:
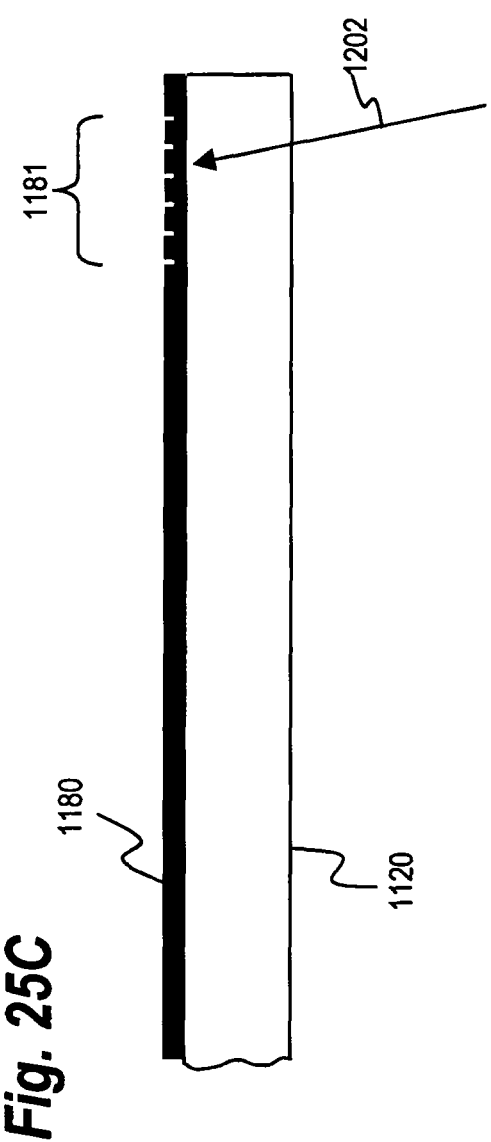
FIG. 25C is a schematic cross-section of a thin film waveguide wherein light is coupled to the waveguide via a grating.

An alternative method of coupling the illumination into the thin film waveguide 1180 is to place a grating onto the surface of the waveguide 1180. The principle of operation and construction of such a grating coupler is provided in Plowman, et al. (reference provided above). FIG. 25C is a schematic cross-section of a grating 1181 on the surface of the waveguide 1180, with incident illumination thereby captured into the waveguide 1180. The grating is positioned on the top surface of the thin-film waveguide 1180, with input light 1202 directed from below onto the waveguide 1180. The grating can also be positioned at the waveguide/substrate interface, or at any interface in a multi-layer waveguide 1180. Furthermore, the waveguide 1180 can be illuminated from above as well as below.

Figure 25D:
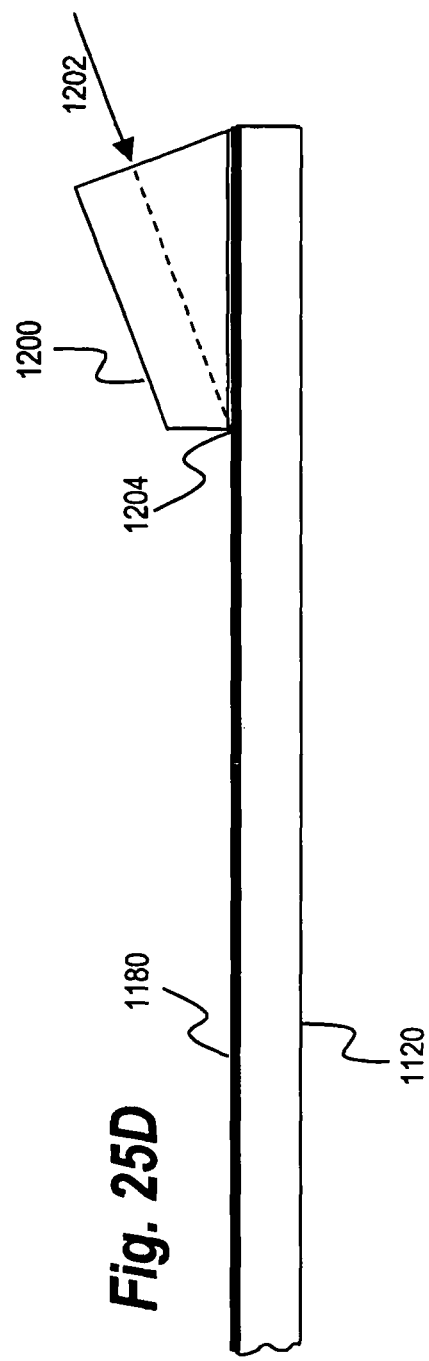
FIG. 25D is a schematic cross-section of a thin film waveguide wherein light is coupled to the waveguide via a high-index material prism.

A prism can also be used to couple light into a thin film waveguide 1180. FIG. 25D is a schematic cross-section of a thin film waveguide 1180 wherein light is coupled to the waveguide 1180 via a high-index material prism 1200. It should be noted that the input light 1202 enters the waveguide 1180 close to the edge of the prism 1200, since high index of refraction prism 1200 material that overlies the waveguide 1180 beyond the point of coupling will permit light in the waveguide 1180 to escape. The input light 1202 can, therefore, either be a narrow, collimated beam that is directed at the vertex 1204 of the prism 1200, or can be a beam of light that converges near the vertex 1204 (e.g. via a spherical convex lens or plano-convex cylindrical lens).

It should be noted that the incident light 1202 need not be roughly perpendicular to the face of the prism 1200, and it can refract at that surface so that it is at the proper incident angle into the waveguide 1180 at the proper location. It should also be understood that it is within the teachings of the invention that the prism 1200 for waveguide 1180 coupling to have a triangular, trapezoidal, or other cross-section.

Evanescent Illumination Detection Using Single Bounce Non-Waveguide Architectures In the embodiments above, illumination that is captured into the waveguide 1180 is introduced in the direction of the top surface of the slide 1120, from which the detection is performed. It should also be noted that evanescent waves can be created through systems in which the light is not captured into a waveguide 1180, but simply reflects once against the top surface of the slide 1120. At the location of the reflection, an evanescent wave is created. It should be noted that this architecture, though organized in a somewhat similar architecture, shares considerable theoretical overlap with the embodiment of integral reflections as in FIG. 24C, except that the light, after illumination of the appropriate top surface location, is not constrained with the slide 1120.

FIG. 26A is a schematic cross-section of evanescent illumination of a region without use of a waveguide 1180. A trapezoidal prism 1190 is juxtaposed to the bottom surface 1124 of the slide 1120. Incoming light 1132 enters the prism 1190 on an acceptance surface 1192, and transverses the prism 1190, encountering the slide on its bottom surface 1124. The index of refraction of the prism 1190 and the slide 1120 are chosen to be similar, so that the light enters the slide 1120, generally with little or no refraction.

The light 1132, refracted at the boundary of the prism 1190 and the slide 1120, traverses the slide 1120 where it encounters the top surface 1122 of the slide 1120, and the angle of incidence is chosen to be greater than the critical angle at that surface 1122. Thus, the light reflects off of the top surface 1122. As shown in FIG. 26A, the light 1132 then re-enters the prism 1190 and then exits via emergent surface 1194. It should be noted that the goal is to illuminate a region of the top surface 1122 of the slide 1120, so that the disposition of the light after the reflection on the top surface 1122 is of less concern. Thus, instead of a trapezoidal prism 1190, the prism can be truncated such that light entering the slide 1120 from the prism 1190 then remains in the slide 1120, with the slide 1120 then functioning as a wave guide.

Indeed, it can be of some convenience for the prism 1190 to extend only to the point where the light 1132 enters the slide 1120, being otherwise truncated. This arrangement provides more room for a detector to be mounted underneath rather than above the slide, which may be useful in certain applications. Alternatively, given proper stand-off optics, detection can be made through the prism 1190.

Alternatively, the prism 1190 can be constructed so as to allow a window for detection. FIG. 26B is a schematic cross-section of evanescent illumination according to FIG. 26A, in which the prism 1190 has a window 1193 through which the detector 1160 detects events on the top surface 1122 of the slide 1120. The window 1193 is either fabricated during prism 1190 construction, or is ground into the prism 1190 after the prism 1190 is fabricated. For example, the window 1193 can be produced by a conical grinding wheel, opening a hole directly below the area illuminated on the top surface 1122 of the slide 1120. Within the teachings of the present invention, the window 1193 can be of many topologies, including conical, rectangular box, trapezoidal trough, or complex geometries combining different shapes. Furthermore, instead of a window 1193, the prism 1190 can be replaced with two "half-prisms" (or entry and exit prisms), each comprising a region that couples with the slide 1120, and the space between the half-prisms comprising a "window" area where a detector 1160 can be placed.

Within this window 1193, the detector 1160 can operate from below without interference from the prism 1190, or can be mounted within the profile of the prism 1190 should the working distance of the detector 1160 be limited.

It should be noted that the indices of refraction in the slide 1120 and the prism 1190 can differ with the provisos that the angle of light at the bottom surface 1124 is below the critical angle, allowing the light to enter the slide 1120, and that the refracted light in the slide 1120 encounters the top surface 1122 above the critical angle so that it reflects off of the top surface 1122. Furthermore, however, as the angle of the light at the boundary of the prism 1190 and the slide 1120 approaches the critical angle, the partitioning of light between transmission and reflection becomes increasingly biased towards reflection, so that it is preferable for the difference in the indices of refraction between the prism 1190 and the slide 1120 to be minimized.

In many cases, the area of detection on the slide 1120 is large compared with the area illuminated by the illuminator and the area of illumination on the slide 1120 must be moved relative to the slide. There are three primary means of accomplishing this goal. In the first, the prism 1190 and detector 1160 maintain fixed positions, and the slide 1120 moves. In the second, the detector 1160 and the illumination move independently—the position of the spot of illumination can be adjusted either by translating the position of the collimator 1170, or, if the collimator 1170 is mounted to the prism, by moving the prism 1190. The arrangement of FIG. 26B has both the collimator 1170 and the detector 1160 being placed in fixed position relative to the prism 1190, such that movement of the prism 1190 naturally and conveniently repositions the illumination and detection means in concert, maintaining a fixed relationship. It should be noted that mounting of the illumination and detection means to the prism 1190 does not depend on the presence of the window 1193, and can be accomplished conveniently with a trapezoidal prism, such as in FIG. 26A, with the detector 1160 mounted to the flat bottom surface of the prism 1190.

Coupling between the prism 1190 and the slide 1120 can be difficult, given that it is interfered with by dust and other particles, and the tight coupling makes difficult the separation of the two flat interfaces in an operational device. Often, an index matching fluid with an index of refraction similar to that of the glass of the slide 1120 or the glass of the prism 1190 is used, but this arrangement suffers from dust and other particles that can accumulate within the fluid. Furthermore, excess fluid transferred to the slide (e.g. by smearing or being expressed from between the slide 1120 and the prism 1190 can potentially allow light to leak from the waveguide.

It should be noted that there are three distinct surface areas through which the light interacts with: the surface 1192, the surface 1124, and the surface 1192. These surfaces can be present on either two different components (as in FIG. 26A), on three different components (as in FIG. 26B), or can alternatively be on a single component, as would be the case in a molded single piece that could have a cross-section substantially similar to that of the FIG. 26A or B. All of these arrangements are within the spirit of the present invention.

An alternative arrangement is presented in FIG. 27A, a schematic cross-section of a prism &190 that couples light using a flexible coupler 1250. The prism 1190 couples the light ray 1132 into the slide 1120. To facilitate the coupling, the coupler 1250 is positioned between the prism 1190 and the slide 1120. The coupler 1250 is made of flexible transparent material and its thickness can range from hundreds of microns generally up to 2 millimeters. The composition of the coupler 1250 can include optical curing gels such as NyoGel, flexible optical adhesives, which can be UV cured, as well as transparent, curable silicone rubbers. It is preferable that the index of refraction of this coupler 1250 should be similar to that of the slide 1120 material or the prism 1190 material, or be of intermediate refractive index. In general, the coupler will be attached to the prism 1190, and can be molded as an adhesive onto the prism 1190.

In order to reduce the potential for air being trapped between the coupler, it is convenient for the prism 1190 with the attached coupler 1250 to be brought onto the slide 1120 at a slight angle, so that air will be pressed outward from the initial point of contact as full contact is made between the coupler 1250 and the slide 1120. Alternatively, the bottom face of the coupler 1250 can be slightly curved in order to take account of this problem. FIG. 27B is a side view schematic of a prism 1190 with a curved face coupler 1252. Given curvature on a bottom face 1254, as shown in the figure, as the prism 1190 is lowered onto the slide 1120, air will be forced towards the part of the coupler 1252 for which contact is not yet completed. The difference in thickness from one end of the coupler 1252 to the other end of the coupler 1252 does not need to be large in this instance, though it is preferably greater than 0.5 millimeter.

Other Methods of Illumination and Detection

Other methods of realtime detection are convenient within the spirit of the present invention, including confocal microscopy in conjunction with scattering, fluorescence, up-converting phosphors, quantum dots or other indicators, as well surface plasmon resonance (SPR). Confocal microscopy takes advantage of a very shallow depth of field, such that indicator tags that are drawn away from the probes 116 are out of focus and the light energy is either dispersed or reduced through spatial filtering. Imaging similar to confocal imaging is also possible using very large numerical aperture objectives which also have shallow depth of field. Surface plasmon resonance uses an arrangement of components similar to that of detection using single bounce non-waveguide architectures, as described above, in which the top surface of the glass is coated with a reflective, metallic surface which is conveniently gold. In this case, the amount of light reflected by the gold is affected by the presence of material bound to the probes 116. Surface plasmon resonance is well suited to the present invention, in that the gold surface can serve both as a reflective surface, as well as the electrode for use in reaction acceleration and binding force discrimination.

The methods above have the advantage that targets 114 binding to the probes 116 are visible and distinguishable even in the presence of unbound target 114, since only that target that is bound is visible. However, it is further within the spirit of the present invention for alternative arrangements of illuminators and detectors, given that unbound targets 114 can be removed from the region of the probe 116, either by removal of the solution in which the targets 114 are provided (e.g. as shown below in the case of chambers for the detection of bacteria), or through the sequestration of the targets 114 in another region. The latter method can involve, for example, the electrophoresis of target 114 to another electrode that is not in the optical path either of the detector and/or illuminator.

Some of the arrangements that are available within the present invention can be understood with reference to two parallel substrates (a lower and an upper substrate) with electrodes on these substrates facing each other across an internal gap. We can then define from bottom to top four different surfaces—the lower bottom surface, the upper bottom surface (i.e. with an electrode on which probe is deposited), the lower top surface (i.e. with an electrode without probe) and an upper top surface. The detector in general will be either below the lower bottom surface or above the upper top surface (i.e. it is not in the gap between the two substrates).

If the detector is below the lower bottom surface, then the electrode on the upper bottom surface will generally be transparent, except in the case of surface plasmon resonance. In the case of surface plasmon resonance, the detector must also be below the lower bottom surface. The illumination can either be also below the lower bottom surface, passing through the bottom substrate electrode, with back-scattered light, evanescent light (which reflect off of the upper bottom surface), or light that is meant to excite fluorophores, upconverting phosphors or quantum dots. Alternatively, the illumination can be from within the bottom substrate, as described above. Also, the illumination can be from within the gap between the two substrates, which would generally be best for a light scattering application. Alternatively, the illumination can be from above the upper top surface, transiting through the top substrate, through the gap, and then to the upper bottom surface where it interacts with the target or a tagged target. In those cases, once again, the detector can detect either scattered light (e.g. forward scattered light), or fluorophores, upconverting phosphors, or quantum dots, or the samples can be viewed for brightfield, darkfield, phase or other forms of microscopic imaging (generally using light from a condenser).

If the detector is above the upper top surface, receiving light from the tagged target, in this case the electrode on the upper bottom surface need not be transparent, while the electrode on the lower top surface should be transparent. If the upper bottom surface is opaque, then the illumination must either come from above that electrode surface, or be generated at the tagged target, as might occur with chemiluminescence. With an opaque upper bottom surface, the illumination can be within the cap (most likely for scattered light analysis), and otherwise most likely for scattered light or excitation illumination for fluorophores, upconverting phosphors, or quantum dots. If the electrode on the upper bottom surface is transparent, however, light can be transmitted from below, including by evanescent wave illumination as described above.

While the detector is generally an imager (e.g. a CCD or CMOS camera), it can also comprise a laser scanner with a PMT or other light gathering device. In certain cases, the detector can also entail a general light gathering device (PMT, photodiode, photoresistor) with diffuse illumination. The latter case will be primarily used in those cases where averaged signal over an area provides suitable signal, as discussed below.

When using a CCD or CMOS camera, the information is obtained pixel by pixel, generally in 8-12 bit grayscale, though in certain cases (e.g. with indicators color-coded for different targets) an RGB image can alternatively be used. In those cases where it is useful or important to register individual target binding events, there are potentially two modes of operation. In a first mode, target binding is limited so that only a fraction of the pixels register with a signal—most pixels are at some background level, so that the change from the background level to a level significantly above background level at a pixel denotes a binding event. Depending on the size of the target (and/or its tag), a single binding event may correspond to an increase in the signal above background at a number of different contiguous pixels (most image processing software has routines that can group together regions of contiguous pixels into discrete "events"). In this case, the dynamic range of the system ranges from less than 100 targets and as small as 1 target (and is limited by the statistical variation of the small number of targets), to as roughly as high as the number of pixels in the camera divided by the average number of pixels per target (with a floor of one), and then divided by a factor approximating 10, which is the "saturation point" at which new targets would more likely overlap with existing targets rather than being deposited on areas with approximately background levels of signal. For a camera with 5 megapixels, and a target that spans approximately 2 pixels, this corresponds to a dynamic range that spans roughly from 10 to 250,000 targets, or a range span of 25,000. This range is adequate for many applications, and in those applications for which a greater dynamic range is required, multiple dilutions can be used.

In a second mode, the differences between a single target and different numbers of targets within a pixel can be discriminated. For example, if the signal is measured with an 8-bit pixel, with 256 levels, and a background signal is 12, then a single binding event might average 62, two targets in the same pixel might average 112, and so on. In this case, the dynamic range is far higher, and is roughly the number of pixels times the number of levels that can be discriminated divided by the average number of pixels per target (with a floor of one) and further divided by a factor of approximately 10, representing the saturation at which additional target binding could raise levels in a significant number of pixels above the pixel saturation level. In this case, with 5 levels being able to be discriminated and an average number of pixels per target being 1, the dynamic range is still roughly a minimum of 10 (limited by solely statistical considerations), but the upper level now extends to approximately 2.5 million, or an additional ten fold dynamic range from the previous example. The difficulty encountered with this second mode of operation is that it becomes increasingly difficult to distinguish specific from non-specific binding on the basis of image analysis—both because on average each target spans a smaller number of pixels, and because the contrast between different levels is generally poor.

While these methods can distinguish individual binding events, it should be noted that the greatest value of counting individual binding events occurs when there is significant non-specific binding or other forms of noise. For example, low level background noise can sum over a large area to comprise a large noise signal, for which a large amount of specific signal is required to show above background. However, in cases where the signals are generally large above background, it can be convenient to use a signal summing method, wherein the signal is summed either by adding the signal values at each pixel, or by using an analog summing technique such as the use of a photodiode or a photoresistor or a photomultiplier tube (PMT).

Controlled Washing Dynamics

In the following discussion, electric potential between the electrodes, and through potential the resultant electrophoretic force, is used as an example of a vertical force on the target 114. It should be noted, however, that the modulation of force can also be effected in similar manners when using other means of force application, such as magnetic force (e.g. on tags 270 comprising magnetic particles). In addition, the forces can also include horizontal forces, applied such as through the application of lateral electrophoresis, lateral application of magnetic fields, and different means of application of lateral forces. It should be noted that the application of these lateral forces can also include the introduction of an air bubble or similar air-water interface, since these interfaces apply very large forces through surface tension on targets 114. It should be noted that the application of these forces can be shaped, so that the forces are neither vertical nor horizontal, but can have aspects of both, such as shown in the FIG. 5.

Figure 28B:
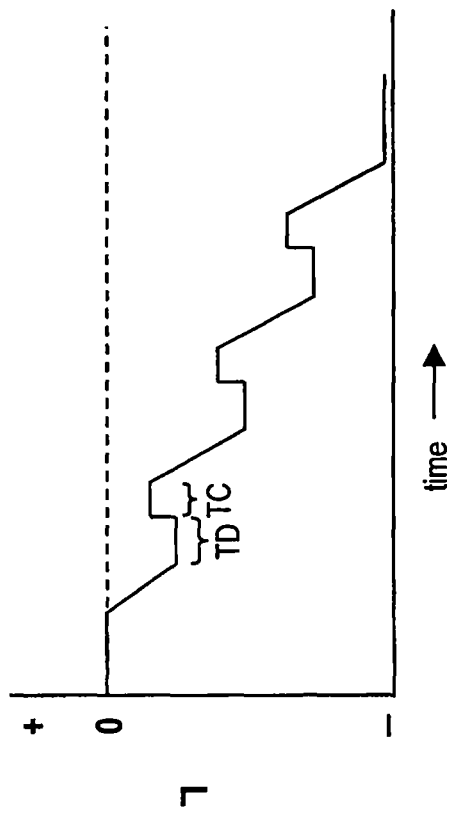
FIG. 28B is a graph of the washing potential as a function of time for a ramped washing function.
Figure 28A:
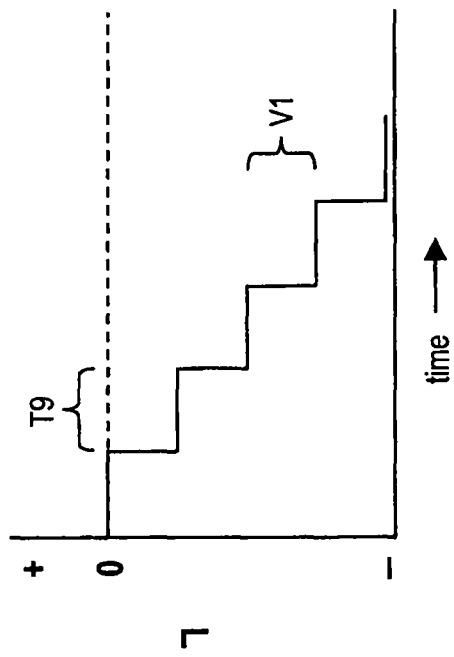
FIG. 28A is a graph of the washing potential as a function of time for a simple step washing function.

As described in FIGS. 28A and 28B, the washing force is increased incrementally over time, with realtime detection of binding occurring as described above. The dynamics of changing the washing stringency is done in fixed incremental steps in its simplest form. FIG. 28A is a graph of the washing potential as a function of time for a simple step washing function. The horizontal axis is time, and the vertical axis is the potential of the probe electrode 200 relative to that of a reference electrode. At the initial period, the potential is zero or low, in which case there is no washing force. The detected signal represents the sum total of the specific and the nonspecific binding of tag target to the probe 116. After a time T9, the negative potential on the probe electrode 200 is increased by a value V1 in rough step function. After some period at this higher potential, generally on the order of hundreds of milliseconds (though as small a period as tens of milliseconds and as large a period as seconds), realtime detection occurs. The step increase in the negative potential is repeated a number of times until the maximum required potential occurs. The maximum potential will generally be currently determined as the force with which all specifically bound tag target is released from the probe 116. The number of steps of potential increase is user selected, and will be determined by factors such as the range of different binding forces between tag targets and probes 116 present on the electrode 200. It should be noted that the potential steps need not be equal in size, nor do the time periods T9 need to the necessarily equal as well.

Figure 29B:
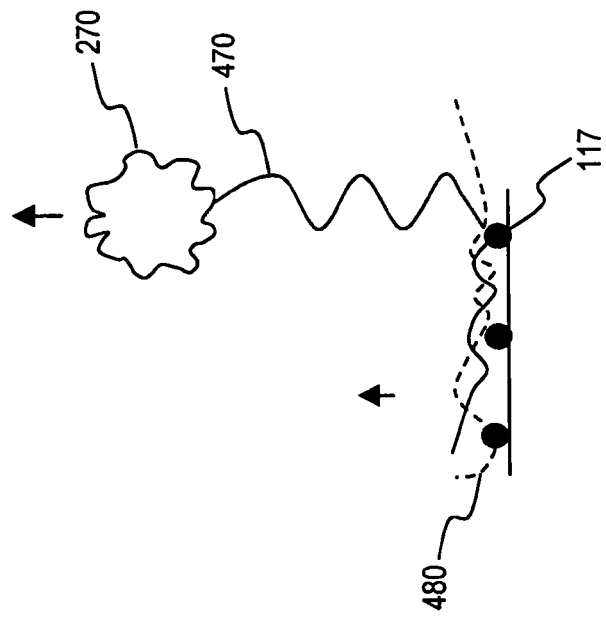
FIGS. 29A-B is a schematic diagram of a tagged target comprising a single-stranded DNA target binding to a complementary DNA probe, which is bound to the substrate at one or more points of attachment.
Figure 29A:
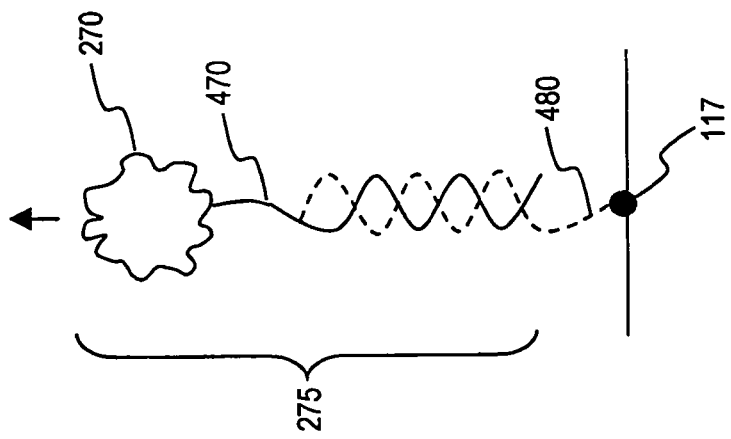

The binding between the tagged target 275 and the probe 116 can be complex. Consider FIG. 29A, a schematic diagram of a tagged target 275 comprising a single-stranded DNA target 470 binding to a complementary DNA probe 480, which is bound to the substrate 120 at a single point of attachment 117. As can be seen, electrophoretic force exerted on the electrophoretic tag 270 will tend to unravel the DNA target 470 from the complementary DNA probe 480 in a straightforward manner. FIG. 29B is a schematic diagram of a tagged target 275 comprising a single-stranded DNA target 470 binding to a complementary DNA probe 480, which is bound to the substrate 120 at multiple points of attachment 117. In this case, force exerted on the electrophoretic tagged 270 does not necessarily directly result in release of the target 470, because the target 470 is constrained by the probe 480 within the points of attachment 117. Because of the topological constraints and the multiple points of force, the target 470 must be gently removed from the probe 480. This can be accomplished by various means as described below.

It should also be appreciated that the electrodes of the cell can potentially participate in electrochemical reactions that limit the potentials at which the cell can be operated. For example, if the electrodes comprise indium tin oxide, potentials of just over 1 volt can result in deterioration of the electrode. If larger voltage potentials are required in order to separate the target 114 from the probe 116, the voltage potentials can be applied for a very short period—which can be ten of milliseconds, and even more preferably one millisecond, and even more preferably 100 microseconds, during which time the target 114 can be separated from the probe 116 but which is of such a short duration that relatively little reaction of the electrode material can occur. In intermediate periods, wherein a voltage potential is maintained that does not cause electrochemical reactions involving the electrode, the amount of target 114 attached to the probe 116 can be measured.

FIG. 28B is a graph of the washing potential as a function of time for a ramped washing function. In this case, the overall potential between different steps of washing is the same potential difference V1 as used in FIG. 28A. However, instead of a step function, the potential is gradually raised over time. The increase in potential can be linear, exponential, or otherwise. Alternatively, the increase in potential need not be monotonic, and can comprise a series of increasing and decreasing steps arriving at the desired potential for the intended stringency.

Furthermore, the intermediate potential "plateaus" are divided into two discrete time steps. In a first time step, TD, the target 114 and the probe 116 are allowed to dissociate at the higher potential. However, the rate of dissociation during the detection process is desired to be reduced, so that the potential can be reduced during a time TC (e.g. during image capture) while the bound target 114 is detected.

Figure 30B:
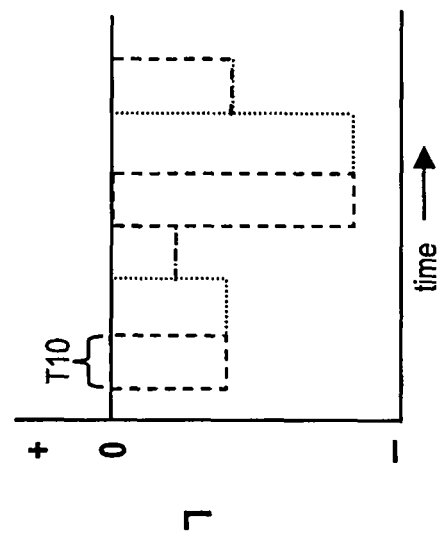
FIG. 30B is a graph of the potential of electrode relative to the two reference electrodes as shown in FIG. 30A for two steps in the washing stringency.
Figure 30A:
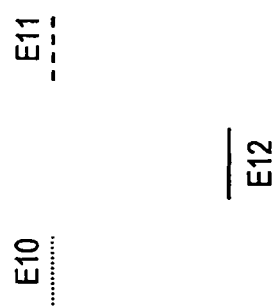
FIG. 30A is a schematic side view diagram of two reference electrodes relative to the probe electrode.

The direction vector of the electric field used for washing need not be in one direction, but can be usefully varied to help remove the target 470 from the probe 480, as illustrated in FIGS. 30A and B. FIG. 30A is a schematic side view diagram of two reference electrodes E10 and E11 relative to the probe electrode E12. FIG. 30B is a graph of the potential of electrode E12 relative to the two reference electrodes E10 and E11 as shown in FIG. 30A for two steps in the washing stringency. The relative potential of electrode E10 to electrode E12 is given by a dotted line, the relative potential of electrode E11 to electrode E12 is given by a dashed line, and wherein the relative potentials overlap, a dashed-dotted line is shown. For an initial period, the potential relative to electrode E10 is high, and the potential relative to electrode E11 is zero. Next, the potential relative to electrode E11 is high, while the potential relative to electrode E10 is small. Next, the potentials for both electrodes E10 and E11 are placed at an intermediate level. During these three steps, the electric field direction varies from pointing at the electrode E10, to the electrode E11, to a position intermediate between the two. Target 470 that is sterically enmeshed either with the probe 480, or alternatively with the linkers 118, or other material that is at the surface 120, can generally be pulled in the direction that will release it, whether it is bound specifically or nonspecifically. In subsequent time steps T10, as shown in the figure, higher forces in the different directions can be applied. In addition, instead of applying the forces a step functions, they can be applied as a ramped time functions (linear, exponential, or other) and they can also be non-monotonically applied and applied over varying durations to provide the desired effect.

It should be noted that the potential needed to separate the tagged target 275 from the probe 116 depends on the charge on the electrophoretic tag 270. Furthermore, it can be less convenient if the potential needed to be applied varies over large orders of magnitude over the probes 116 affixed within an array 180, since a larger number of different stringency washes will be required. Thus, it is convenient if the electrophoretic tag 270 is matched roughly to the binding force between the associated target 114 and probe 116. For instance, a target-probe pair with a stronger binding force will be conveniently paired with an electrophoretic tag of larger electrostatic charge, so that more roughly the same voltage potential would need to be applied to separate the target-probe pair.

While the washing dynamics of the previous section deal with electrostatic or electrophoretic forces, other discriminating forces and conditions can be applied with the use of realtime detection, including conductance, pH, solvents, and competing ligands. Such conditions can further be applied either in a stepwise fashion, or in a continuous gradient, and can be applied using mechanical pumps, electroosmotic mechanisms, or other transport mechanisms. Furthermore, these conditions can be applied in combination with each other, or also in combination with the electrostatic and electrophoretic forces described above. Because it is difficult at times to reproducibly change, for example, the pH of a solution in a gradient fashion, especially in the very small formats used in many of the assays of the present invention, it is useful to place within the array 180 a number of target 114-probe 116 pairs whose binding is disrupted at known conditions, serving thereby as internal controls to verify that specific conditions are being reached.

Detection of Organisms and Determination of Anti-Organism Agent Sensitivity

Overview

It is important to determine the identity of bacteria with regards to food pathogens, biological warfare agents, and a variety of animal and human diseases. In addition to the rapid and sensitive detection of these bacteria, in the case of animal and human disease, it is of great benefit to additionally determine the susceptibility of the microorganisms to antibiotics, antifungals, and other medical agents. Bacteria that are of particular interest are human pathogens, including bacteria from the genera *Pseudomonas, Stenotrophomonas, Acinetobacter, Enterobacter, Escherichia, Klebsiella, Proteus, Serratia, Haemophilus, Streptococcus, Staphylococcus, Enterococcus, Mycobacterium, Neisseria*, and other human pathogens encountered in medical practice. The present invention is well suited to this application.

It should be noted, however, that the detection system and methods are not limited to bacteria, and can be used as well in the detection of fungi (e.g. *Candida* and *Aspergillus*), virus, mycoplasma, and other types of organisms, and can include the detection of animal cells, such as in the detection of metaplastic or other disease cell types. In the discussion below, the use of bacteria is meant to be as an example only, and that the discussion is to include these other organisms as well. It should be noted that in the discussion above, the target 114 can be generally without limitation bacteria and other organisms, as discussed below. The discussion below expands the detail and introduces new methods and devices with which the application of the methods and devices above are applied to bacteria and other organisms.

FIG. 31 is a block flow diagram of the process for determining the identity, number and antibiotic susceptibility of bacteria in a sample. In a first step 700, the sample is optionally concentrated, which is necessary in many cases where the bacterial sample is present in a large liquid volume. Such a step 700 will generally be performed when the sample is in a volume of greater than 10 milliliters, and often when the sample is in a volume of as little as 500 microliters. The reason for this is that, depending on the system, the sample volume to be placed into the detection system can be limited to as little as 100 microliters, although other systems can handle much larger amounts, with samples in the many milliliters. The concentration performs two functions. Firstly, the ratio of number of bacteria to the volume of the sample is increased, so that the greatest possible fraction of the sample can be used in the system. A second reason is that the bacteria may be in a liquid whose electrical or other properties are incompatible or non-optimal for the detection system. For example, if electrophoretic methods are subsequently to be used, the efficacy of such methods is improved generally by the use of low electrolyte buffers. In such case, the bacterial sample liquid will be replaced by a liquid that is more compatible with the system In a step 710, the bacteria are transported to a detection zone, which is where the locator for use in later steps is located. The bacteria at this point are still not immobilized, but are free to move about in a three-dimensional volume. The transportation to the detection zone can be accomplished in many different ways, including active physical transport by pumps (e.g. positive displacement syringe pumps, pneumatic pumps, peristaltic pumps, or others), by electroosmosis, by gravity, by electrophoresis of the bacteria, or other means. In addition, the concentration step 700 can involve the concentration of the bacteria directly in the detection zone, such as centrifugation of the bacteria into the zone, followed by resuspension.

In a step 720, the bacteria are immobilized onto the detection surface. The detection surface, it should be noted, can either be specific for a subset of bacteria (e.g. through the surface attachment of antibodies specific for one or more bacteria), or it can alternatively be non-specific such that most or all bacteria in a sample will bind to the surface.

It should be noted that there can be a single zone or multiple zones within the system. For example, in one embodiment of the system, there can be a zone specific for each bacteria strain—distinguished by the properties of the respective detection surfaces—and the system can comprise even dozens of separate zones. Alternatively, all of the bacteria can be attached at a single non-specific zone. Also, there can be a combination of specific and non-specific detection zones, where the bacteria are first captured at specific detection zones, to be followed by non-specific capture of all of the bacteria that were not captured in the specific detection zones. It should be noted that if there are multiple zones, the bacteria may need to be transported from one detection zone to another detection zone between attachments of the bacteria to the respective detection surfaces.

Now that the bacteria are attached to the surface, their arrangement is roughly in a two-dimensional distribution. It should be noted that the term two-dimensional is meant to include some reasonable degree of vertical depth, given that the attachment surface can be up to microns in depth (e.g. through the incorporation of polymer hydrogel or similar materials). However, given that the detection means can incorporate microscopic detectors with limited depth of field, it is preferable for the surface to have a topological depth of no more than 5 microns, and even more preferable for the depth to be less than two microns.

The attachment of the bacteria to the surface can occur through diffusion of the bacteria to the surface, where they are attached specifically or non-specifically. However, because diffusion can be slow on the time scales generally desirable in such a system, active means are preferred for the attachment of the bacteria. These means can comprise the use of electrophoresis or dielectrophoresis of the bacteria to the surface, the use of centrifugal forces, or even the filtration of the bacteria onto the detection surface, wherein the surface is porous but with pores smaller than that of the smallest diameter of the bacteria. Once the bacteria are in direct contact with the surface, it is generally arranged that the attachment process is rapid, occurring in a matter of seconds or minutes, whether the attachment is specific or non-specific, although longer times of attachment are allowed within the present invention. It should be noted that bacterial attachment generally increases over a period of time (minutes to hours), both with the secretion of attachment molecules from the bacteria, as well as an increase in the number and strength of attachments that normally accrue even with the attachment of non-living material to surfaces—however, the attachment above is meant to indicate attachment such that the typical forces of diffusion, convection, fluid flow through the system, and such are insufficient to dislodge the bacteria from the surface, and that specific application of forces desired to remove the bacteria is required.

In cases where specific attachment of bacteria is desired onto the detection surface, it is useful to remove those bacteria that are non-specific attached to the surface. This is generally accomplished by the assumption that all of the bacteria that are attached specifically are attached with a relatively narrow range of attachment forces. Thus, forces outside of that specific-attachment range will either remove the non-specifically attached bacteria (i.e. those bacteria that are attached with a lower force) or will remove specifically attached bacteria, but not others (i.e. those bacteria that are attached with a greater force). The types of forces that can be employed to this effect include electrophoresis, dielectrophoresis, centrifugal force, hydrodynamic forces (i.e. fluid flow across the surface) and other means of applying specific forces. In addition, the strength of the specific or non-specific binding can be altered by changing the characteristics of the medium, such as conductance and pH.

In a step 730, the number of bacteria in each detection zone, attached to the respective detection surface, is detected via automatic means. In general, the means of counting bacteria will be through automatic visual inspection of images taken of the detection surface using magnified images, or through measurement of spectral intensity or scattered light intensity. Because of the lack of refractive index contrast between bacteria and the surrounding medium, the detection of the bacteria can be enhanced via techniques well-known in the prior art, including the use of phase contrast, differential interference contrast, fluorescence or other means.

It should be noted that the identification of the serotype, strain, species, genus, or other specific typing of the bacteria has been accomplished to the extent that the attachment of the bacteria to the detection surface is specific. However, if the attachment surface is non-specific or broadly specific (e.g. having specificity for a range of bacterial types), the identification can be at this moment incomplete. The use of stains, which can include the use of specific antibodies with optical tags (e.g. fluorescence, scattering, absorption) or tags that permit other forms of detection (e.g. chemiluminescence, radioactive, redox, conductivity or other modes of detection), can be optionally used at this point to determine the type of bacteria attached to the detection surface.

It should also be noted that at this point, not only are the numbers of bacteria determined by the system, but that the specific locations of the bacteria with respect to the detection surface are also known. Because the type of the bacteria are also known (because of attachment to a specific surface or because of the use of a specific stain), each bacterium is now associated with a location and a type. With the tight attachment of bacteria, this information will be relatively constant through the operation of the system. The location noted above can include both the location of an individual bacterium, as well as the location of clusters of bacteria, that can represent roughly spherical clumps as well as linear chains of bacteria.

It should further be noted that in order for the number of bacteria detected by the system to be accurate, it is preferable for at least 50% of the bacteria in the original sample of the step 700 to be attached cumulative to one or more of the detection surfaces, and even more preferable for more than 80% of the bacteria to be attached. The use of the active transport of the bacteria to the detection surface in the step 720 is an important aspect of this accuracy.

For use in disease diagnosis and treatment, it is of great benefit to know not only how many bacteria are present, but also to determine the viability of the bacteria, and also their susceptibility to different antibiotics, singly and in combination. The following steps are optionally employed depending on the desired information generated by the system.

In a step 740, the viability of the bacteria on the detection surface is determined. In general, this is performed in one of two means. In a first means, the detection surface and the bacteria thereon are incubated in the presence of a growth medium, which allows the bacteria to grow and divide. Any bacterium that can be visually determined to engage in growth and division is then indicated as viable. In a second means, vital and mortal stains can be employed to detect bacteria that are viable or non-viable. It should be noted that the total number of bacteria is equal to the sum of the viable and non-viable bacteria, so that the use of any two measures of total bacteria, viable bacteria, and non-viable bacteria will allow the calculation of the third measure.

It should be noted that certain organisms that would be detected in the manner of the present invention may not be viable by themselves, but may be require a host (e.g. for the detection of a virus). In that case, the detection surface can comprise host cells that support the growth of the virus or other organism. In that case, the step 730 of counting the bacteria would be replaced by a step in which the number of infected host cells would be counted. Such step of counting is accomplished according to the characteristics of the virus and the host, and can include the presence of cell surface markers indicative of infection, by changes in the physiology of the host that results from infection, or through lysis or death of the host.

In a step 750, antibiotic in a medium supporting growth can be introduced into the medium of the detection zone, so that the bacteria are then in the presence of the antibiotic during growth. It should be noted that if the organism being detected is not a bacterium, the treatment is matched to that of the organism. Thus, the detection of fungi or yeast would be matched with the use of antifungal agents, and the detection of viruses would be matched with the use of anti-viral agents. The bacteria are kept in the presence of the antibiotic for at different times and concentrations of clinical interest, and the steps 730 and 740 are repeated after an appropriate incubation period or period of effect (i.e. the time for the agent to take effect, which could take place in the absence of the antibiotic). Repetition of the steps 730, 740 and 750 can be performed in order to test the effectiveness of different agents, or different treatment regimens.

The methods and system of the present device will now be described in more detail.

Sample Concentration

Samples can range from a milliliter up to a liter for certain respiratory lavages, and can further range in bacterial concentration from 10 bacteria to greater than $10^6$ bacteria per milliliter. Furthermore, the sample can be present in blood, urine, sputum, lavage fluid or other medium. Sample concentration both concentrates the sample so that bacteria that are present in small numbers can all be effectively introduced into the system, as well as so the background liquid medium can be normalized to have consistent properties upon introduction to the system. It should be noted, however, that certain samples, however, can be used without concentration or other modification within the present invention.

Conventional methods of sample preparation in the prior art can be used for this purpose, including filtration and centrifugation, followed by resuspension of the bacteria in a small fluid. It should also be noted that centrifugation can be accompanied by flocculation, precipitation or addition of a co-precipitate, and such methods are encouraged in that they permit the handling of very small numbers of bacteria, and prevent aggregation of the bacteria. In any of these cases, however, it is preferable that no material be added that will remain a particulate, especially with properties (size or density) similar to that of the bacteria (e.g. the use of polymer beads).

Another method in accord with the present invention is the use of collection with an elutable collector. In such a system, the sample is filtered through a matrix which is densely packed with a material that non-specifically binds bacteria. This material has the further property that the property that binds the bacteria can be reversed through chemical, enzymatic or physical means such that the bacteria can be eluted from the material subsequent to bind. Such a collector can be used both to place the bacteria into a uniform medium that is well suited for further steps in the method, as well as to remove contaminating material that has size or charge differences from the bacteria that are desired to be monitored.

A preferred embodiment of this sample preparation is that of a cartridge with volume of 50-1000 microliters, and preferably less than 250 microliters, in which an ionic exchange resin, is packed. This resin is conveniently supplied in bead form, and can either be permanently charged (e.g. through the use of quaternary amines) or reversibly charged (e.g. through the use of a secondary or tertiary amine). Furthermore, the size of the beads (or pore size of the resin) should be such that in the absence of the charge group, the bacteria would flow easily through the interstices of the bead, and that flow rates through the beads will be reasonable according to the volume of the sample (the beads will preferably be greater than 10 microns in diameter, and less than 2000 microns, and more preferably greater than 20 microns and less than 1000 microns and even more preferably greater than 50 microns and less than 500 microns).

In this preferred embodiment, the sample can be pressed through the cartridge either without modification, or with the addition of a buffer to regulate the pH, and/or also in the presence of a preferably non-ionic detergent, in order to reduce non-specific binding of the bacteria to the system components or to each other. It is preferable for the pH to be relatively neutral (in the range of pH 6 to 8), and in any case sufficient that the bacteria maintain a negative charge, and that the resin maintain a positive charge. This negative charge is typical for most bacteria, but it should be noted that for any organism that is typically positively charged, a cationic resin can be substituted for the anionic resin, and the control of pH will be the opposite of what is described above and below for negatively charged organisms. Due to the opposite polarities of the organism and the resin, bacteria that pass close to the resin will be captured by electrostatic interactions to its surface and stick. This serves to concentrate the large bacteria from a large volume to that of the volume of the cartridge.

In order to release the bacteria from the resin, the pH of the solution can be changed so that the interaction of the resin and the bacteria is reduced. For example, at a high pH (i.e. above the pK of the cations on the anionic resin), the cations on the resin lose their charge, and therefore their relative ability to capture the bacteria. Alternatively, at a low pH, the anions on the bacteria giving rise to their negative charge are protonated, and therefore lose their attraction to the resin.

It is important to find conditions under which the bacteria bind, and others in which the bacteria can be released. In order to mediate the strength of attraction of the bacteria and the resin, other factors that can be modulated include the ionic strength of the solution (i.e. counter ions will tend to reduce the electrostatic attraction), the cation functional group that is used on the anionic exchange resin (e.g. primary, secondary, tertiary or quaternary amine), or the density of the cations on the surface of the resin (i.e. reducing the density will generally reduce the attraction of the bacteria to the resin).

The bacteria can in general be eluted from the resin in a volume not significantly different than that of the cartridge, and with care taken not to mix the eluting solution, even smaller than that of the cartridge. In general, after elution from the cartridge, the solution will be neutralized, preferably with a zwitterionic buffer so that the conductance of the buffer is not increased too much. Other properties of the resulting medium can be adjusted as needed, including ionic strength, conductance, the presence of surfactants, the presence of nutrients or growth factors for the bacteria, and the pH. In general, as will be discussed below, it is preferable for the bacteria to be in relatively low conductance solution. Given that the elution will be performed at pH's either above 3 or below 11, the resulting neutralized solution is likely to have an ionic strength of less than 10 mM salt, which is preferable for the subsequent steps.

It is also convenient as part of or prior to the concentration step to perform a pre-filtering in order to remove larger contaminants, while allowing the passage of the bacteria to be monitored. Such filters can comprise nitrocellulose, nylon, cellulose, or other membranes, bead filters, or other filters as may be convenient. It is also within the spirit of the present invention for the elutable collector above to serve both as an ion exchange resin as well as a size filter. Even in cases where elutable collectors are not used, it is still convenient to use a size filter to remove non-bacterial contaminants. Furthermore, it is also convenient, depending on the source of the sample and the nature of the contaminants, to use a size filter that removes contaminants smaller than the bacteria in the sample; this may not be a problem for the detector, but the smaller contaminants can compete with the bacteria for spots on the surfaces to which the bacteria are meant to attach, reducing the attachment of the bacteria.

Transport to the Detection Zone and Attachment to Detection Surface

The detection zone is conveniently within an enclosed cell, and comprise one or more surfaces on which bacteria will be immobilized and detected. A general format for a detection cell is shown in FIG. 32A, which is a top schematic diagram of a bacterial detection cell 804, and in FIG. 32B, which is a side view schematic diagram of the bacterial detection cell of FIG. 32A through the cross-section X.

The cell 804 comprises two chambers 805, of which there can be as few as one and tens or even hundreds. Each chamber will be used either to handle a different bacterial sample, or to handle side-by-side a single sample, in which the bacteria will be treated with different growth media, antibiotics or other anti-organism agents, antibiotic concentration profiles, temperatures, or other physical, chemical or biological conditions to which the bacteria will be subjected. The chambers 805 are shown as enclosed on all sides, but it is consistent with the present invention for the chamber to be open, such as in a format of a microtiter plate well. If the chamber 805 is closed, an input port 803 and an output port 802 are provided for changing the solution within the chamber 805.

The size of the chamber 805 can vary within the spirit of the present invention, but it is preferable for the width to be 200-5000 microns, and more preferably 500-2000 microns, and most preferably 500-1000 microns, and it is preferable for the height (i.e. the distance between the electrodes) to be 100-2000 microns, and more preferably 200-1000 microns, and most preferably 250-500 microns), and it is preferable for the length to be preferably of 0.5-20 mm (depending, in part, on the number of capture zones, as will be discussed later).

These dimensions are primarily related to the fluid handling (e.g. the larger the volume, the easier it is to handle larger sample volumes), the detector optics (e.g. if it is desired to see individual bacteria, then the magnification must be of a certain amount, which lowers the field of view), the rate at which bacteria can be moved vertically (e.g. depending on the flow of the bacteria through the chamber, the rate of movement must be large enough to allow deposition on the proper surfaces before the bacteria leave the cell), and the dynamic range of the detector (e.g. the number of bacteria can "lie flat" on the surface and be distinct in the detector).

The application of micofluidics devices is well-known in the art, and can be seen, for example, in the services and products of Micronics, Inc. of Redmond, Wash., and CFD Research Corporation of Huntsville, Ala. These devices can handle very small amounts of material, which can be fractions of a nanoliter, and which comprise components which can have multiple functions including sample injection, microdispensing, concentrators, multiplexers, separators, sensors, pressure-driven flow, electroosmosis, electrophoresis, dielectrophoresis, particle transport, electrochemical sensing, electromagnetics for moving paramagnetic particles, and more. These microfluidics technologies are well suited for the present invention.

In the chambers 805, and anode 816 and a cathode 815 are used to create a zone in which placing a potential on the electrodes 816 and 815 will, in the presence of a suitable buffer, cause electrophoresis to occur. While not required, it is preferable for the electrodes 815 and 816 to be parallel, on opposite walls of the chamber, both in terms of ease of manufacturing, as well as causing the electrophoretic fields that will be generated to be perpendicular to the surface of the electrodes and resulting in even movement of bacteria to the respective electrodes. At least one of the electrodes 815 or 816 will be largely transparent, to the extent that bacteria can be detected through the electrode by visual detection means, as will be described below. Transparent conductive surfaces that can serve as the transparent electrode include ITO sputtered films, and printed transparent conductive inks, such as the S-100 and P-100 inks provided by Sumitomo Osaka Cement. The non-transparent electrode can comprise evaporated metallic coatings (gold, silver, aluminum), but the preferred electrode material is platinum or other refractory metals, which can be plated by various forms of chemical or physical vapor deposition.

On the anode 816 are placed capture surfaces 820, on which bacteria will adhere. These capture surfaces will have capture agents with specific affinity for different bacteria, although some of the capture agents will, as will be described later, have general affinity for bacteria or for large groupings of bacteria. For specific affinity, the affinity is generally provided by antibody preparations, which can be polyclonal or monoclonal, with specificity for a small number of bacteria, or can alternatively be provided via aptamers, or other specific affinity molecules. A loading surface 810 is also present, on which bacteria can optionally be concentrated prior to movement to the capture surfaces 820. The loading surface 810 can have a weak or reversible attraction for bacteria, which will dwell on the surface 810 for a period of time, or the loading surface 810 can have very low specific or non-specific attraction for bacteria. Alternatively, the loading surface 810 can have no attraction for bacteria, but will be held close to the loading surface via electrophoretic fields, as will be discussed below. In general, other surfaces of the chamber 805, including those areas of the anode 816 between the loading surface 816 and the capture surfaces 820, or between the different capture surfaces 820, will have very low binding to bacteria, such as that provided by OptiChem coatings (Accelr8 Technology Corporation, Denver, Colo.).

This low binding is generally conferred by a coating applied to the electrodes 815 and/or 816, wherein the coating preferably has components of polyethylene glycol, polyacrylamide or other low surface energy polymer. Preferably, this polymer has been functionalized (e.g. with N-hydroxy-succinimide, thiol, epoxy, hydrazine, or amino groups, or with biotin or avidin) such that agents that bond specifically or non-specifically to bacteria can be attached, so as to confer upon the capture surfaces their attractive characteristics with bacteria.

Bacteria can exhibit high non-specific binding after contact with a relatively non-attractive surface, especially after being in contact with that surface for a period of time. Some of this binding comes with the expression of bacteria attachment proteins, and can include for example various adhesin proteins. In order to reduce the amount of non-specific binding, in those cases where non-specific binding is not desired (e.g. to the loading surface 810, or as bacteria are being moved between specific capture surfaces 820 to which they do not normally bind), it can be convenient to use various agents that can reduce this undesirable non-specific binding, including the use of blocking antibodies that bind to the adhesins, the use of various adhesin-binding agents, such as galabiosides, globotetraoses, and tetrasaccharides, or the use of various detergents (and preferably non-ionic detergents) to reduce this binding. In addition, the binding of the bacteria to surfaces is responsive to both the time of residence, as well as the force with which the bacteria are directed onto the surface. By reducing the electrophoretic force, or by reducing the time over which the bacteria are directed to the electrode by electrophoresis, the force of non-specific binding can be modulated. In addition, it has been found that placing a charge on the electrode that has the same polarity of that of the bacteria can also reduce the non-specific binding.

The attraction of the capture surface 820 for bacteria can be highly specific or relatively non-specific, regarding the type of bacteria. For example, the surface 820 can comprise non-specific polycationic polymers (e.g. polyethyleneimine or polylysine), antibodies specific for serotype, genus, species or class, aptamers, glycoprotein-binding proteins, or others.

While it is shown that there is only the single cathode 815 and the single anode 816, it is also within the spirit of the present invention that there can be multiple electrodes, which can be separately addressable, especially in the case of the anode 816. In such case, individual anodes 816 can be placed roughly at the same locations as the different capture surfaces 820. In the following discussion, where it is indicated that bacteria are being electrophoretically transported to a particular capture surface 820 or loading surface 810, or a force is being directed away from said surface, this can be accomplished either by activating the single electrode 815 and 816 as shown, or alternatively by activating separate electrodes that lie underneath the respective surfaces. FIG. 32C is a side view schematic diagram of the bacterial detection cell of FIG. 32B with the use of addressable electrodes. It should also be noted that the use of these addressable electrodes can be used to create horizontal electrophoretic forces, such that bacteria that are bound to the loading surface 810, for example, under the influence of an addressable electrode 817A and an addressable electrode 819A, can be moved to the first capture surface 820 by placing both electrodes 817A and 819A under a relative negative potential, as well as the electrode 817B, while placing the electrode 819B at a relative positive potential, such that the electrophoretic force field lines transport the bacteria from the loading surface 810 to the first capture surface 820. It should be noted that there are a number of different arrangements of electrodes that would have similar effects, including the use of addressable cathodes 817 and addressable anodes 819 that are offset from one another horizontally, or that there are a multiplicity of addressable cathodes 817 that are activated to differing degrees in order to shape the electrophoretic force fields so as to provide a relatively even distribution of bacteria on the capture surface 820. It can also be beneficial in certain circumstances to have the bacteria distributed in a non-uniform manner on the capture surface 820. For example, in the case where the number of bacteria can range over numbers larger than the nominal range of the system with uniform distribution of bacteria, by having a non-uniform distribution on the capture surface 820, areas of relative paucity of bacteria can be used when the number of bacteria in the sample is high, whereas areas of relative concentration can be used when the number of bacteria in the sample is low.

It should be noted that the vertical distances represented by the electrodes 815 and 816 and by the surfaces 810 and 820 are not drawn to scale. While the separation between the electrodes will generally be hundreds of microns, the vertical dimensions of the electrodes 815 and 816 will generally be measured in tens of nanometers, and the surfaces 810 and 820 will be nanometers to tens of nanometers thick. The size of the surface 810 and 820 can vary greatly within the present invention, but are preferably hundreds of microns up to 5 millimeters in either dimension of the top view diagram. Likewise, the distance separating the surfaces 810 and 820 can vary greatly, but will preferably be between 5 microns or as large as 1 millimeter, and more preferably be between 50 and 200 microns.

Figure 33A:
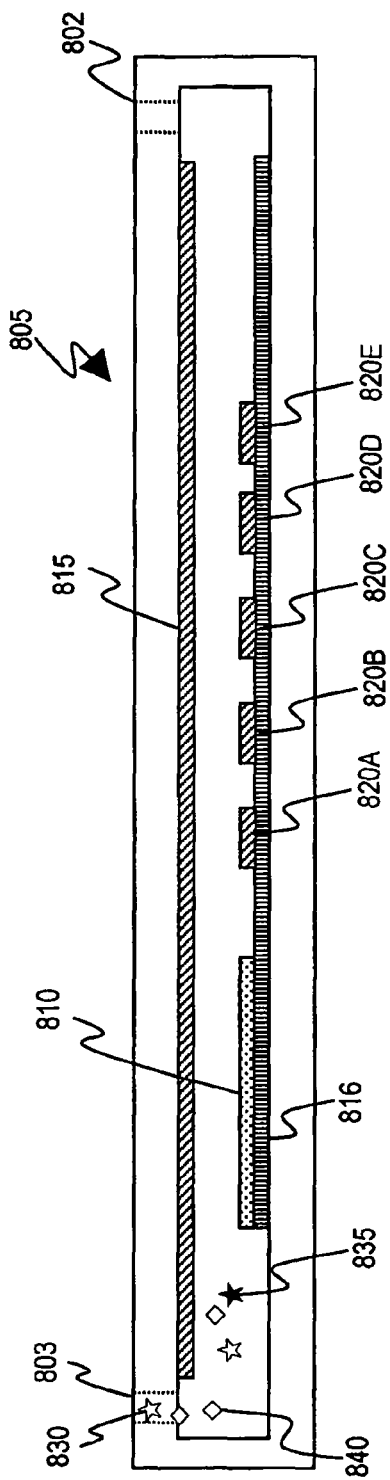
FIGS. 33A-F are side schematic views of the transport and capture of bacteria using the chamber of FIGS. 46A-B.

FIGS. 33A-D are side schematic views of the transport and capture of bacteria using the chamber of $FIGS. 46A-B. In FIG. 33A, bacteria of two types (denoted by stars 830 and 835 and diamonds 840) are introduced into the chamber 805 via the input port 803 (the difference between bacterial symbols that are filled or open will be described below).

A potential is placed across the anode 816 and the cathode 815 such that electrophoresis between the two electrodes is created. This electrophoresis can be accelerated by the use of chemical agents as described above. Optionally, an additional cathode can be placed outside of the port 803 to create an injection field that promotes the movement of bacteria into the chamber 805, as will be discussed in more detail below.

As bacteria 830, 835 and 840 move past the beginning of the anode 816, the move towards the anode on the basis of their generally negative charge. It should be noted that the negative charge of the bacteria can, to some extent, be modified by the pH of the medium in which the electrophoresis takes place. To the extent that some bacteria may have a neutral or slightly positive charge in a medium, it is convenient to raise the pH of the medium so as to confer on the bacteria a more negative charge.

The movement of the bacteria 830, 835, and 840 is at a speed dependent on many factors, including the potential between the electrodes 815 and 816, the conductance of the medium, and the presence of chemical agents to accelerate the electrophoresis, and simultaneously, there is movement of the medium through new medium (with or without bacteria) into the input port 803 and out of the output port 802. As mentioned above, the use of addressable electrodes 815 and/or 816 can be used to promote movement of the bacteria, as well. The balance of vertical movement (e.g. via electrophoresis) and horizontal movement (e.g. via fluid movement, electrophoresis, or other means) should be such that the bacteria will contact the loading surface 810. On the loading surface, the bacteria can either be prevented from horizontal movement either by weak electrostatic forces (e.g. via a weak electrostatic charge on the surface) on the loading surface 810, or will show reduced movement due to lower fluid flow near to the surface in the presence of an electrophoretic force downwards to the loading surface 810. These forces will generally be orthogonal or nearly so, which is convenient since this allows independent adjustment of the movement of the bacteria in both vertical and horizontal directions. In those cases where greater horizontal movement is necessary, for example, a larger vertical force can partially or entirely compensate.

Figure 33B:
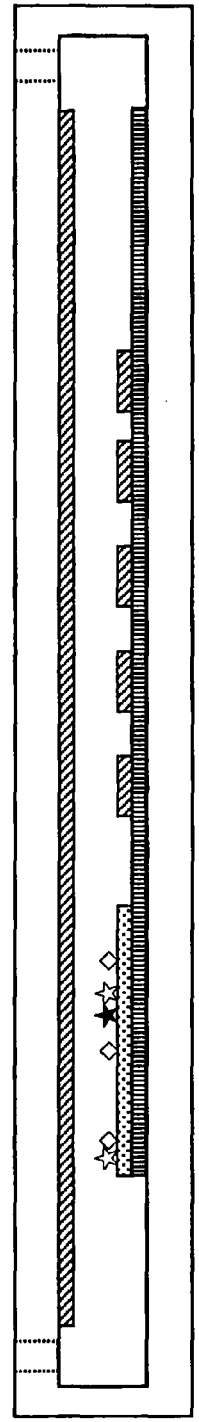

The purpose of the loading surface 810 is to place the bacteria into a very small volume on the capture surface, as shown in FIG. 33B, and to compensate for a dilute sample. Once all of the bacteria are collected onto the surface 810, then their movement onto specific capture surfaces 820 is more easily accomplished.

Figure 33C:
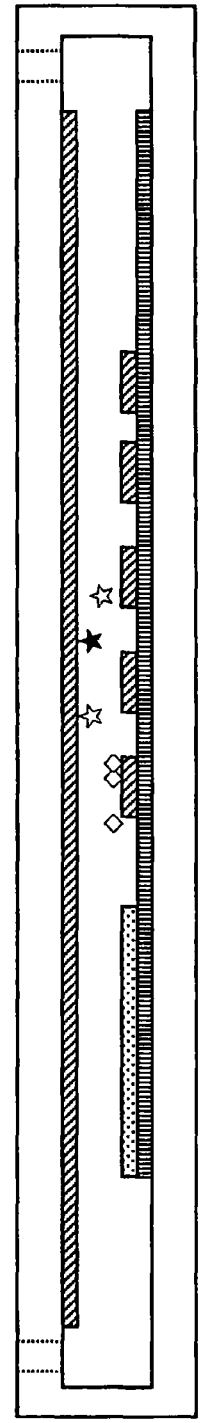

In FIG. 33C, the bacteria are moved from the loading surface onto a specific capture surface 820. If the loading surface 810 has an electrostatic attraction for the bacteria, the electrostatic force is reversed, as will be discussed in more detail below. If the bacteria are held close to the loading surface 810 solely by virtue of the electrophoretic field, this field is either turned off, reduced, or even reversed.

The bacteria are then moved horizontally along the chamber 805 through movement of the fluid, which movement may be accomplished via electroosmosis, positive displacement pumps, peristaltic pumps, or other means. This movement is coordinated with the further application of vertical electrophoresis, which coordination can be simultaneous or sequential. That is, in sequential coordination, fluid movement can be performed for a certain period, and then followed by a period of fluid non-movement during which electrophoresis is applied, or the electrophoresis can be applied during movement in simultaneous coordination. In the latter case, the speed of movement or the magnitude of the electrophoretic force can be varied, such that bacteria do not move more than the width of a capture surface 820 before contacting the surface 820. Indeed, it is preferable that all of the bacteria do not contact the capture surface 820 at its leading edge (i.e. to the left in the figure), so that there is a more even distribution of bacteria on the capture surface 820.

Instead of the bacteria 840 moving horizontally across the chamber 805, the bacteria can alternatively be moved in a "zig-zag" fashion if addressable electrodes corresponding to the various surfaces 810 and 820A-E are used. That is, the bacteria 840 can be moved from the loading surface 810 to the electrode 815 by the proper potential being placed on the addressable electrode beneath the loading surface 810, and afterwards, the bacteria 840 can be moved to the first capture surface 820A by placing a positive potential on the electrode beneath the surface 820A and a negative potential on the electrode 815. Then, the bacteria 840 can be successively moved from the capture surfaces 820A-E to the electrode 815 and thence to the next capture surface 820B-E. This has the advantage that bacteria 840 do not accumulate on the trailing edges of the various capture surfaces 820 (i.e. stick to the first part of the surface that they encounter), but rather are more evenly distributed on the capture surfaces 820. This effect can be further strengthened by using addressable electrodes replacing the single electrode 815, wherein these addressable electrodes can either be directly on top of the corresponding addressable electrodes beneath the capture surfaces 820, or alternatively can be staggered with respect to the capture surfaces 820 in the horizontal direction.

Figures 33D, 33E, 33F:
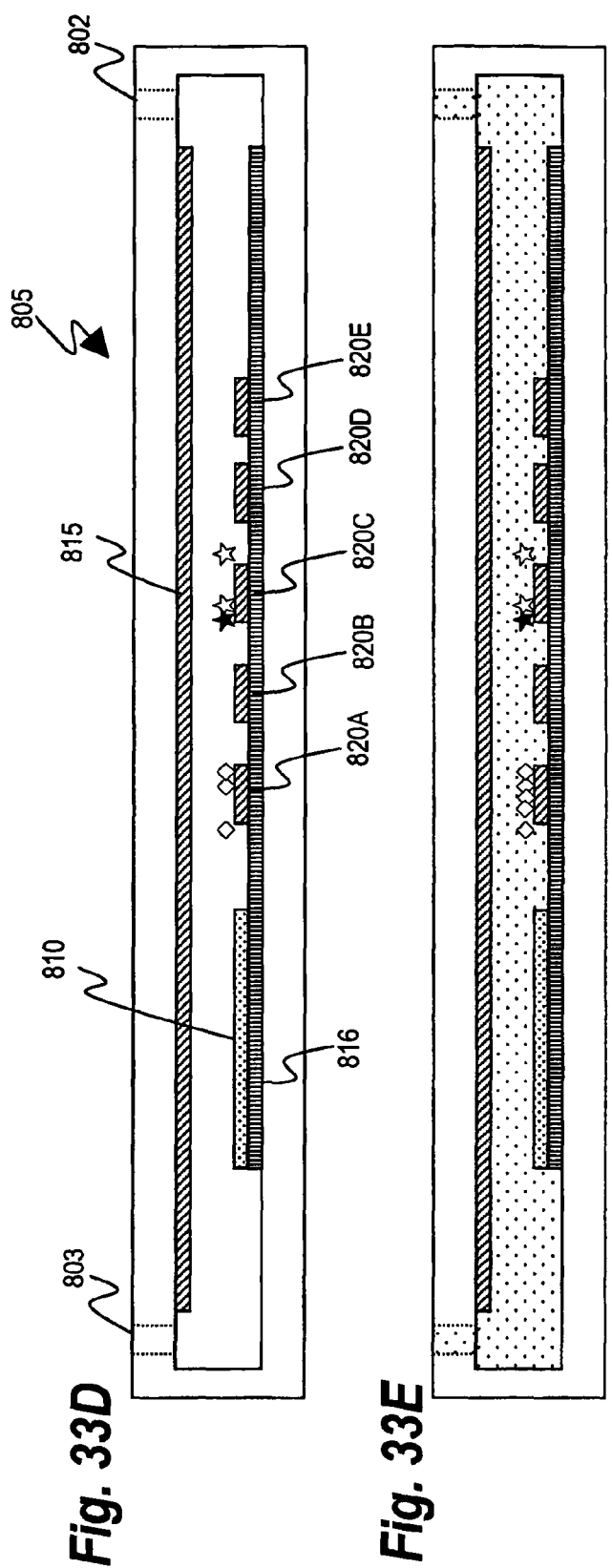

As can be seen in FIG. 33C, on the leftmost capture surface 820A, only the bacteria 840 are bound, whereas the bacteria 830 and 835 do not bind at this surface. In FIG. 33D, as the process is repeated and the bacterial sample is brought into contact with additional capture surfaces 820, the bacteria 830 and 835 are now attached to the capture surface 820C.

An alternative embodiment is shown in FIGS. 34A-D, which are side-view schematic diagrams of electrophoretic transport to the detection surfaces. In FIG. 34A, a bacterial sample in low-electrolyte medium 882 is brought into contact with a high-electrolyte medium 880 with an interface 890 formed between them at roughly the location where a sample input port 895 insects the chamber, which has an alternative input port 896. This interface can be formed by movement of the low-electrolyte sample through the sample input port 895 until it intersects roughly the chamber, and then by movement of the high-electrolyte medium through the alternative input port while preventing back-pressure from moving the low-electrolyte medium 882 back into the sample input port 895. It should be noted that while the interface 890 is shown as sharp and perpendicular to the sample input port, the specific orientation and position of the interface 890 can be varied within the present invention. Also, the differences in the rate of movement of bacteria between the high-electrolyte medium and the low electrolyte medium is related to the ratio of the conductivities in the two media. It is preferable for the difference in conductivities to be greater than 10-fold, and even more preferable for the difference to be greater than 50-fold, and even more preferable for the differences to be greater than 200-fold.

A cathode 910 is placed in the sample well within in the sample input port 895, distal relative to the chamber from much or all of the bacteria 830 and 840. An anode 900 is placed after the last capture surface 820. The placement of the anode 900 and the cathode 910 can be varied within the operation of the present invention, but it should be such that the bacteria 830 and 840 and capture surfaces 820 should be between the anode 900 and cathode 910. Indeed, both the anode 900 and cathode 910 can be outside of the chamber.

In the first step of operation, shown in FIG. 34B, a potential is applied between the anode 900 and cathode 910. Because the resistance in the high-electrolyte medium 880 is very low, the potential drop is primarily through the low-electrolyte medium 882. Hence, the bacteria 830 and 840 will move quickly through the low-electrolyte medium, until they reach the interface 890, at which point their movement is significantly slowed. Indeed, by the use of a large difference in the conductance of the two electrolytes 880 and 882, it is possible for the movement in the two electrolytes to differ in movement by many orders of magnitude. Thus, the bacteria 830 and 840 will tend to concentrate at the interface 890 as shown in FIG. 34B.

In FIG. 34C, the bacteria 830 and 840 are moved in a reverse direction (back towards the electrode 910) by reversing the potential, so as to move the bacteria away from the interface. The distance that the bacteria can be moved can be quite short (e.g. hundreds of microns) or far (e.g. centimeters) within the present invention. At this point, the high-electrolyte medium is removed by pushing low-electrolyte medium in through the alternative port 896, such that the entire system is now low-electrolyte medium, and the system is in a similar position to that shown in FIG. 33A, with the bacteria to be introduced into the system.

Another embodiment of the present invention is shown in FIGS. 35A-D, which are side-view schematic diagrams of a chamber in which contaminating material is distinguished on the basis of its behavior under electrophoretic fields. In this case, four types of material are shown, including bacteria 830 and 840, as well as a first contaminant 837 and a second contaminant 839. In FIG. 35A, all four materials are transported to the loading surface 810, resulting in a situation similar to that of FIG. 33B. In this case, the loading surface 810 is set such that it has an attraction for the materials 830, 840, 837 and 839, and that all of the materials bind to the surface 810.

In FIG. 35B, the polarity of the electrodes 815 and 816, such that the material is directed towards the electrode 815. The material 837 has either a generally lower attraction to the loading surface 810, or experiences a larger electrostatic force relative to the other materials, such that it is removed from the surface 810 while the other materials remain attached. In FIG. 33C, the potential on the electrodes 815 and 816 is increased such that the bacteria 830 and 840 are removed from the loading surface 810, but the material 839, having a higher attraction for the surface 810, remains bound to the surface 810. The bacteria 830 and 840 are now able to be transported through the chamber 805, and to attach to the capture surfaces 820.

It should be noted that the binding force required to remove bacteria from a surface can be varied by careful selection of materials comprising the loading surface 810 or the capture surface 820. For example, for non-specific binding, the concentration of the non-specific binding agent (e.g. polyethyleneimine or other polycation) can be varied, the length of the polymer chain can be varied, the type of ionic charge can vary (e,g. primary, secondary, tertiary or quaternary amine, or the groups substituent to the nitrogen), the linear or volumetric density of the ionic charge in the polymer, or other changes. In addition, in the case of specific binding, if the binding agent (e.g. an antibody) does not provide in itself sufficient binding force to hold the bacteria in place during the operation of the system, the specific binding agent can be supplemented by a more tightly binding non-specific agent, so that the total binding force is a combination of non-specific and specific forces. It is also within the spirit of the present invention for there to be a sequence of capture surfaces 820 that are distinguished not on the basis of different specific binding (e.g. by antibodies or aptamers), but rather by the different levels of non-specific binding, to which different bacteria bind with overall different affinities. Thus, in general, the first capture surface encountered by the bacteria would have overall lower non-specific binding, and subsequently encountered surfaces 820 would then have increasing levels of non-specific binding.

Organism Detection

Detection of the organisms can take place in a variety of different means, though it is generally performed by visual detection means. In this case, a magnified image of the detection surfaces 820 are obtained, with or without the addition of stains, and this image is preferably analyzed by automated electronic means. For more general discussions of detection in the present invention, see also above.

The detection can include the use of methods of microscopy, including brightfield, darkfield, fluorescence, chemiluminesence, phase, differential interference contrast and other methods, as well as methods of measuring overall light intensity and spectral response without imaging. Such methods can be further enhanced using illumination from directed laser or incoherent light illumination without the use of conventional condenser illumination, such as can be used for scattered light or fluorescent light response. In addition, reflected light, transmitted light, or evanescent light illumination can be employed. While the methods of microscopy can be employed in the present invention, it is advantageous for the system to use optical systems that do not require careful and repeated calibration. Therefore, it is preferred that optics employing a large depth of field are employed, and which are relatively low magnification. In addition, it is within the teachings of the present invention for multiple methods to be utilized on the same sample, including, for example, the use of brightfield phase imaging and fluorescence reflected imaging to be performed sequentially, in order to obtain different information about the same imaging field of view.

The system frequently will involve the horizontal movement of either the chamber in which the bacteria are captured, or the detector, given that the measurements will be made over a significant period of time, and generally involving hours for those measurements involving bacterial growth (see below). In those cases, it is convenient for the system to be able to reestablish its original relationship of bacteria relative to the detector, so that images obtained over a period of time can be compared. While this can be sometimes performed with an "open loop" control system, in general, a "closed loop" system involving feedback is preferred. Two preferred methods for this feedback involve the use of visual fiducials on the chamber, which fiducials are easily detected by the visual system, with such information being used to adjust the horizontal movement of the system until the original relationship of the chamber to the bacteria is established. A second method of convenience is to make a rough "open loop" mechanical estimate of the original location, to obtain an image, and then at that time use image analysis to register the bacteria and other visual aspects of the chamber (potentially also involving visual fiducials). Such forms of registration can involve the use of Fourier transform or other correlation methods (such as matrix shifting) to match the images.

In general, the system will detect the presence and characteristics of organisms through an automated program, such as the LabView software with the IMAQ vision software from National Instruments (Austin, Tex.), ImagePro scripts, or high-speed image analysis using custom computer software. The system will store not only the presence of a bacterium, but also the location of the bacterium. Given that the bacterium is fixed at a location on a capture surface 820, it is considered that over a period of time, including growth of the organism, the bacterium will not move significantly. Additionally, if a bacterium is noted in a location at which a bacterium was not previously located, it is assumed either that this bacterium was dislodged from another location, or that this bacterium was newly grown from another bacterium. Furthermore, changes in the size, the staining with moral or vital stains, or other factors can be correlated then to the change in status of the organism that was previously seen in that same location.

In general, there will be at least one non-specific capture surface 820, in order to capture all organisms that the specific capture surfaces 820 do not capture. As mentioned before, this surface is preferably a poly-cationic surface, given that most bacteria have an overall negative electrostatic charge, or can be made to have such a charge at an appropriate pH. However, surfaces that have polyanionic charge, hydrophobic characteristics, single or multiple antibodies against bacteria, glycoprotein binding agents, as well as polycationic and other active components, singly or in combination, can also be used. It is also possible within the present invention for there to be only a single capture surface 820, and it is preferred in that case that the surface have non-specific binding characteristics.

In the case of a non-specific capture surface, it is still desirable to be able to identify one or a number of different organisms. This identification will generally be performed by indicators that are specific for a serotype, genus, species, class, or other subset of bacteria or other organism that is being detected, and is conveniently an antibody, aptamer, or other molecule. The use of such indicators in the present invention is demonstrated in FIGS. 36A-E, which are side-view schematic diagrams of detection of multiple bacteria on a non-specific surface. Note that the anode and cathode are not indicated in this figure.

In FIG. 36A, bacteria 530 and 540 are bound to a non-specific surface 825 in the chamber 805. An indicator 842 that is specific for the bacteria 840 is introduced into the chamber in the FIG. 36B through fluid flow through input port 802 to output port 803. This indicator 842 binds to the bacteria 840, and then the unbound indicator 842 is removed from the chamber as in the FIG. 36C. It should be noted that the bonding of the indicator 842 to the bacteria 840 can be accelerated through use of the anode and cathode (not shown) that can be used to accelerate the binding of the bacteria 830 and 840 to the surface 825. At this point, the presence of the indicator 842 is determined through the detection methods as described above, and the specific locations are recorded in the system (e.g. in a list, database, or other format that can either be stored in computer memory and/or on some physical storage medium such as a hard disk drive). In FIG. 36D, a second indicator 832 that is specific for the bacteria 830 is introduced into the cell 805 and allowed to bind to the bacteria 830, and is then removed by fluid flow through the ports 802 and 803, leaving the system in the state of FIG. 36E.

It should be noted that the means of detection means used to detect the indicator 832 and the indicator 843 can be the same. For example, if the indicators 832 and 842 are detected using fluorescence, the same fluorescent dye can be used in both detections. That is, at the state of FIG. 36E, the system can detect the presence of both the indicators 842 and 832 together. Because it has previously established the location of the bacteria 830 by determining the locations of the indicator 832 as in the FIG. 36C, then the locations of the bacteria 840 will be in those new locations at which the indicators 832 and 842 are detected. Indeed, this method can be extended serially to allow the detection of a large number of specific bacteria using specific indicators, even though the bacteria are immobilized on a non-specific surface 825.

In those cases where the means of detection are different (e.g. where the indicator 832 is detected by the fluorescence of one fluorophore, whereas the indicator 842 is detected by the fluorescence of another fluorophore, separable by excitation and/or emission wavelengths), then the indicators 832 and 842 can be introduced into the chamber 805 simultaneously, washed out of the chamber simultaneously, and then detected serially or concurrently.

It should be noted that in addition to the use of agents that distinguish specific bacteria (e.g. through the use of fluorescent-labeled antibodies), there are many other characteristics intrinsic to the bacteria or organisms that can distinguish them. Such other characteristics include the morphology of individual bacteria (e.g. spherical versus rod versus helical), colony morphology (e.g. a clumped vs. chained), absorption or scattering of different light frequencies, their resistance or susceptibility to different classes of drugs (e.g. see below), their ability to grow in a particular growth medium, their rate of growth, their size, and more. These agents can be used to distinguish multiple types of bacteria bound to a non-specific capture surface 820. Given also that there are frequently contaminants in the sample that will give rise to signals with, for example, light scattering or optical absorption means of detection, these methods can also be used to distinguish bacteria from non-bacterial contaminants.

While the system can operate through the identification and monitoring of specific bacteria, it is also within the spirit of the present invention for the detector to sum the total response of all of the bacteria on the capture surface 820 (e.g. the scattered light). This can also be used to indicate the total number of bacteria, and growth in the number of bacteria will be evidenced by an increase in the total response.

Detection of Organism Viability

Organism viability can be determined by a variety of methods, and can include both methods that highlight viable organisms (vital stains) as well as dead organisms (mortal stains). These stains can comprise ethidium or propidium dyes, hexidium iodide, SYTO nucleic acid stains, 7-aminiactinomycin D, SYTOX Green/Orange/Blue nucleic acid stains, and others. A good introduction to these and other stains are available from the Molecular Probes Handbook, at www.probes.com.

It can be useful to detect the presence of new organisms or the increase in size of existing organisms. A method for accomplishing this is shown in FIGS. 37A-D, which are schematic diagrams of detecting growth in an organism.

Figure 37A:
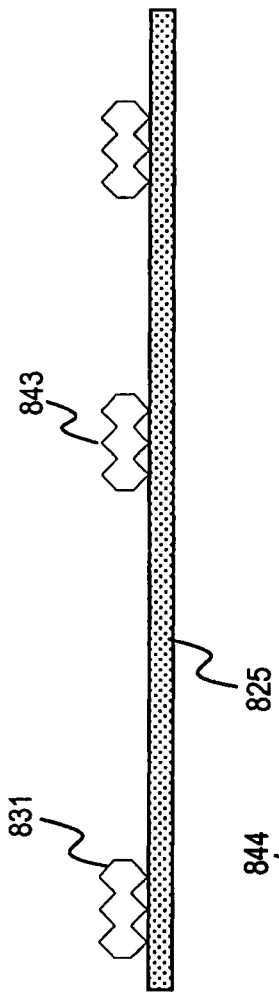
FIGS. 37A-D are schematic diagrams of detecting growth in an organism.
Figure 37B:
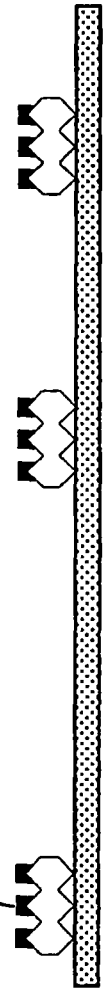

In the FIG. 37A, bacteria 831 are attached to a non-specific surface 825. The bacteria 831 have a number of sites 843 for the binding of a molecule 844. These sites 843 could represent regions of high negative electrostatic charge, glycoproteins, epitopes for broad or narrow range antibiotics, etc. In the FIG. 37B, the sites 843 are bound by the molecule 844 in a great excess of the molecule 844, so that all of the sites 843 are occupied by the molecule 844, after which the excess molecule 844 is washed away.

Figure 37C:
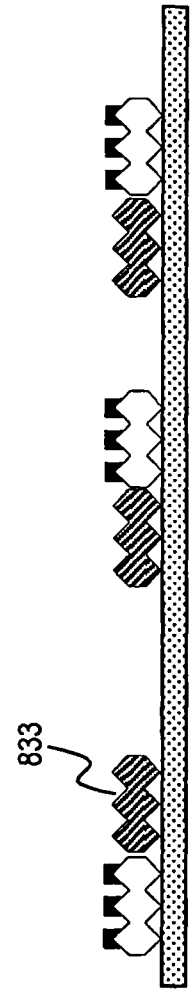

In the FIG. 37C, the bacteria 831 experience growth, either in size, or as indicated in the figure, in the number of bacteria 831, creating new bacteria 833. It should be appreciated that new bacteria will often be bound to the surface 831 close to the location of the original bacteria 831, and that the proximity can be improved by the use of an electrophoretic force during growth that drives the bacteria 831 and 833 towards the surface 825. This proximity is not necessary to detect new bacterial growth 833, but rather to associate the new bacteria 833 with the bacteria 831 from which they were derived, in order to demonstrate the viability and growth of the bacteria 831.

The new bacteria 833 will have binding sites 843 to which molecule 844 is not bound. In the diagram, all of the sites 843 which are not bound by the molecule 844 are located on the new bacteria 833, while depending on the manner of bacterial growth, it is also possible that those binding sites 843 will be distributed on both daughter bacteria arising from the fission of the original bacterium 831. It should also be noted that even in the absence of separation between new bacteria—for example, that the surface area of the bacteria 831 has increased, without the creation of new bacteria 833—the increase in surface area will generally involve the creation of new sites 843.

Figure 37D:
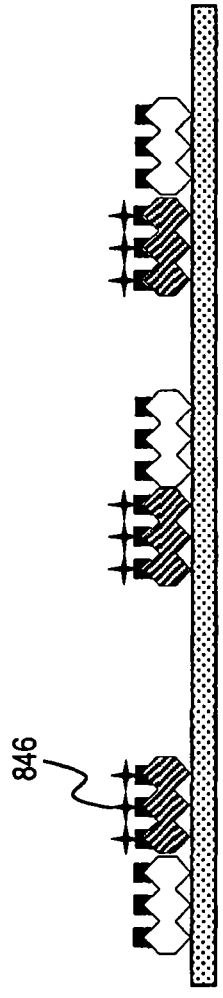

In the FIG. 37D, the bacteria 831 and 833 are now incubated with the molecule 844 which is optionally modified so that it can be detected with an indicator 846 that can be detected by the system, and then the molecule 844 with indicator 846 that is not bound to the bacteria 831 and 833 are washed away. Thus, any indicator 846 will be indicative of new bacterial growth or change in the number of sites on the bacteria to which the indicator 846 can bind.

Organism Growth

The bacteria can now be grown in order to determine their viability, growth characteristics, and susceptibility to various agents (such as antibiotics). The growth occurs by the incubation of the bacteria in the presence of a suitable medium at proper temperatures and oxygen saturation or depletion (e.g. for anaerobic or aerobic bacteria, depending generally on the source of the sample). The incubation medium will be in general matched to the bacteria being monitored—for example, lung aspirates, urine samples and blood samples would all be incubated with media that are well suited for bacteria or other organisms of the respective origins, as is well known in the art. In addition, the anti-growth agents to be tested for effects are also well-known in the art, and will change with the discovery of new agents and as the mix of current agents in use changes with the advent of resistance.

During the growth of the bacteria, it can be convenient to apply a continuous or frequent electrophoretic force, in order that daughter or new bacteria 833 are in roughly the same location as the original bacteria 831 from which they are derived, allowing the provenance of the bacteria 833 to be determined. This will then allow the determination of which of the original bacteria 831 are growing, and it secondarily allows the determination of the type of bacteria to the new bacteria 833 without having to do additional tests (e.g. antibody staining).

It should be noted that the electrophoretic force experienced by the bacteria is inversely related to the conductance of the medium, and therefore it is convenient to have a low conductance growth medium. Most media used for the growth of bacteria, yeast, and other organisms, however, generally has $Na^+$, $K^+$, $Mg^{+2}$, $Cl^-$, $SO_4^{-2}$, $NO_3^-$ and other ions as both nutrients as well as to maintain an ionic strength of the medium. It is preferable for the growth medium to have a conductivity of less than 5 mS/cm, and more preferable for the growth medium to have a conductivity of less than 2 mS/cm, and even more preferable for the growth medium to have a conductivity of less that 1 mS/cm. It should be noted that these conductivities are generally higher than that used in movement of bacteria and other molecules for concentration of these at the electrode, as described above. However, because the bacteria 833 are created at or proximal to the electrodes, the movement required is small in distance, and lower amounts of electrophoretic force are required. In addition, the application of the electrophoretic force need not be constant, and can be applied intermittently, especially in those cases where the growth medium is not under constant bulk movement. Because of the slow diffusion of microorganisms, it is preferable to apply electrophoretic force when the medium is not in bulk movement no more frequently than every 10 seconds, and even more preferable no more frequently than every 60 seconds. In general, many growth media contain large amounts of salt (e.g. 0.5% NaCl in L Broth), and it is preferred that this salt be replaced by a zwitterionic species, such as alanine or cysteine, that contributes very little conductance. It is also preferable for the osmotic strength of the medium be high enough so that the bacteria do not undergo osmotic shock. Non-ionic osmotic components, such as glycerol or sucrose, can be used for this purpose.

Growth by itself indicates primarily the viability of the organism, and potentially the relative rates of growth of the bacteria. However, it can also be used to study the susceptibility of the organism to various anti-organism agents such as bactericidal and bacteriostatic agents. Examples of such agents include individual agents or combinations of agents selected from antibiotic families such as cephalosporins, penicillins, carbapenems, monobactams, other novel beta-lactam antibiotics, beta-lactamase inhibitors, fluoroquinolones, macrolides, ketolides, glycopeptides, aminoglycosides, fluoroquinolones, rifampin, and other families, including novel agents, used as antibiotics in clinical practice or in research. In the simplest case, this would involve the incubation of the organism in a constant concentration of anti-organism agent (AOA), and determining the rate of growth and/or the rate of death of the organism.

FIG. 33E shows how this would be performed with the present invention. In FIG. 33D, the bacteria 830, 835 and 840 have been specifically bound to capture surfaces 820. After a period of incubation in one concentration of an AOA in a growth medium (indicated by light stippling), the bacteria 840 have increased in number, and the bacteria 830 and 835 have not, indicating that the bacteria 840 are not susceptible to AOA at the concentration used, and that the bacteria 830 and 835 are susceptible at the concentrations of the AOA used. It should be noted that bacteria 835 are of the same type as bacteria 830, except that they are dead. Given a mortal or vital stain, therefore, it can be determined that bacteria 830 have not been killed by the concentration of AOA, indicating either that AOA prevents growth but does not kill the bacteria 830, or that at the concentrations used, AOA only acts to stop growth.

In FIG. 33F, the concentration of the AOA is increased, and the number of bacteria 840 still increases, indicating that the bacteria 840 are non susceptible to the bacteria even at this concentration. However, now the bacteria 830 have been killed (indicated by the dead bacteria 835), indicating that at this concentration, AOA is lethal. Thus, as indicated in FIGS. 33E-F, by using increasing concentrations of the AOA in the growth medium, the concentration response of the bacteria to the AOA can be determined. Clearly, by increasing the amount of AOA in steps over a period of time, the minimum inhibitory concentration (MIC) can be determined. In addition, because viability of the bacteria can also be determined at each concentration, the minimum bactericidal concentration (MBC) can also be determined.

It should be noted that the detection of growth and viability at different concentrations of AOA can be performed either by using a series of chambers 805 in the cell 804, each of which challenges the bacteria with a specific concentration of AOA, or alternatively, by increasing the concentration within a given chamber 805. In the former case, the time response of the bacteria can be easily established, as well as the persistent response of the bacteria once the AOA has been removed (e.g. a post-antibiotic effect). That is, the bacteria can also be challenged with a given concentration of AOA for a brief period, and then the medium replaced with a medium lacking the AOA, and the lack or growth or the death of the bacteria can be monitored over time.

Figure 38A:
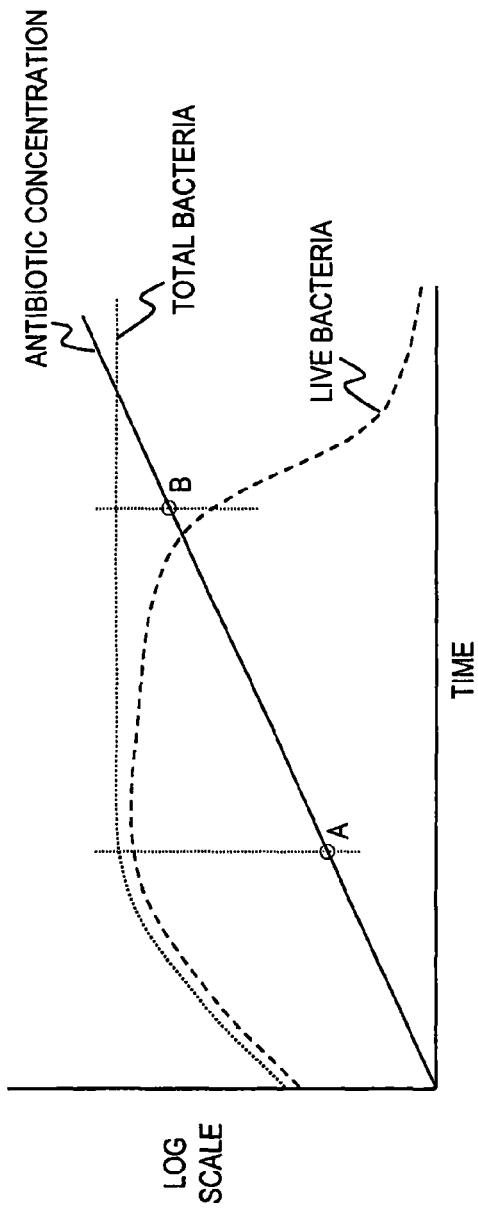
FIGS. 38A-B are graphs of the response of bacteria to a changing concentrations of an anti-organism agent.
Figure 38B:
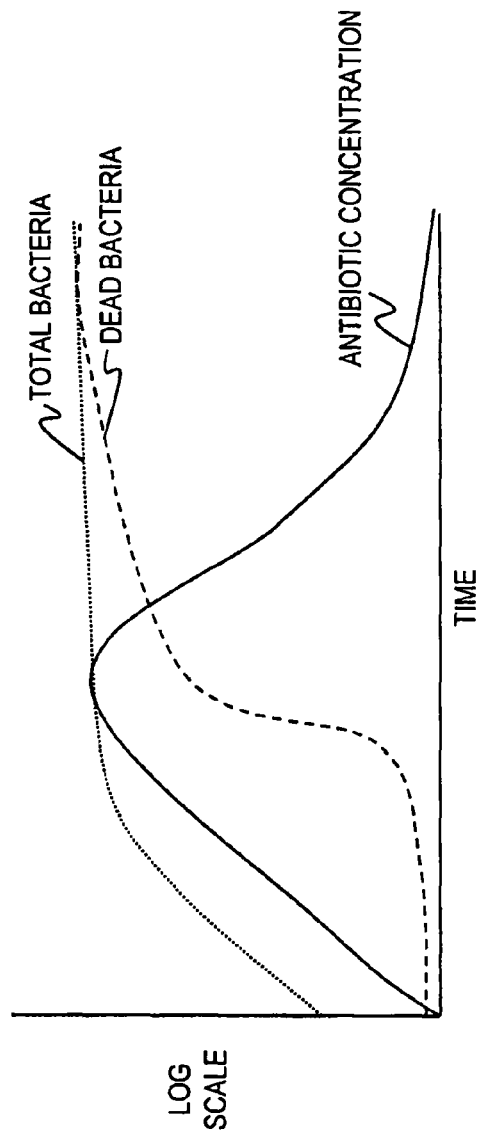

At described above, so as not to use separate chambers 805 for every different concentration of AOA, the concentration of AOA within a chamber 805 can be increased over time. FIGS. 38A-B are graphs of the response of bacteria to a changing concentrations of AOA. In FIG. 38A, the concentration of AOA is increased over time, generally according to an exponential increase with time, although it is also convenient for the concentration to increase linearly or according to other concentration/time relationships, including step functions increasing the concentration; these step functions can be placed at regular concentration intervals, or alternatively at standard concentrations as indicated or suggested by clinical laboratory standards as might be set by organizations such as the National Committee for Clinical Laboratory Standards. The system is then used to determine the total number of bacteria, the number of dead bacteria, and the number of live bacteria (as described above, any two of these numbers gives rise to the third number).

At the point that the total number of bacteria does not continue growing, indicated in the figure at the concentration A, is considered to be the MIC. The point where the number of live bacteria begins to decline (at the concentration B) is considered to be the MBC. It should be noted that the actual MIC and MBC can be lower than the concentrations A and B respectively, and will only be the MIC and MBC in those cases where the rate of increase in concentration is very slow relative to the growth of the bacteria. Thus, given that it is desired that the MIC and MBC of AOA be determined within a factor of X, it is preferable for the concentration of AOA to increase by a factor of X no faster than half the doubling time of the bacteria under the conditions of the incubation lacking AOA, and it is more preferable for the concentration of AOA to increase by a factor of X no faster than the doubling time of the bacteria, and it is most preferable for the concentration of AOA to increase by a factor of X no faster than twice the doubling time of the bacteria.

The less growth of bacteria required in order for there to be high confidence that growth has occurred will reduce the time needed to perform a test. By monitoring individual bacteria, growth can be seen with the doubling of only a small number of bacteria. That is, if looked at in bulk as in conventional turbidity assays, for example, the limit of sensitivity of detecting bacterial growth is limited by the signal to noise ratio in the turbidity measurement. However, the fission of a bacterium is a discrete event that can be detected, even if that bacterium is one of many thousands of bacteria. Thus, the present invention can have a very high sensitivity, with the system preferably able to detect doubling of less than 25% of the bacteria, more preferably able to detect doubling of 10% of the bacteria, and most preferably able to detect doubling of 5% of bacteria. Note that the doubling time for a fraction of the bacteria can be either predetermined (e.g. by calibration in a laboratory with experimental specimens), or more preferably, by comparing the bacteria in the absence of the AOA with those in the presence of the AOA—this makes the results internally controlled.

The measurement cut-off points for determining antibiotic susceptibility can be, as discussed above, be expressed in absolute terms, such as the doubling of a given percentage of the bacteria. However, the number of bacteria required to make a statistically valid judgment can be dependent on the number of bacteria present in the sample. For example, if there are only 10 bacteria present in each chamber, evidencing a single bacterium doubling represents 10% of the sample. Alternatively, with very large numbers of bacteria on the surface (e.g. more than 100,000), the doubling of even 1,000 bacteria (i.e. 1%) is probably statistically significant. Thus, it is in many cases preferable to analyze the number of bacteria required to show doubling in the control condition (i.e. growth medium absent the AOA) relative to the number of bacteria showing doubling in the experimental condition (i.e. growth medium with the AOA) as to be statistically relevant. For example, a conventional method would be to apply a chi-squared test to these two numbers, and to decide whether the results met a particular probability of significance. In general, it is preferable for this probability to be less than 0.05, and even more preferable for this probability to be less than 0.025 and most preferable for this probability to be less than 0.01. Because small numbers of bacteria will not permit very small chi-squared probabilities, the standards for probability can be conveniently reduced for cases of very small numbers of bacteria (e.g. less than 20 viable bacteria in the growth medium control).

It should be understood that the doubling time of bacteria is a population phenomenon, and that within a population of bacteria, some bacteria will divide more quickly that others. This could be due both to slight genetic differences in a population, or purely statistical effects. However, it can also be due to the stage at which each bacterium is growing during its preparation, as the bacteria will exhibit substantially different lag times in their growth when placed in new medium depending on that stage. While a longer period of time is generally going to provide more information about the growth characteristics and AOA susceptibility of the bacteria, there is a need to supply to medical personnel information about the bacteria and their susceptibility to AOAs. Given that lag times for most of the bacteria of interest on the order of 2-6 hours, and the doubling time of the bacteria are generally 1-2 hours, it is preferable for measurements of bacterial growth and susceptibility to AOA use detection of the bacteria at no more than 8 hours, and more preferably less than 6 hours. Even if not all bacteria in a sample have an opportunity to demonstrate doubling, a large enough fraction of those bacteria will have so as to be able to indicate susceptibility and growth.

In this case, it is useful to have all information available for individual bacteria relating to vital and/or mortal staining (indicating live versus dead bacteria), as well as growth in the presence of growth medium with and without the presence of AOA. Any observation in which the fraction of live bacteria decreases by a first predetermined fraction in the presence of AOAs, or in which the growth of bacteria (evidenced either by doublings or by increases in the size of the bacteria) is decreased by a second predetermined fraction in the presence of AOA, are evidence of the action of the AOA. In general, the first determined fraction, because of its evidence of higher death, will generally be smaller than the second predetermined fraction. A preferable value of the first predetermined fraction is 20%, and a more preferable value is 33% and the most preferable value is 50%. A preferable value for the second predetermined fraction is 50%, and a more preferred value is 66%, and a most preferred value is 80%.

As indicated above, most studies on AOA susceptibility relate to the concentration at which a particular effect is encountered, rather than the specific kinetics and effects that are observed. That is, in conventional tests, the bacteria are usually challenged with a number of different concentrations (or even changing concentrations) of AOAs to determine the concentration at which the bacteria exhibit death or lowered rates of growth, from which the MIC or MBC can be determined. Consider, for example, a conventional antibiotic test employing an agar plate with an antibiotic disk. Around the disk are colonies of various sizes, representing not simply death, but slower growth in the presence of differing concentrations of antibiotic. By this measure, the MIC is not easy to define, since incubating the plates for an extended period of time would allow colonies to appear at concentrations that are considered inhibitory.

However, both from a standpoint of time and cost, it can be convenient in some cases to instead challenge the bacteria with single, constant doses of the AOA, and then to observe the specific effect and rate of effect of the drug, in order to determine susceptibility. In the present invention, a constant dose of AOA can be provided, and the rate at which bacteria are killed, or the degree to which their growth is reduced, can be used to gauge the likely effects at a multiplicity of therapeutic doses. These responses can be described with new measures of AOA effect, such as the bacterial doubling time in the presence of an AOA divided by the bacterial doubling time in the absence of the AOA. In this case, for bacteria that are resistant to an AOA but whose doubling time is tripled in the presence of the AOA, treatment with the AOA can still be meaningful. These values can be provided either at a single dose, or at multiple doses. To the extent that bacteria of differing levels of susceptibility can be isolated and studied, the information at one or more concentrations of the AOA can be useful in then predicting the response at other concentrations.

It should be noted that the concentration of AOA in a human or animal is determined by the amount and frequency of treatment (e.g. injection), as well as the AOA pharmacokinetics. In many cases, the pharmacokinetics are well-known for disease-free humans, and can be modeled on the basis of the known medical state (e.g. liver failure) of the person being monitored. Using this information, the concentration of AOA over time in the target organ (e.g. blood, urinary tract, lungs) can be estimated. This AOA concentration can be approximated in the chamber by mixing medium with AOA in relative parts with medium lacking AOA, to produce the estimated profile of AOA such as that shown in FIG. 38B. In general, the concentration of AOA will rise, peak, and then exponentially decay. As before, the total number of bacteria, the dead bacteria and the live bacteria can be monitored over time. In this case, the pharmacodynamic parameters MIC and MBC are not well defined, since one is looking at the response to the bacteria including the pharmacokinetics of AOA, and one looks therefore at the minimum inhibitory dose and the minimum bactericidal dose by running replicates of the system at different doses, and then monitor if the overall AOA concentration profile results in the cessation of growth or the death of the bacteria. It should be noted that while the analysis of FIG. 38B deals with only a single dose of AOA (i.e. rise, peak, decay), it is also possible to continue the analysis on sequential doses of AOA as would often be used in treatment (e.g. injection 4 times daily).

It should be noted that the methods of the present invention can be applied not only to the response of organisms to AOA, but also the response to other conditions, such as hormones, drugs (e.g. for drug sensitivity testing), environmental or other agents. These agents can be so analyzed, as long as the response is detectable by the detector employed. In many cases, a stain of some sort may be required in order to make the response to the condition visible.

In the discussion above, the timing of the application of AOA can be related either to the time at which the bacteria are first placed into growth medium, or alternatively, to the time at which bacterial growth is first detected (e.g. through changes in the size of the bacteria, or the presence of daughter cells). In the latter case, growth can be monitored continuously, and AOA added to the incubation at such time as it is determined that the lag time has completed. The completion of lag time will generally be that point at which some predetermined fraction of cells have shown signs of growth, which is preferably less than 50% of cells, and more preferably less than 30% of cells, and most preferably at less than 20% of cells.

Examples of the use of microscopy to demonstrate cell growth are provided by J. R. Lawrence, D. R. Korber, and D. E. Caldwell (1989) "Computer-enhanced darkfield microscopy for the quantitative analysis of bacterial growth and behavior on surfaces", *J. Microbiol. Methods* 10: 123-138 and A. Elfwing, Y. LeMarc, J. Baryani, and A. Ballagi (2004) "Observing Growth and Division of Large Numbers of Individual Bacteria by Image Analysis", *Applied and Environmental Microbiology* 70(2):675-678. It should be noted from Elfwing et al. that growth of bacteria can be measured under laminar flow whereby daughter cells are sheared away, giving a sawtooth optical profile in which the cell size increases, and then with the removal of the daughter cell, the cell size abruptly declines. In the present invention, in addition to cell size (e.g. the number of pixels), the amount of fluorescence or the amount of light scatter can also be used.

Transport to the Detection Surface Using Alternative Means

Figure 39B:
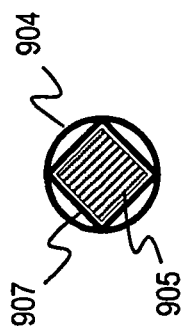
FIG. 39B is a cross-sectional view of the centrifuge tube of FIG. 39A.

Above, the transport to the detection surface using electrophoretic means has been discussed; other means are discussed here. For example, the bacteria can be transferred to the detection surface using centrifugal force. FIG. 39A is a schematic view of a centrifuge tube 900 modified for the concentration of bacteria onto a capture surface 905, and FIG. 39B is a cross-sectional view of the centrifuge tube 900 of FIG. 39A. The tube 900 comprises three separable pieces, a sample tube 903, a capture piece 910, and a bottom piece 912. The sample tube 903 comprises an outer structure 904 that is a cylinder of diameter that fits snugly into a centrifuge fixture for a centrifuge capable of delivering centrifugal force preferably above 200×g, and more preferably above 1000×g and even more preferably above 2500×g. The sample tube 900 further comprises an inner structure 907 that contacts the outer structure 904 for purposes of strength, and the inner structure 907 has either a square or a rectangular cross section. It should be noted that the sample tube 903 will hold a sample 916 containing a bacterial sample, which when centrifuged will deposit the bacteria in the sample onto a capture surface 905 that is preferably either square or rectangular (although other shapes are allowed in the present invention), and whose shape matches the shape of the inner structure 907. The cross-sectional shape of the inner structure 907 is limited by the shape of the capture surface 905, and instead of having an inner structure 907 and an outer structure 904, there can be only an inner structure 907 given either that the centrifugal force and sample tube 903 materials are such that the inner structure 907 can maintain its dimensional integrity without need for the outer structure 904, or that the centrifuge fixture into which the centrifuge tube 900 fits is roughly matched to the shape of the tube 900 (e.g. is square or rectangular).

The sample tube 903 fits snugly onto the capture piece 910, which can include a gasket 914 so that under centrifugation, the bacterial sample 916 is not forced from the sample tube 903. The sample tube 903 generally has interfaces for both the sample tube 903 and the bottom piece 912, and has a top surface in contact with the bacterial sample within the sample tube 903 that has a capture surface that generally has non-specific binding for bacteria or other organisms on the sample. Such non-specific surfaces have been described in detail above. It should be noted that the capture surface can either be placed directly onto an integrated capture piece 910 (for example, a molded plastic piece), or alternatively can be a removeable top piece that, on removal, is a flat square or rectangular piece that is preferably between 100 microns and 1500 microns in thickness and is made of a suitable plastic or glass. The following discussion relates to an integrated capture piece 910.

The bottom piece 912 is molded to fit snugly into the centrifuge fixture for the centrifuge used, and is typically hemispherical or conical. Once again, depending on the centrifuge fixture, the shape of the bottom piece can be various. Furthermore, if the centrifuge fixture is flat on the bottom, the bottom piece 912 can be dispensed with, and the bottom surface of the capture piece 910 would contact then the bottom of the centrifuge fixture.

Figure 39C:
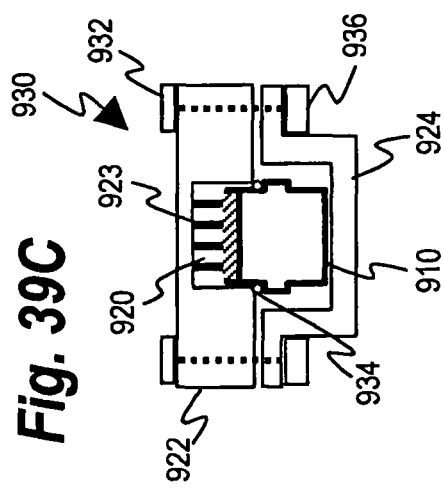
FIG. 39C is a cross-sectional side-view of a detector using the capture piece of FIGS. 39A-B.
Figure 39A:
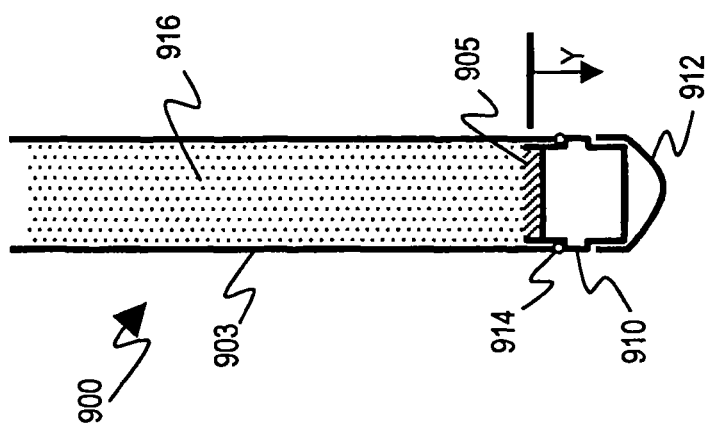
FIG. 39A is a schematic view of a centrifuge tube modified for the concentration of bacteria onto a capture surface.

Upon the bacteria in the sample 916 being centrifuged onto the capture surface 905, the capture piece 910 is separated from the sample tube 903, and placed between a top fixture 922 and a bottom fixture 924 as shown in FIG. 39C, a cross-sectional side-view of a detector 930 using the capture piece 910 of FIGS. 39A-B. The fixtures 922 and 924 are held together with screws 932 and nuts 936 or other means (e.g. clamps), with a gasket 934 providing a water tight seal between the top piece 922 and the capture piece 910. In the top piece 922, above the capture piece 910, are a series of linear walls 923 that fit snugly onto the capture surface 905 such that isolated chambers 920 are created above the capture surface 905. These chambers 920 have input and output ports (not shown) that allow the introduction of growth media, AOA, indicators (e.g. fluorescent antibodies) for cell type, mortal and vital stains and other such media as needed to execute the steps 730, 740, and 750 of FIG. 6. Detection is provided through the top fixture 922; however, if the capture surface 905 is removable from the capture piece 910 as described above, detection can take place through the capture surface given a suitable fixture.

Figure 40A:
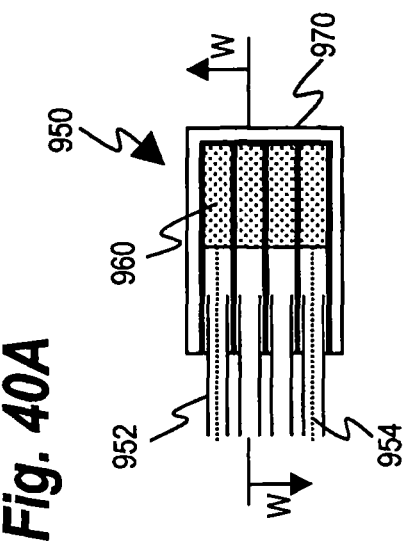
FIGS. 40A-B are a cross-sectional top-view and side-view of a detection system that uses a porous capture filter.
Figure 40B:
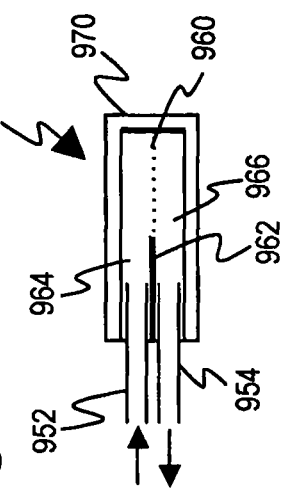

An alternative embodiment is provided in FIGS. 40A-B, which are a cross-sectional top-view and side-view of a filter-based detection device 950 that uses a porous capture filter 960, with the FIG. 40B being shown through cross-section W of the FIG. 40A. The device 950 comprises a series of detector channels (of which four are shown, but which can comprise tens of channels), each of which comprise the porous filter 960, which in conjunction with a separator 962, separates an upper chamber 964 and a lower chamber 966. The filter 960 is at the end of the channel, with movement of medium in through an input port 952, across the upper surface of the separator 962, through the filter 960, back across the lower surface of the separator 962 and then out through an output port 954. The channel is bounded on other sides by outer structure 970, which can comprise a single piece (as shown), or a top piece bonded onto a bottom piece, wherein the top piece, lying above the filter 960, is generally transparent so that bacteria bound to the top surface of the filter 960 can be detected visually. While there can be a separate output port 954 for each channel, the output ports can be shared, as is shown in the figure.

The filter 960 can comprise a track-etched membrane (e.g. polycarbonate, polyethylene terephthalate, glass, aluminum or other material), aluminum oxide, Teflon®, nitrocellulose, and other materials. In certain cases, the filters 960 are manufactured separately, being of different material from that of the separator and the outer structure 970, and are therefore placed onto the porous structural element (not shown) that holds the filter in place and prevents media from flowing from the upper chamber 964 to the lower chamber 962 without going through the filter 960.

The filter preferably has median pore size less than 500 nm, and more preferably less than 250 nm and most preferably less than 100 nm, which will generally be smaller than the smallest bacterial organism to be detected. In general, such pores are difficult to make substantially less than 50 nm, and for very small organisms (e.g. virus particles) that are on the order of or smaller than the diameter of the pores, it is convenient to bind particles to the organisms (e.g. particles comprised of polystyrene or other polymer, gold, ceramic, or other material) using antibodies, aptamers, or electrostatic attraction (e.g. where the particles are covered with a polycationic surface), such that the combination of organism and particles are larger than the pores. It should be noted, however, that these particles must not be used in such large quantity such that when in packed configuration have an area larger than that of the filter 960.

Bacterial samples are generally prepared as described above so as to remove particle contaminants (e.g. dust), mammalian cells, mucus, and other interfering agents, and in general to reduce the sample volume to a milliliter or less (the sample flow rates through the filter can be very low in certain cases, such as track-etched filters). Bacteria introduced in a sample through the input port 952 flow across the filter 960, and are captured on its surface. The bacteria are detected on the surface through the outer structure 970 through means described above. Then, media comprising nutrients, mortal and vital stains, indicators, AOA, and other materials as described in sections on growth and detection above are introduced through the input port 952 and removed through the output port 954. If it is desired that a constant force be placed on the system such that bacteria that newly arise through growth in media do not move far from their place of origin, movement of medium through the system can be maintained.

In another embodiment, sample concentration, transportation and attachment is achieved by simultaneously on a non specific capture surface where multiple forces are applied to effect separation of the bacteria into differing fractions on the basis of size (volume or cross-section), charge-to-mass ratio, relative attachment of electrostatic or magnetic tags, electrophoretic mobility, and other characteristics. In one embodiment, the bacteria are moved horizontally along the chamber through movement of the fluid, which movement may be accomplished via electroosmosis, positive displacement pumps, peristaltic pumps, or other means, or alternatively, the bacteria can move under the application of a directional force (e.g. electrophoresis, magnetic fields, etc.). The vertical directional force on the bacteria may be accomplish via fluid flow (e.g. via filtration), electrophoresis, electroosmosis, centrifugal or by other means. It should be noted that the force in any one direction can be the result of additive or opposing forces from one (e.g. fluid flow can be applied in opposite directions at different cross-sectional locations), two or more of the forces described above. Also, the forces can be oriented so that that are parallel, orthogonal, or a combination of the two.

FIGS. 41A-B are schematic cross-sections of a detection system using multiple forces to effect separation of the bacterial sample. In FIG. 41A, a combined horizontal and vertical fluid movement caused by positive displacement pressure in inlet 803 produces flow out the exit port 802 in the chamber 805 via a track-etched filter 1001. This bulk fluid movement is coordinated with the further application of horizontal electrophoresis using an anode 815 and a cathode 816, which opposes the fluid flow in a simultaneous or sequential manner. That is, in sequential coordination, fluid movement can be performed for a certain period, and then followed by a period of fluid non-movement during which electrophoresis is applied, or the electrophoresis can be applied during movement in simultaneous coordination. In the latter case, the speed of movement or the magnitude of the electrophoretic force can be varied, such that bacteria of two types (denoted by stars 830 and 835 and diamonds 840), clusters of the bacteria types (denoted by 830B and 835B), and sample contaminants 1000 are separated by various physical characteristics such as size, shape, and electrophoretic mobility.

In FIG. 41B, at the conclusion of the separation, the electrophoretic and bulk flow fluid forces have been balanced so that bacteria 830, 835 and 840 and contaminants 1000 are separated on the basis of size and charge. The bacteria 830 separate into regions of individual bacteria 830 and clumped bacteria 830B. Also, there is a separation of live bacteria 830 from dead bacteria 835, which separation occurs due to changes in size, surface properties, and charge (due in part to changes in permeability). These separate areas aid in the identification of bacteria on the filter 1001 and the separation or removal of contaminants 1001 from the sample.

While the cathode 816 is in the upper part of the system shown (i.e. the cathode 816 and the anode 815 are on the same side of the filter 1001, it is also within the spirit of the present invention for the cathode 816 to be placed into the lower part of the system shown, so that the cathode 816 and the anode 815 are on opposite sides of the filter 1001. In this case, bacteria moving across the filter 1001 are affected by a fluid flow, which both moves the bacteria across the filter 1001 and eventually down onto the filter 1001, as well as an electrophoretic force that moves the bacteria only downwards (and to the pores, through which the electrophoretic force is applied). Thus, the forces of fluid flow and electrophoresis can be independently applied, effecting a separation of bacteria and contaminants depending on their responses to these two forces. Indeed, in this case, it can be convenient for the output port 802 to be in the upper part of the system, so that fluid flow forces are almost entirely horizontal, whereas the electrophoretic force is vertical. The use of any permeable membrane supporting electrophoresis can be use in this apparatus instead of the track-etch filter 1001.

It should be noted that there are many configurations of the channels in the device within the spirit of the present invention. For example, while there can be separate filters 960 for each channel, it is convenient for there to be a single filter 960 which is separated by walls between each channel. Furthermore, while the filter 960 is shown to be rectangular within each channel, it is also convenient for the filter 960 to be in an aspect ratio (square or slightly rectangular) that matches the field of view of the optic system used to detect bacteria on the surface of the filter 960. Furthermore, while the input ports 952 and output ports 954 are shown on the same side of the device 950, they can also be located on opposite sides of the device 950, or oriented perpendicularly to one another.

Many Embodiments within the Spirit of the Present Invention

It should be apparent to one skilled in the art that the above-mentioned embodiments are merely illustrations of a few of the many possible specific embodiments of the present invention. It should also be appreciated that the methods of the present invention provide a nearly uncountable number of arrangements of indicators, tags, detectors, mixing means, force application means and more.

Some of the embodiments are described combinatorially in FIG. 43, a block diagram of a biodetection by the present invention.

As shown in Target Identity, the targets can comprise DNA, RNA, protein, starch, lipids (e.g. steroid hormones), and may further comprise combinations of these (e.g. glycoproteins). Furthermore, the targets can comprise organisms or tissues, including bacteria, fungi, viruses, mycoplasma, protozoans, or various types of animal or plant cells (e.g. circulating cells, or tissue culture cells). More generally, the targets can comprise any material or molecule for which a specific probe can be developed.

In an optional Sample Preparation, the target in which the target is present can be prepared for subsequent analysis, for reasons that can include removal of contaminants, concentration to a more easily handled volume, or placement of the targets into a buffer whose characteristics are more appropriate for subsequent analysis steps. This sample preparation can comprise centrifugation (either to centrifuge down the target from the sample for resuspension in another buffer or to centrifuge out particulate contaminants from the targets in solution), ion exchange (e.g. filtration through an ion exchange resin or mixing the sample with ion exchange beads), filtration, electrophoresis (e.g. stacking electrophoresis or gel electrophoresis with extraction), and other forms of biochemical, chemical or physical separation (affinity columns, phase partitioning, precipitation, etc.).

In an optional Tagging, the target is tagged so as to improve either its movement towards the probe, or to make it more detectable by the detector. Those tags affecting mobility comprise electrostatic tags (e.g. for movement under electrophoretic fields), magnetic tags (e.g. for movement in magnetic field), electrostatically polarizable tags (e.g. for movement in dielectrophoretic fields) and other tags with physical properties that change the movement of targets in different physical or chemical environments. The tags can also comprise indicator tags, such as light scattering particles, electrochemical tags, fluorescent tags, upconverting phosphor tags, quantum dot tags, or enzyme tags (e.g. peroxidase) that will improve the visibility of the tagged target at a subsequent stage. It should be noted that the tag can incorporate both functionalities (movement and detection), either within a single entity (e.g. a light scattering particle that is also electrostatically polarizable or a magnetic particle that scatters light), or resulting from the bonding together of two different entities with different functionality.

It should also be noted that Tagging may occur multiple times, for example in a first instance to enhance mobility and in a second instance to enhance detection. Indeed, Tagging can occur either before the Target Capture (discussed below), after Target Capture, or both before and after Target Capture.

In Target Capture, the target is captured on a surface. This capture generally involves a movement of the target to the surface, and can comprise electrophoresis, dielectrophoresis, centrifugation, magnetic field capture, filtration, gravity, or other forces that result in the capture of the target on the surface. The surface can have either a natural affinity for the target, or can be treated in such a way as to have a specific affinity for some targets (e.g. coating the surface with an antibody), or a general affinity for many targets (e.g. coating the surface with a polycationic polymer).

In concert with the Target Capture, optional Horizontal Movement can be performed, wherein the Horizontal Movement uses electrophoresis, filtration, bulk flow (e.g. from pumps or electroendoosmosis), or other means to affect the distribution of the target on the surface. The distribution can either be made more uniform (e.g. to allow the target to come into proximity with more of the surface), or alternatively, can be used to place targets with different characteristics at different locations on the surface (e.g. to "fractionate" bacteria on the basis of their electrophoretic mobilities).

In Washing, the unbound target is removed, and an attempt can be made to remove non-specifically bound material. The Washing can comprise electrophoresis, dielectrophoresis, chemical (e.g. salt, pH, surfactant, affinity competitor), physical (e.g. temperature), magnetic field, or other means of affecting the binding of the probe (or non-specific capture agent) to the captured target. It should be noted that some fraction of the non-specifically bound material can be more tightly bound than that of the specifically-bound target. The washing can also distinguish specifically-bound target as that material that is released between two levels of stringency.

In optional Staining, the bound target can be stained in order to affect its visibility, and can be used to ascertain the state of the target. This is particularly useful in the case of cells (bacterial, animal or plant), where the use of mortal and vital stains indicate whether the cells are alive or dead, and the use of serotyping (generally with the use of labeled monoclonal or polyclonal antibodies) can establish the identity of the cells (e.g. genus, species, cell type). It should be noted that Staining can alternatively be performed as part of Tagging (e.g. a fluorescent tag can be attached via a serotype specific antibody), prior to Target Capture, between Target Capture and Washing or after Washing. The time at which Staining is best performed depends on the persistence of the stain, the degree to which the stain interferes with other steps, and other reasons.

Alternatively or in conjunction with the Staining is optional Incubation, in which the target is incubated, which is generally performed with live targets (e.g. bacteria). In this case, the incubation is performed conveniently in a growth medium conducive to growth, and can be accompanied with a biological condition, such as the application of an AOA, challenge with a hormone, drug, temperature, or other biological mediator. It is best if the expected response of the target to the condition is visible by the detector, which can involve the use of a stain. Staining may also be employed after the Incubation, and it should be appreciated that the application of the stain can occur multiple times in an analysis (e.g. so that cells that are newly grown in the Incubation can be stained with the stain, or so that the response of the cells to the condition).

In Detection, the targets are detected by the detector. The detector can be an optical detector, which can be an imager/camera, which can view the targets via brightfield, darkfield, frequency change (e.g. fluorescence, upconverting phosphors, quantum bits), phase, emitted light (e.g. chemiluminescence), or other imaging means. The detection can also comprise a photomultiplier tube, in conjunction with a laser scanner, or with averaging optics that spread the light from the entire field or a substantial portion of the field onto the light gather source (which could also utilize a photodiode, photoresistor or other light measurement device). Also, the detection can involve SPR, either in an imaging mode, or in averaging mode. It should be noted that there are non-optical means of detection, using for example measurement of electrical current, which can be used with certain embodiments of the present invention.

In some instances, it is convenient to perform the detection multiple times at different washing stringencies, in which case detection can be followed by another cycle of washing and detection. Also, as shown, it can also be convenient to perform detection multiple times after continued Incubation or multiple Staining (e.g. to determine the susceptibility of organisms to AOA).

In Analysis, the data from the detector is analyzed. The Analysis can comprise tracking individual targets, or measurement and analysis of bulk properties of the signal generated by the detector. Additionally, the analysis can look at the change of signal over time (e.g. in response to the growth of organisms, their viability in differing AOA concentrations, or target binding at different washing stringencies).

Figure 42:
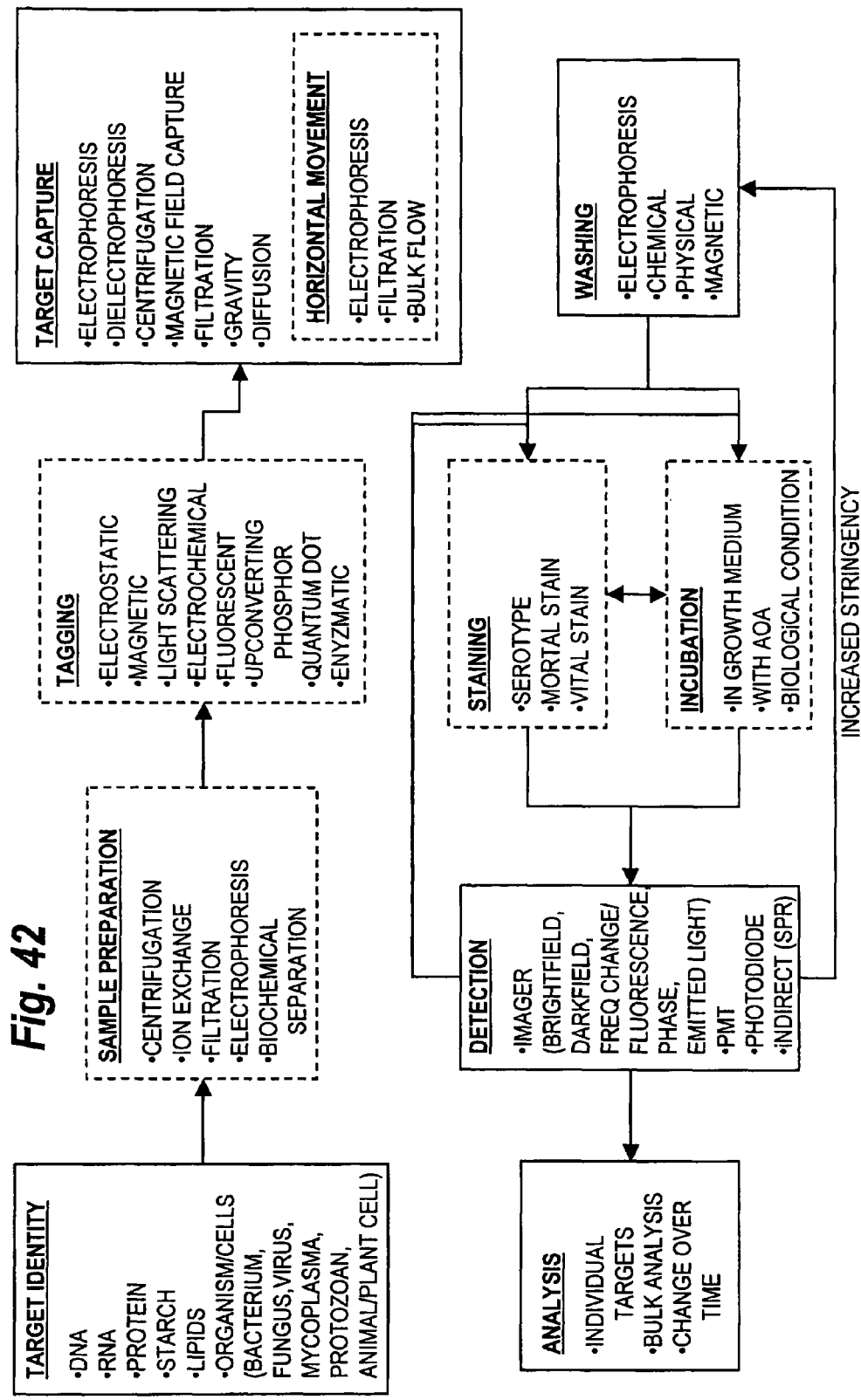
FIG. 42 is a block diagram of a biodetection by the present invention.

It should be noted that the embodiments of the present invention are not comprehensively enumerated in FIG. 42, and that the multitudinous embodiments embedded combinatorially in the figure are illustrative only.

Numerous and varied other arrangements can be readily devised by those skilled in the art without departing from the spirit and scope of the invention. Moreover, all statements herein reciting principles, aspects and embodiments of the present invention, as well as specific examples thereof, are intended to encompass both structural and functional equivalents thereof. Additionally, it is intended that such equivalents include both currently known equivalents as well as equivalents developed in the future, i.e. any elements developed that perform the same function, regardless of structure.

In the specification hereof any element expressed as a means for performing a specified function is intended to encompass any way of performing that function. The invention as defined by such specification resides in the fact that the functionalities provided by the various recited means are combined and brought together in the manner which the specification calls for. Applicant thus regards any means which can provide those functionalities as equivalent as those shown herein.

What is claimed is:

1. A method of detecting the response of a test microorganism to a condition, comprising:
    capturing the microorganism on a surface of a substrate using an applied force, wherein the surface has an affinity for the microorganism;
    detecting at a first time a property of the microorganism on the surface with a camera;
    placing the microorganism in a condition;
    detecting at a second time the property of the microorganism on the surface with the camera; and
    determining the response of the microorganism to the condition by the amount of difference of the property of the microorganism between the first time and the second time.

2. The method of claim 1, wherein the microorganism is selected from the set consisting of bacterium, mycoplasma, protozoan, fungus, and plant cell and animal cell.

3. The method of claim 1, wherein the affinity of the surface is conferred by a cationic polymer.

4. The method of claim 1, wherein the applied force comprises electrophoresis.

5. The method of claim 4, wherein the electrolyte in which electrophoresis occurs comprises an oxidizing agent and a reducing agent, wherein the potential at which the electrophoresis occurs is below 2 volts.

6. The method of claim 1, wherein the applied force comprises filtration.

7. The method of claim 1, wherein the applied force comprises magnetic force, and a paramagnetic tag is bound to the microorganism in order to confer responsiveness of the microorganism to a magnetic field.

8. The method of claim 1, wherein the force comprises centrifugation.

9. The method of claim 1, wherein the force comprises dielectrophoresis.

10. The method of claim 1, wherein the property comprises the amount of stain that is detected.

11. The method of claim 10, wherein the stain is selected from the set consisting of vital stain and mortal stain.

12. The method of claim 1, wherein the property comprises the size of the organism.

13. The method of claim 1, wherein the property comprises the presence of a second microorganism at the second time adjacent to the location of the test microorganism, wherein the second microorganism is not present at the first time.

14. The method of claim 1, wherein the condition comprises the presence of an agent selected from the set consisting of antibiotic, bacteriophage, animal virus, double-stranded RNA, DNA, anticancer drug, antifungal drug, antimalarial drug, and antiprotozoal drug.

15. The method of claim 1, wherein determining at the first time additionally comprises locating the microorganism on the surface with the camera and storing the location of the microorganism in a storage medium, whereby the microorganism is located at the second time by retrieving the location from the storage medium.

* * * * *